US012036241B2

(12) United States Patent
Rosen et al.

(10) Patent No.: US 12,036,241 B2
(45) Date of Patent: Jul. 16, 2024

(54) COMPOSITIONS AND METHODS FOR IMMUNE CELL MODULATION IN ADOPTIVE IMMUNOTHERAPIES

(71) Applicants: Fate Therapeutics, Inc., San Diego, CA (US); Juno Therapeutics, Inc., Seattle, WA (US)

(72) Inventors: Jonathan Rosen, San Diego, CA (US); Eigen Peralta, San Diego, CA (US); Ian Hardy, San Diego, CA (US); Betsy D. Rezner, San Diego, CA (US); Christian Maine, San Diego, CA (US); Daniel Shoemaker, San Diego, CA (US); David Robbins, Temecula, CA (US); Lucas Thompson, Seattle, WA (US)

(73) Assignees: FATE THERAPEUTICS, INC., San Diego, CA (US); JUNO THERAPEUTICS, INC., Seattle, WA (US)

( * ) Notice: Subject to any disclaimer, the term of this patent is extended or adjusted under 35 U.S.C. 154(b) by 1009 days.

(21) Appl. No.: 16/631,781

(22) PCT Filed: Jul. 19, 2018

(86) PCT No.: PCT/US2018/042822
§ 371 (c)(1),
(2) Date: Jan. 16, 2020

(87) PCT Pub. No.: WO2019/018603
PCT Pub. Date: Jan. 24, 2019

(65) Prior Publication Data
US 2020/0179451 A1   Jun. 11, 2020

Related U.S. Application Data

(60) Provisional application No. 62/628,733, filed on Feb. 9, 2018, provisional application No. 62/534,537, filed on Jul. 19, 2017.

(51) Int. Cl.
A61K 35/17   (2015.01)
A61K 45/06   (2006.01)
A61P 35/00   (2006.01)
C12N 5/0783  (2010.01)

(52) U.S. Cl.
CPC .............. *A61K 35/17* (2013.01); *A61K 45/06* (2013.01); *A61P 35/00* (2018.01); *C12N 5/0636* (2013.01); *C12N 5/0646* (2013.01); *C12N 2501/999* (2013.01); *C12N 2506/02* (2013.01); *C12N 2506/45* (2013.01); *C12N 2510/00* (2013.01)

(58) Field of Classification Search
CPC ........ A61K 35/17; A61P 35/00; C12N 5/0636
See application file for complete search history.

(56) References Cited

U.S. PATENT DOCUMENTS

| 9,376,664 B2 | 6/2016 | Efe et al. |
| 9,556,417 B2 | 1/2017 | Efe et al. |
| 2017/0136063 A1 | 5/2017 | Perez et al. |
| 2018/0072992 A1 | 3/2018 | Valamehr et al. |

FOREIGN PATENT DOCUMENTS

| WO | WO 2015/188119 A1 | 12/2015 |
| WO | WO 2017/070395 A1 | 4/2017 |
| WO | WO 2018/106595 A1 | 6/2018 |
| WO | WO 2019/018603 A2 | 1/2019 |

OTHER PUBLICATIONS

McLornan et al. (Curr Hematol Malig Rep (2015) 10:370-379) (Year: 2015).*
Green et al. Development and validation of a drug activity biomarker that shows target inhibition in cancer patients receiving enzastaurin, a novel protein kinase C-β inhibitor. Clinical Cancer Research 2006, 12;11:3408-3415. (Year: 2006).*
Kelly et al. Phosphoinositide-dependent kinase 1 (PDK1) haplo-insufficiency inhibits production of alpha/beta but not gamma delta T lymphocytes. FEBS Letters 2006, 580;8:2135-2140. (Year: 2006).*
Eyquem et al. Targeting a CAR to the TRAC locus with CRISPR/Cas9 enhances tumour rejection. Nature 2017, 542:113-117. (Year: 2017).*
Galat et al. Cytokine-free directed differentiation of human pluripotent stem cells efficiently produces hemogenic endothelium with lymphoid potential. Stem Cell Research & Therapy 2017, 8;67:1-11. (Year: 2017).*
Beavis et al. Targeting the adenosine 2A receptor enhances chimeric antigen receptor efficacy. Journal of Clinical Investigation 2017, 127;3:929-941. (Year: 2017).*
Najafov et al. Characterization of GS2334470, a novel and highly specific inhibitor of PDK1. Biochemical Journal 2011, 433:357-369. (Year: 2011).*
Berger et al., "Adoptive transfer of effector CD8+ T cells derived from central memory cells establishes persistent T cell memory in primates," *J. Clin. Invest.*, 118(1):294-305 (2008).
Bracci et al., "Cyclophosphamide enhances the antitumor efficacy of adoptively transferred immune cells through the induction of cytokine expression, B-cell and T-cell homeostatic proliferation, and specific tumor infiltration," *Clin. Cancer Res.*, 13:644-653 (2007).
Emmanouilidi et al., "Targeting PDKI for Chemosensitization of Cancer Cells," *Cancers*, 9(10):140 (2017).
Esteban et al., "Vitamin C enhances the generation of mouse and human induced pluripotent stem cells," *Cell Stem Cell*, 6:71-79 (2010).

(Continued)

*Primary Examiner* — Allison M Fox
*Assistant Examiner* — Jennifer S Spence
(74) *Attorney, Agent, or Firm* — Greenberg Traurig, LLP

(57) ABSTRACT

Compounds that either produce a higher proportion or greater absolute number of phenotypically identified naive, stem cell memory, central memory T cells, adaptive NK cells, and type I NKT cells are identified. Compositions and methods for modulating immune cells including T, NK, and NKT cells for adoptive cell therapies, such as those providing improvements in one or more therapeutic outcomes, are provided.

21 Claims, 25 Drawing Sheets

(56) References Cited

OTHER PUBLICATIONS

Feng et al., "Molecules that promote or enhance reprogramming of somatic cells to induced pluripotent stem cells," *Cell Stem Cell*, 4:301-312 (2009).

Flynn et al., "Stem memory T cells (TSCM)-their role in cancer and HIV immunotherapies," *Clin. Trans. Immunol.*, 3(7):e20 (2014).

Hinton et al., "The serine kinase phosphoinositide-dependent kinase 1 (PDK1) regulates T cell development," *Nat. Immunol.*, 5(5):539-545 (2004).

Huangfu et al., "Induction of pluripotent stem cells by defined factors is greatly improved by small-molecule compounds," *Nat. Biotechnol.*, 26:795-797 (2008).

Huangfu et al., "Induction of pluripotent stem cells from primary human fibroblasts with only Oct4 and Sox2," *Nat. Biotechnol.*, 26:1269-1275 (2008).

Ichida et al., "A small-molecule inhibitor of tgf-Beta signaling replaces sox2 in reprogramming by inducing nanog," *Cell Stem Cell*, 5:491-503 (2009).

Kagoya et al., "BET bromodomain inhibition enhances T cell persistence and function in adoptive immunotherapy models," *J. Clin. Invest.*, 126(9):3479-3494 (2016).

Kim et al., "Generation of human induced pluripotent stem cells by direct delivery of reprogramming proteins," *Cell Stem Cell*, 4:472-476 (2009).

Lyssiotis et al., "Reprogramming of murine fibroblasts to induced pluripotent stem cells with chemical complementation of Klf4," *Proc. Natl. Acad. Sci. USA*, 106:8912-8917 (2009).

Maherali et al., "Tgfbeta signal inhibition cooperates in the induction of iPSCs and replaces Sox2 and cMyc," *Curr. Biol.*, 19:1718-1723 (2009).

Mahnke et al., "The who's who of T-cell differentiation: human memory T-cell subsets," *Eur. J. Immunol.*, 43:2797-2809 (2013).

Muyldermans et al., "Sequence and structure of VH domain from naturally occurring camel heavy chain immunoglobulins lacking light chains," *Protein Eng.*, 7:1129-1135 (1994).

Nuttall et al., "Isolation of the new antigen receptor from wobbegong sharks, and use as a scaffold for the display of protein loop libraries," *Mol. Immunol.*, 38:313-326 (2001).

Pepper et al., "Origins of CD4(+) effector and central memory T cells," *Nat. Immunol.*, 12(6): 467-471 (2011).

Saha et al., "Technical challenges in using human induced pluripotent stem cells to model disease," *Cell Stem Cell*, 5:584-595 (2009).

Shi et al., "A combined chemical and genetic approach for the generation of induced pluripotent stem cells," *Cell Stem Cell*, 2:525-528 (2008).

Shi et al., "Induction of pluripotent stem cells from mouse embryonic fibroblasts by Oct4 and Klf4 with small-molecule compounds," *Cell Stem Cell*, 3:568-574 (2008).

Silva et al., "Promotion of reprogramming to ground state pluripotency by signal inhibition," *Plos Bio.*, 6(10):e253 (2008).

Sommermeyer et al., "Chimeric antigen receptor-modified T cells derived from defined CD8+ and CD4+ subsets confer superior antitumor reactivity in vivo," *Leukemia*, 30(2):492-500 (2016).

Takahashi et al., "Induction of pluripotent stem cells from adult human fibroblasts by defined factors," *Cell*, 131:861-872 (2007).

Takahashi et al., "Induction of pluripotent stem cells from mouse embryonic and adult fibroblast cultures by defined factors," *Cell*, 126:663-676 (2006).

Yamanaka, "Elite and stochastic models for induced pluripotent stem cell generation," *Nature*, 460:49-52 (2009).

Yu et al., "Induced pluripotent stem cell lines derived from human somatic cells," *Science*, 318:1917-1920 (2007).

Zhou et al., "Generation of induced pluripotent stem cells using recombinant proteins," *Cell Stem Cell*, 4:381-384 (2009).

Busschots et al., "Substrate-Selective Inhibition of Protein Kinase PDKI by Small Compounds that Bind to the PIF-Pocket Allosteric Docking Site," *Chem Biol*, 2012, 12(9):1152-1163.

Rettenmaier et al., "A small-molecule mimic of a peptide docking motif inhibits the protein kinase PDK1," *P.N.A.S.*, 2014, 111(52): 18590-18595.

* cited by examiner

| Compound No. | Compound | T-I+2- | T-I+2+ | T+I+2- | Triple+ | T+I-2- | T+I-2+ | Triple - | T-I-2+ |
|---|---|---|---|---|---|---|---|---|---|
| 1 | OTX015 | 33.03 | 0.34 | 2.43 | 12.92 | 0.23 | 0.75 | 0.12 | 2.34 |
| 5 | Pyr6 | 7.88 | 0.00 | 0.32 | 0.04 | 0.81 | 0.23 | 1.58 | 1.18 |
| 17 | Pacritinib | 3.28 | 0.01 | 0.29 | 0.39 | 0.89 | 2.88 | 0.76 | 10.65 |
| 18 | Tofacitinib | 1.22 | 0.00 | 0.25 | 1.88 | 0.58 | 7.63 | 0.13 | 3.60 |
| 21 | GSK2334470 | 9.55 | 0.01 | 0.37 | 0.15 | 0.39 | 0.61 | 1.44 | 18.72 |
| 23 | AZ628 | 116.10 | 0.32 | 0.39 | 1.03 | 0.07 | 1.14 | 1.16 | 18.34 |
| Vehicle | DMSO | 1.00 | 1.00 | 1.00 | 1.00 | 1.00 | 1.00 | 1.00 | 1.00 |

| Comp. No. | Comp. | Target/Class | Target/Class Category | 1 CD27 MFI | 2 % CD62L+ & CCR7+ | 3 Viability |
|---|---|---|---|---|---|---|
| 1 | OTX015 | BET inhibitor | A | | +++ | + |
| 2 | CPI-203 | BET inhibitor | A | + | ++ | +++ |
| 3 | JQ1 | BET inhibitor | A | = | = | ++ |
| 4 | PHA-793887 | CDK inhibitor | B | +++ | + | + |
| 5 | Pyr6 | CRAC channel Ca entry blocker | C | +++ | + | + |
| 6 | BTP 2 | CRAC channel Ca entry blocker | C | +++ | + | ++ |
| 7 | Etoricoxib | Cyclooxygenase inhibitor | D | | | ++ |
| 8 | Sertindole | Dopamine receptor antagonist | E | | = | + |
| 9 | XMD8-92 | ERK5/BMK1 inhibitor | F | | ++ | ++ |
| 10 | Flunisolide | Glucocorticoid | G | | | + |
| 11 | Dexamethasone Acetate | Glucocorticoid | G | = | = | ++ |
| 12 | Amcinonide | Glucocorticoid | G | | | + |
| 13 | BMS-536924 | IGF-1R inhibitor | H | +++ | = | +++ |
| 14 | TPCA-1 | IKK inhibitor | I | +++ | ++ | = |
| 15 | Bardoxolone Methyl | IKK inhibitor | I | + | +++ | +++ |
| 16 | Ruxolitinib | JAK inhibitor | J | +++ | + | + |
| 17 | Pacritinib | JAK inhibitor | J | + | | +++ |
| 18 | Tofacitinib | JAK inhibitor | J | +++ | +++ | + |
| 19 | CEP33779 | JAK inhibitor | J | +++ | ++ | ++ |
| 20 | KIN001-051 | Lck inhibitor | K | | | |
| 21 | GSK2334470 | PDK-1 inhibitor | L | ++ | +++ | +++ |
| 22 | GDC-0879 | Raf inhibitor | M | ++ | + | ++ |
| 23 | AZ628 | Raf inhibitor | M | | | |
| 24 | Dabrafenib | Raf inhibitor | M | +++ | +++ | |
| 25 | R788 | Syk inhibitor | N | +++ | ++ | |
| 26 | PRT062607 | Syk inhibitor | N | +++ | = | |

FIG. 8A

| Comp. No. | 4 Expansion | 5 Tcm mini panel score | 6 Tim-3 MFI (Inverse) | 7 At Least 2 Cytokines | 8 Single Cytokine Il2 or IFNγ |
|---|---|---|---|---|---|
| 1 | + | +++ | +++ | ++ | +++ |
| 2 | + | +++ | ++ | | |
| 3 | + | +++ | = | | |
| 4 | | + | | | |
| 5 | ++ | +++ | ++ | - | ++ |
| 6 | ++ | +++ | + | | |
| 7 | ++ | | | | |
| 8 | + | + | | | |
| 9 | + | +++ | +++ | | |
| 10 | +++ | ++ | = | | |
| 11 | +++ | + | = | | |
| 12 | ++ | + | = | | |
| 13 | ++ | ++ | + | | |
| 14 | ++ | +++ | + | | |
| 15 | +++ | ++ | = | | |
| 16 | + | +++ | +++ | | |
| 17 | ++ | + | | = | +++ |
| 18 | | +++ | +++ | + | ++ |
| 19 | ++ | ++ | ++ | | |
| 20 | | ++ | | | |
| 21 | ++ | ++ | ++ | - | +++ |
| 22 | +++ | ++ | | | |
| 23 | | +++ | | = | +++ |
| 24 | + | ++ | + | | |
| 25 | ++ | +++ | ++ | | |
| 26 | +++ | ++ | | | |

FIG. 8B

| Comp. No. | In Vitro Killing Ability | Serial Restim Round 3 Expansion | Serial Restim Round 4 Expansion | Serial Restim Total Expansion | In Vivo Efficacy |
|---|---|---|---|---|---|
| 1 | + | +++ | +++ | +++ | = |
| 2 | + | + | ++ | ++ | + |
| 3 | | | | | |
| 4 | + | + | + | ++ | + |
| 5 | + | + | ++ | ++ | + |
| 6 | | | | | |
| 7 | | | | | |
| 8 | | | | | |
| 9 | + | + | + | + | |
| 10 | + | + | ++ | ++ | + |
| 11 | | | | | |
| 12 | | | | | |
| 13 | + | ++ | + | ++ | ++ |
| 14 | + | ++ | ++ | ++ | = |
| 15 | + | ++ | ++ | ++ | = |
| 16 | + | +++ | + | ++ | |
| 17 | + | +++ | +++ | +++ | ++ |
| 18 | | | | | |
| 19 | | | | | |
| 20 | + | + | ++ | ++ | = |
| 21 | + | +++ | +++ | +++ | ++ |
| 22 | + | +++ | +++ | +++ | ++ |
| 23 | + | + | +++ | +++ | ++ |
| 24 | + | +++ | +++ | + | = |
| 25 | + | +++ | +++ | +++ | ++ |
| 26 | + | + | ++ | ++ | ++ |

FIG. 8C

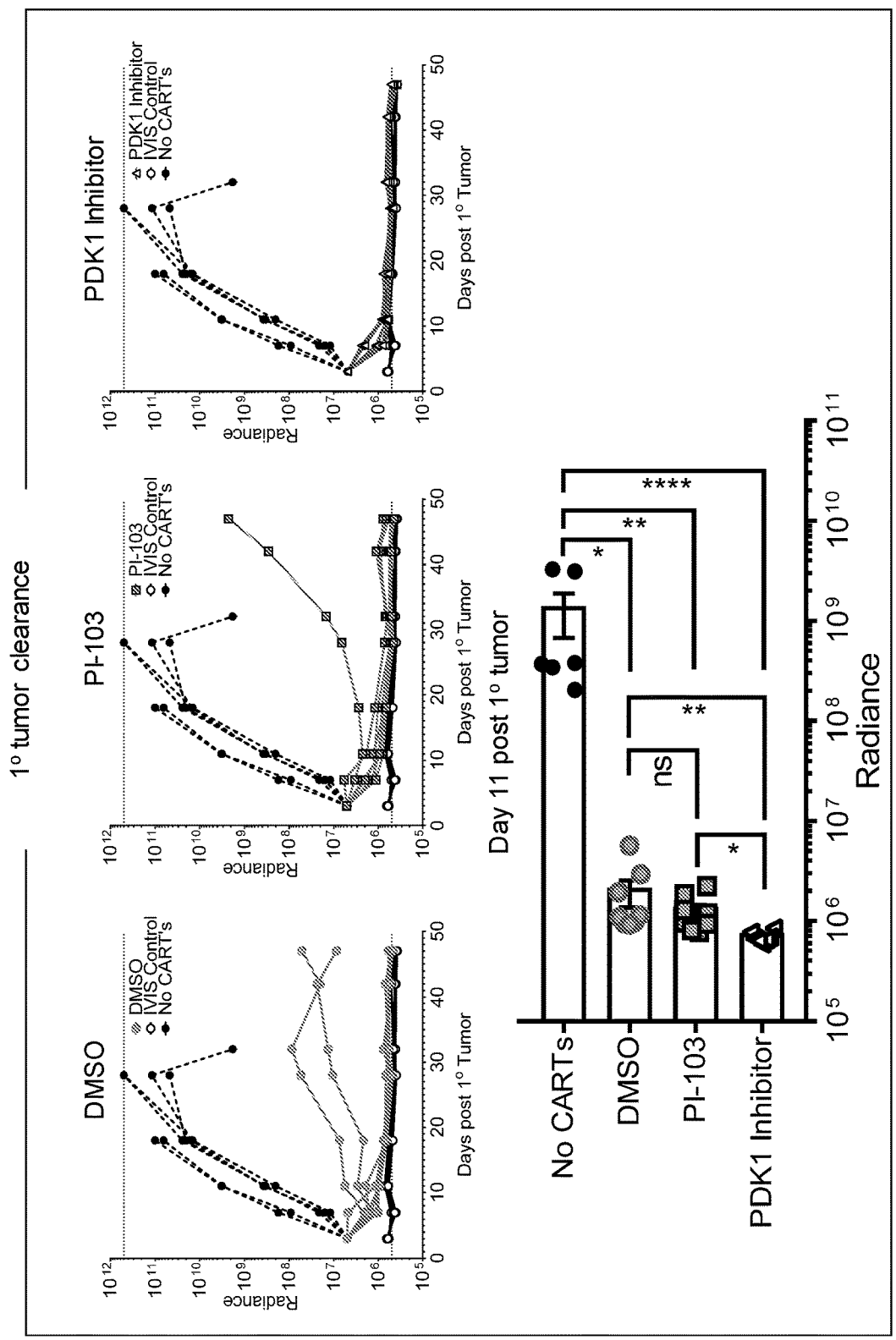

COMPOSITIONS AND METHODS FOR IMMUNE CELL MODULATION IN ADOPTIVE IMMUNOTHERAPIES

RELATED APPLICATION

This application is a U.S. National Stage Application under 35 U.S.C. § 371 of International Patent Application No. PCT/US2018/042822, filed Jul. 19, 2018, which claims priority to U.S. Provisional Application Ser. No. 62/534,537, filed Jul. 19, 2017, and U.S. Provisional Application Ser. No. 62/628,733, filed Feb. 9, 2018, the entire disclosures of which are hereby incorporated by reference in their entireties.

FIELD OF THE INVENTION

The present disclosure is broadly concerned with the field of adoptive immune cell therapies. More particularly, the present disclosure is concerned with the use of small molecules for modulating immune-cells suitable for adoptive cell therapies.

BACKGROUND OF THE INVENTION

Adoptive immunotherapy generally involves administration of immune cells to patients having cancer, tumors, or infections, whereby the administered immune cells generally provide a therapeutic benefit to the patients. Generally speaking, immune cells suitable for immunotherapy include, but are not limited to, B cells, dendritic cells (DC), T cells, Natural Killer (NK) cells, NKT (Natural Killer T) cells, and hematopoietic stem or progenitor cells. Mediating complete and durable disease responses in patients is the central goal of these cell-based immunotherapies.

Aspects of certain biological mechanisms behind the effectiveness of adoptive T cell therapies, including, but not limited to, CAR-T cells, TCR-T cells, virus-specific T cells (VSTs) and tumor-infiltrating T cell (TILs), highlight the importance of certain attributes associated with transferred T cells and certain inhibitory barriers posed by the host and tumor cells that may in some contexts need to be overcome for optimal success in the treatment of cancer. Among T cell factors, the avidity of the T cell receptor (TCR) or chimeric antigen receptor (CAR), the proliferative and survival capacities, migration to the tumor site(s), and the ability to sustain effector functions within the tumor, based, for example, on information from certain correlative studies, can be important in some contexts for triggering the eradication of malignant cells. Adding another layer of complexity, whereas certain desirable attributes are recognized, the pathways or factors impacting these attributes may not be entirely clear, which may in some cases limit the ability to obtain cells having desired quantity and quality for certain therapeutic uses. Among the provided embodiments are those addressing such needs.

Using previous methods of CAR-T cell therapy as an example, the therapeutic composition may encounter one or multiple challenges, such as those associated with CAR-T potency and persistence, migration to the tumor, the immunosuppressive tumor microenvironment, tumor heterogeneity and patient safety.

Additional methods are needed, for example, those capable of enhancing therapeutic efficacy of T cell therapies and other cellular therapies, and/or improving persistence and/or migration of engineered cells following administration. For example, there is a need not only for compositions and methods useful for maintaining and expanding desired immune cell subsets, but also for those useful for reducing cell differentiation during expansion, and for those useful for generating therapeutic compositions having or being enriched for cells (or engineered cells) of a less differentiated phenotype, and/or that contain or are enriched for—or in which engineered or therapeutic cells are enriched for— one or more desired immune cell subsets, such as those that have greater capacity to proliferate and persist and/or to improve one or more therapeutic outcomes for example in the context of various adoptive immunotherapies. Among the provided embodiments are those addressing such needs.

Additional methods and compositions are needed in the context of NK-cell based therapies. Natural killer cells have traditionally been categorized as innate immune cells that are characterized as being relatively short-lived and exhibit minimal change in response to secondary exposure to a stimulus, displaying limited target memory responses. However, both activating and inhibitory NK cell receptors can play important roles, such as in self-tolerance and sustaining NK cell activity. NK cells in some contexts can readily adjust to the immediate environment and formulate antigen-specific immunological memory, which is fundamental for responding to secondary exposure to the same antigen. For example, a subpopulation of NK cells that may be referred to as adaptive NK cells or memory NK cells, can have many functional characteristics similar to CD8+ T cells, including being longer-lived and having enhanced response to stimuli after an initial exposure (Min-Oo et al. 2013). Among the provided embodiments are those addressing such needs.

SUMMARY OF THE INVENTION

It is believed that, like T and NK cells, improvements can be made to isolate more efficacious NKT cells, a type of CD1d-restricted T cell playing a role in both the innate and adaptive immune systems, which can be targeted for modulation to yield an improved cell therapy.

Thus, a manufacturing approach that can enhance the desired T, NK or NKT cell subsets both in quantity and quality could provide a significant enhancement of their therapeutic efficacy.

There is a need in the art for immune cell subsets with improved therapeutic efficacy.

Provided are methods and compositions addressing such needs and providing other related advantages, including in the field of immune cell therapy.

The present invention in some embodiments provides compositions and methods for modulating one or more populations or subpopulations of immune cells to improve their therapeutic potential for adoptive immunotherapies. It is an object of embodiments of the present invention to provide one or more compounds, either alone or in combination to improve proliferation, persistence, cytotoxicity, and/or cell recall/memory of therapeutic immune cells by, for example, increasing the number or relative ratio of a subpopulation of cells that displays improvement in at least one of the following qualities that are expected to result in better immunotherapeutic results: migration, homing, cytotoxicity, maintenance, expansion, persistence, longevity, and desired states of differentiation.

One aspect of the invention provides a composition for improving therapeutic potential of immune cells suitable for adoptive cell-based therapies, and the composition comprises one or more modulating agents selected from a group consisting of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor. The one or more agents improve therapeutic potential of immune cells, or one or more subpopulations thereof, upon contacting the cells. In some embodiments, the modulation of the immune cells is ex vivo. In some embodiments, the one or more modulating agents comprise at least one of the compounds of Table 1, or salts, esters, ethers, solvates, hydrates, stereoisomers, or prodrugs thereof. In some embodiments, the one or more modulating agents comprise a BET inhibitor, an IKK inhibitor, a JAK inhibitor, a PDK1 inhibitor, a Raf inhibitor, or a Syk inhibitor. In some embodiments, the one or more modulating agents comprise at least a PDK1 inhibitor. In some other embodiments, the one or more modulating agents comprise at least a Raf inhibitor. In some other embodiments, the one or more modulating agents comprise at least a Syk inhibitor. In yet another embodiment, the one or more modulating agents comprise at least one of GSK2334470, AZ628, GDC-0879, Dabrafenib, R788, pacritinib, Bardoxolone methyl, and PRT062607. In one embodiment, the one or more modulating agents comprise at least GSK2334470. In another embodiment, the one or more modulating agents comprise at least AZ628. In yet another embodiment, the one or more modulating agents comprise R788. In some other embodiments, the composition of one or more modulating agents comprises Bardoxolone methyl.

In some embodiments, the one or more modulating agents modulates cell expansion, maintenance and/or differentiation, and thereby improve proliferation, cytotoxicity, cytokine response and secretion, cell recall, and/or persistence of the immune cells, or one or more subpopulations thereof.

In one embodiment, the one or more modulating agents improves the cell survival rate of the immune cell, or one or more subpopulations thereof both ex vivo and in vivo.

In one embodiment, the one or more modulating agents increases the number or relative ratio of one or more desired cell subpopulations of the immune cells.

In some embodiments, the present invention provides one or more selected agents herein to improve therapeutic efficacy of a population or subpopulation of immune cells, including but not limited to T, NK and NKT cells. In some embodiments, the immune cells suitable for adoptive cell-based therapies comprise T cells, NKT cells, or NK cells. In some embodiments, the immune cells subject to a treatment under one or more modulating agents comprise T cells, as such the one or more desired cell subpopulations has an increased number or relative ratio comprises naïve T cells, stem cell memory T cells, and/or central memory T cells. In some embodiments, the immune cells subject to the treatments using the agents comprise NKT cells, as such the one or more desired cell subpopulations has an increased number or relative ratio comprise type I NKT cells. In some other embodiments, the immune cells subject to a treatment using the agents comprise NK cells, and wherein the one or more desired cell subpopulations has an increased number or relative ratio comprise adaptive NK cells.

In some aspects, the invention provides a composition comprising a population or subpopulation of immune cells, and one or more modulating agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor. In some embodiments, the immune cells are contacted with the one or more of said modulating agents to improve therapeutic potential of the immune cells for adoptive cell therapy in comparison to immune cells without such contact. In some embodiments, the immune cells are contacted with the one or more agents to improve cell expansion, maintenance, differentiation, dedifferentiation, and/or survival rate in comparison to immune cells without the same treatment. In yet some other embodiments, the immune cells are contacted with the one or more of said modulating agents to improve cell proliferation, cytotoxicity, persistence, and/or recall in comparison to immune cells without the same treatment.

In some embodiments, the immune cells contacted with one or more of said modulating agents have an increased number or relative ratio of a desired subpopulation of the immune cells in comparison to immune cells without the same treatment. In some embodiments, the immune cells comprise T, NK or NKT cells. In one embodiment, the composition comprises a population of T cells, as such the desired subpopulation of immune cells after contacting the agent(s) comprise naïve T cells, stem cell memory T cells, and/or central memory T cells. In some embodiments, the composition comprises a population of NKT cells, as such the desired subpopulation of immune cells after contacting the agents comprise type I NKT cells. In yet some other embodiments, the immune cells comprise a population of NK cells, as such the desired subpopulation of immune cells after contacting the agents comprise adaptive NK cells. In other embodiments the adaptive NK cells comprise CD57+ and at least one of NKG2C+, low PLZF, low SYK, low FcεRγ, low EAT-2, low TIGIT, low PD1, low CD7, low CD161, high LILRB1, high CD45RO, and low CD45RA.

In some embodiments, the population or subpopulation of immune cells of the composition are isolated from or comprised in peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered genetically modified immune cells. In some embodiments, the subject may be CMV seropositive. In some other embodiments, the isolated immune cells for modulation are genetically modified (genetically engineered or derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In some embodiments, the immune cells comprise a CAR specific to a tumor or a pathogen antigen selected from a group consisting of AChR (fetal acetylcholine receptor), ADGRE2, AFP (alpha fetoprotein), BAFF-R, BCMA, CAIX (carbonic anhydrase IX), CCR1, CCR4, CEA (carcinoembryonic antigen), CD3, CD5, CD8, CD7, CD10, CD13, CD14, CD15, CD19, CD20, CD22, CD30, CD33, CLLI, CD34, CD38, CD41, CD44, CD49f, CD56, CD61, CD64, CD68, CD70, CD74, CD99, CD117, CD123, CD133, CD138, CD44v6, CD267, CD269, CDS, CLEC12A, CS1, EGP-2 (epithelial glycoprotein-2), EGP-40 (epithelial glycoprotein-40), EGFR(HER1), EGFR-VIII, EpCAM (epithelial cell adhesion molecule), EphA2, ERBB2 (HER2, human epidermal growth factor receptor 2), ERBB3, ERBB4, FBP (folate-binding protein), Flt3 receptor, folate receptor-a, GD2 (ganglioside G2), GD3 (ganglioside G3), GPC3 (glypican-3), GPI00, hTERT (human telomerase reverse transcriptase), ICAM-1, integrin B7, interleukin 6 receptor, IL13Ra2 (interleukin-13 receptor 30 subunit alpha-2), kappa-light chain, KDR (kinase insert domain receptor), LeY (Lewis Y), L1CAM (L1 cell adhesion molecule), LILRB2 (leukocyte immunoglobulin like receptor B2), MART1, MAGE-A1 (melanoma associated antigen A1), MAGE-A3, MSLN (mesothelin), MUC16 (mucin 16), MUCI (mucin I), NKG2D ligands, NY-ESO-1 (cancer-testis antigen), PRI (proteinase 3), TRBCI, TRBC2, TIM-3, TACI, tyrosinase, survivin, hTERT, oncofetal antigen (h5T4), p53, PSCA (prostate stem cell antigen), PSMA (prostate-specific membrane antigen), hROR1, TAG-72 (tumor-associated glycoprotein 72), VEGF-R2 (vascular endothelial growth factor R2), WT-1 (Wilms tumor protein), and antigens of HIV (human immunodeficiency virus), hepatitis B, hepatitis C, CMV (cytomegalovirus), EBV (Epstein-Barr virus), HPV (human papilloma virus).

In one embodiment, the immune cells for modulation and the modulated immune cells obtained therefrom comprise at least a CAR specific to CD19. In another embodiment, the immune cells for modulation and the modulated immune cells obtained therefrom comprise at least a CAR specific to BCMA.

In yet another embodiment, the immune cells are differentiated in vitro from stem cells, hematopoietic stem or progenitor cells, or progenitor cells; or are trans-differentiated in vitro from non-pluripotent cells of hematopoietic or non-hematopoietic lineage. In some embodiments, the immune cells of the composition are genomically engineered and comprise an insertion, a deletion, a nucleic acid replacement (e.g., a substitution of one or more nucleotides, or indel), or a combination thereof. In some particular embodiments, the immune cells of the composition comprise an exogenous nucleic acid encoding a T Cell Receptor (TCR) and/or a Chimeric Antigen Receptor (CAR). In some embodiments, the immune cells isolated from tissue of a subject are genetically engineered, and may comprise a TCR or a CAR. In some embodiments, the immune cells isolated from tissue or a subject is a CAR-T cell.

In still some other embodiments, the immune cells of the composition are differentiated in vitro from stem cells, hematopoietic stem or progenitor cells, or progenitor cells. In one embodiment, the stem cells are induced pluripotent stem cells (iPSCs) or embryonic stem cells (ESCs). In one embodiment, the progenitor cell is a CD34+ hemogenic endothelium cell, a multipotent progenitor cell, a T cell progenitor cell, an NK progenitor cell, or an NKT progenitor cell. In some embodiments, the stem cell, hematopoietic stem or progenitor cell, or progenitor cell is genomically engineered and comprises an insertion, a deletion, or a nucleic acid replacement, or comprises at least one genetically modified modality. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16. In some other embodiments, the immune cells of the composition are trans-differentiated in vitro from non-pluripotent cells of hematopoietic or non-hematopoietic lineage. In some embodiments, the desired subpopulation of immune cells after modulation comprises immune cells having at least one genetically modified modality. In some embodiments, the genetically modified modality comprises at least one of the following: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region; and (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

In some embodiments, the composition comprising the immune cells and one or more of said modulating agents, further comprises one of more additional modulating agents or other additives/agents selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest; an antibody, or an antibody fragment; and a chemotherapeutic agent, a radioactive moiety, or an immunomodulatory drug (IMiD). In some of these embodiments, the antibody, or antibody fragment, specifically binds to a viral antigen. In other embodiments, the antibody, or antibody fragment, specifically binds to a tumor antigen. In some embodiments, the additional additives comprise one or more of a chemotherapeutic agent, a radioactive moiety, and an immunomodulatory drug (IMiD). Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In one specific embodiment, the composition comprises a mixture of a population or subpopulation of immune cells and one or more modulating agents comprising (i) at least one of the compounds of Table 1, or salts, esters, ethers, solvates, hydrates, stereoisomers, or prodrugs thereof (ii) at least a BET inhibitor, an IKK inhibitor, a JAK inhibitor, a PDK1 inhibitor, a Raf inhibitor, or a Syk inhibitor; (iii) at least a PDK1 inhibitor; (iv) at least a Raf inhibitor; (v) at least a Syk inhibitor; (vi) at least one of GSK2334470, AZ628, GDC-0879, Dabrafenib, R788, pacritinib, Bardoxolone methyl, and PRT062607; (vii) at least GSK2334470; (viii) at least Bardoxolone methyl; or (ix) at least AZ628.

In another embodiment, the composition comprising a mixture of a population or subpopulation of immune cells and one or more of said modulating agents, further comprises one or more additives selected from the group consisting of peptides, antibodies, antibody fragments, cytokines, mitogens, growth factors, small RNAs, dsRNA, mononuclear blood cells, feeder cells, feeder cell components or replacement factors, vectors comprising one or more polynucleic acids of interest, chemotherapeutic agents or radioactive moieties, and immunomodulatory drugs (IMiDs). In yet another embodiment, the composition comprising a mixture of a population or subpopulation of immune cells and one or more of said modulating agents also comprises at least one organic solvent selected from the group consisting of dimethyl sulfoxide (DMSO), N,N-dimethylformamide (DMF), dimethoxyethane (DME), dimethylacetamide, ethanol and combinations thereof. In one embodiment, the population or subpopulation of immune cells in the composition comprises T cells. In some embodiment, the T cells in the cell population comprise CAR-T cells.

In some aspects, provided are compositions comprising a population of modulated immune cells that has been contacted with a composition comprising one or more agents selected from at least one modulating agent selected from the group consisting of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor. In some embodiments, the composition provided is a therapeutic composition having the population or subpopulation of modulated immune cells including, but not limited to, T, NK, and NKT cells. In some embodiments, the therapeutic composition can be washed with a buffer substantially free of the modulating agent.

In some embodiments, the modulated cell population comprises immune cells having improved therapeutic potential for adoptive cell therapy in comparison to an unmodulated cell population. In some embodiments, the isolated population of immune cells has improved cell expansion, maintenance, differentiation, dedifferentiation, and/or survival rate in comparison to immune cells without the treatment by the one or more agents. In some embodiments, the isolated population of immune cells has improved cell proliferation, cytotoxicity, cytokine response and secretion, cell recall, and persistence in comparison to immune cells without the treatment by the one or more agents, and in some aspects incubated or treated under conditions otherwise similar but not including such one or more agents. In some other embodiments, the isolated population of immune cells has an increased number or relative ratio of one or more desired subpopulations of the immune cells in comparison to immune cells without the same treatment.

In some embodiments, the isolated population of immune cells treated with one or more of said modulating agents comprises T cells, as such the obtained one or more desired subpopulations of immune cells comprise naïve T cells, stem cell memory T cells, and/or central memory T cells. In some embodiments, the isolated population of immune cells treated with one or more agents comprises NKT cells, as such the obtained one or more desired subpopulations of immune cells comprise type I NKT cells. In yet some other embodiments, the isolated population of immune cells treated with one or more agents comprises NK cells, as such the one or more desired subpopulations of immune cells comprise adaptive NK cells.

In some embodiments of the composition as provided, the isolated population of immune cells may be isolated from peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered genetically modified immune cells. In some embodiments, the subject may be CMV seropositive. In some other embodiments, the isolated immune cells for modulation are genetically modified (genetically engineered or derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In some embodiments of the composition as provided, the isolated population of immune cells may be differentiated from a stem cell, a hematopoietic stem or progenitor cell, or a progenitor cell. In some embodiments, the isolated population of immune cells may be differentiated from a stem cell, a hematopoietic stem or progenitor cell, or a progenitor cell prior to, or during, the treatment by the agent(s). In some embodiments, the stem cell is an induced pluripotent stem cell (iPSC) or embryonic stem cell (ESC). In some embodiments, the progenitor cell is a CD34+ hemogenic endothelium cell, a multipotent progenitor cell, a T cell progenitor cell, an NK progenitor cell, or an NKT progenitor cell. In some further embodiment, the stem cell, hematopoietic stem or progenitor cell, progenitor, the derived immune cell for modulation, or modulated derived immune cell is genomically engineered, for example, comprising an insertion, a deletion, and/or a nucleic acid replacement. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16.

In some other embodiments of the composition as provided, the isolated population of immune cells may be trans-differentiated from a non-pluripotent cell of hematopoietic or non-hematopoietic lineage. In some embodiments, the isolated population of immune cells may be trans-differentiated from a non-pluripotent cell of hematopoietic or non-hematopoietic lineage prior to, or during, the treatment by the agent.

In some embodiments of the composition as provided, the isolated population of immune cells comprises T cells that have been modulated with a composition comprising (i) at least one of the compounds of Table 1, or salts, esters, ethers, solvates, hydrates, stereoisomers, or prodrugs thereof; (ii) at least a BET inhibitor, an IKK inhibitor, a JAK inhibitor, a PDK1 inhibitor, a Raf inhibitor, or a Syk inhibitor; (iii) at least a PDK1 inhibitor; (iv) at least a Raf inhibitor; (v) at least a Syk inhibitor; (vi) at least one of GSK2334470, AZ628, GDC-0879, Dabrafenib, R788, pacritinib, Bardoxolone methyl, and PRT062607; (vii) at least GSK2334470; (viii) at least Bardoxolone methyl; or (ix) at least AZ628.

In some embodiments of the composition as provided, the isolated population of immune cells comprises T cells. In some embodiments, the isolated population of immune cells comprises CAR-T cells. In some embodiments, the modulated immune cells comprising T cells having at least one of the following properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased central memory T cell subpopulation; (4) decreased effector memory and/or effector T cell subpopulations; (5) improved expansion and viability; and (6) improved capability in tumor clearance and persistence, when compared to T cells not contacted with a composition comprising at least one said modulating agent. In some embodiments, the T cells having at least one of the above properties are CAR-T cells.

Embodiments of the present invention provide a composition comprising an isolated population of T cells having at least one of the following properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased central memory T cell subpopulation; and (4) decreased effector memory and/or effector T cell subpopulations, when compared to T cells without modulation. In some embodiments, the isolated population of T cells in the composition comprises CAR-T cells. In some embodiments, the isolated population of T cells in the composition have improved capability in at least one of: expansion; viability; persistence and tumor clearance.

Aspects of the present invention provide a method of modulating a population of immune cells for adoptive therapies, the method generally comprising contacting the population of immune cells with a sufficient amount of a composition comprising one or more modulating agents selected from the group consisting of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor, for a time sufficient to obtain a population of modulated immune cells having improved therapeutic potential for adoptive cell therapy compared to unmodulated immune cells. In some embodiments, the modulated immune cells for adoptive therapies are autologous. In some embodiments, the modulated immune cells for adoptive therapies are allogenic.

In some embodiments, the composition comprising a sufficient amount of modulating agent comprises (i) at least one of the compounds of Table 1, or salts, esters, ethers, solvates, hydrates, stereoisomers, or prodrugs thereof; (ii) at least a BET inhibitor, an IKK inhibitor, a JAK inhibitor, a PDK1 inhibitor, a Raf inhibitor, or a Syk inhibitor; (iii) at least a PDK1 inhibitor; (iv) at least a Raf inhibitor; (v) at least a Syk inhibitor; (vi) at least one of GSK2334470, AZ628, GDC-0879, Dabrafenib, R788, pacritinib, Bardoxolone methyl, and PRT062607; (vii) at least GSK2334470; (viii) at least Bardoxolone methyl; or (ix) at least AZ628.

In some embodiments of the method, contacting the population of immune cells with the one or more modulating agents improves proliferation, cytotoxicity, cytokine response, cytokine release, cell recall, and/or persistence; and/or improves cell expansion, maintenance, differentiation, de-differentiation, and/or survival rate in comparison to immune cells without the treatment by the one or more of said modulating agents. In some embodiments of the method, contacting the population of immune cells with one or more of said modulating agents increases the number or relative ratio of one or more desired subpopulations of the immune cells in comparison to immune cells without the treatment by the same one or more agents.

In some embodiments, the above method further comprises isolating the one or more desired subpopulations of the immune cells contacted with the one or more of said modulating agents.

In some embodiments, the above method further comprises administering the population or a subpopulation of the treated immune cells, or the isolated one or more desired subpopulations of the treated immune cells, or the therapeutic composition thereof to a subject in need of cell therapy. In some embodiments, the subject has an autoimmune disorder, hematological malignancy, solid tumor, or infection. In some embodiments, the subject had, is under, or will be treated with, chemotherapy or radiation therapy.

In some embodiments, the population of immune cells comprises T cells, NKT cells, or NK cells. In one embodiment of the method, the population of immune cells comprises T cells, and the one or more desired subpopulations after treatment comprise naïve T cells, stem cell memory T cells, and/or central memory T cells. In one embodiment of the method, the population of immune cells comprises NKT cells, and the one or more desired subpopulations after treatment comprise type I NKT cells. In one embodiment of the method, the population of immune cells comprises NK cells, and the one or more desired subpopulations after treatment comprise adaptive NK cells.

In some embodiments of said general method, the immune cells for modulation are isolated from or comprised in peripheral blood, bone marrow, lymph node tissue, cord blood, thymus tissue, tissue from a site of infection, ascites, pleural effusion, spleen tissue, or tumors. In some embodiments, the immune cells for modulation are isolated from a healthy subject; a subject having an autoimmune disease, a hematopoietic malignancy, a virus infection or a solid tumor; a subject previously administered genetically modified immune cells; or a subject that is CMV seropositive. In some other embodiments, the isolated immune cells for modulation are genetically modified (genetically engineered or derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, in some aspects, the genomically modified immune cells are isolated for ex vivo modulation using the present compositions and methods as disclosed. In some embodiments, after modulation, the genomically modified immune cells isolated from a subject may be administered to the same donor or a different patient.

In some embodiments, the immune cells for modulation are differentiated in vitro from stem cells, hematopoietic stem or progenitor cells, or progenitor cells. In some embodiments, the immune cells for modulation are transdifferentiated in vitro from non-pluripotent cells of hematopoietic or non-hematopoietic lineage. In some embodiments, said stem cells comprise induced pluripotent stem cells (iPSCs) or embryonic stem cells (ESCs). In some embodiments, said progenitor cell is a CD34+ hemogenic endothelium cell, a multipotent progenitor cell, a T cell progenitor cell, an NK progenitor cell, or an NKT progenitor cell. In yet some other embodiments, the stem cell, hematopoietic stem or progenitor cell, or progenitor cell is genomically engineered and comprises an insertion, a deletion, or a nucleic acid replacement, and/or comprises at least one genetically modified modality. As such, the desired subpopulation of modulated immune cells derived therefrom comprises immune cells having at least one genetically modified modality.

In some embodiments, said genetically modified modality comprises at least one of the following: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modality comprises one or more deletions or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region. In some other embodiments, the genetically modified modalitiy comprises one or more introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

In some embodiments of the method of modulating immune cells, said "time sufficient" or "sufficient length of time" is no less than 16 hours, 14 hours, 12 hours, 10 hours, 8 hours, 6 hours, 4 hours, 2 hours, 1 hour, 0.5 hour, 0.1 hour, or any length of time in between. As such, said sufficient length of time, for example, is no less than 15, 13, 11, 9, 7, 5, 3, 1, 0.5, or 0.1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, or 90 hour(s).

In some embodiments of said method, the immune cells, during and/or after modulation, are in a feeder-free environment. Feeder-free conditions include feeder cell free, and feeder-conditioned medium free. In some embodiments of said method, the immune cells, during modulation, are co-cultured with feeder cells.

In some embodiments, the subject can be a candidate for adoptive cell transfer. In some embodiments, the subject can be a candidate for bone marrow or stem cell transplantation. In some embodiments, the subject has previously received a bone marrow or stem cell transplantation. In some embodiments, the subject has received bone marrow ablative or non-myeolablative chemotherapy or radiation therapy.

In some embodiments of the method as provided, the population of immune cells comprises T cells. In some embodiments, the population of immune cells comprises CAR-T cells. In some embodiments, the modulated cell population comprises T cells having at least one of the following properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased central memory T cell subpopulation; (4) decreased effector memory and/or effector T cell subpopulations; (5) improved expansion and viability; and (6) improved capability in tumor clearance and persistence, when compared to T cells without modulation with a composition comprising one or more of said modulating agents. In some embodiments, the T cells having at least one of the above properties are CAR-T cells. Aspects of the invention provide a method of manufacturing any of the immune cells having one or more described properties herein.

Aspects of the invention provide a method of making a therapeutic composition for cell therapies according to any of the above methods for modulating a population of immune cells.

Aspects of the present invention provide using the above immune cell modulation methods to make therapeutic compositions comprising modulated immune cells for cell therapies. In some embodiment, the modulated immune cells comprise T, NK and/or NKT cells. In some embodiments, the modulated NK cells comprise adaptive NK cells. An additional aspect of the present invention provides a population of modulated immune cells comprising selectively expanded NK cells made by the method provided herein.

In some embodiments, the present invention provides a therapeutic composition comprising the modulated cells obtained using the methods and composition disclosed herein, and a therapeutically acceptable medium. In some embodiments of the therapeutic composition, the composition further comprises one of more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest, antibodies, chemotherapeutic agents or radioactive moiety, and immunomodulatory drugs (IMiDs).

In some embodiments, provided is a method of treating a subject by administering a therapeutically sufficient amount of the above said therapeutic composition to a subject in need of an adoptive cell therapy. In some embodiments, the cell therapy is autologous. In some other embodiments, the cell therapy is allogeneic. In some embodiments, the subject in need of the therapy has an autoimmune disorder, a hematological malignancy, a solid tumor, cancer, or an infection associated with HIV, RSV, EBV, CMV, adenovirus, or BK polyomavirus. In some embodiments, the method of treating a subject using the modulated immune cells is carried out by administering said therapeutic composition in combination with an antibody, a chemotherapeutic, or a radioactive treatment, wherein the antibody, chemotherapeutic, or radioactive treatment is prior to, concurrent with or after administering the therapeutic composition.

In some aspects, provided are uses of a mixture for manufacturing of a therapeutic composition for cell therapies, wherein the mixture comprises: (a) an isolated population of immune cells, and (b) a composition comprising one or more modulating agents selected from the group consisting of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor. In some embodiments, the one or more modulating agents comprise (i) at least one of the compounds of Table 1, and salts, esters, ethers, solvates, hydrates, stereoisomers, or prodrugs thereof; (ii) at least a BET inhibitor, an IKK inhibitor, a JAK inhibitor, a PDK1 inhibitor, a Raf inhibitor, or a Syk inhibitor; (iii) at least a PDK1 inhibitor; (iv) at least a Raf inhibitor; (v) at least a Syk inhibitor; (vi) at least one of GSK2334470, AZ628, GDC-0879, Dabrafenib, R788, pacritinib, Bardoxolone methyl, and PRT062607; (vii) at least GSK2334470; (viii) at least Bardoxolone methyl; or (ix) at least AZ628. As provided, in some embodiments the mixture for manufacturing a therapeutic composition for cell therapies comprises an isolated population of T cells. In some embodiments, the T cells are CAR-T cells.

In some embodiments, after contacting one or more of said modulating agents, the immune cells comprises modulated T cells that have at least one of the following properties: (1) increased gene expression in at least one of CD27, CCR7, CD62L, TCF7, LEF1, BLIMP-1, ALDOC, and ENO2; (2) decreased gene expression in at least one of PD-1 and Tim-3; (3) increased central memory T cell subpopulation; (4) decreased effector memory and/or effector T cell subpopulations; (5) improved expansion and viability; and (6) improved capability in tumor clearance and persistence, when compared to T cells without being modulated.

Various objects and advantages of this use will become apparent from the following description taken in conjunction with the accompanying drawings wherein are set forth, by way of illustration and example, certain embodiments of this invention.

BRIEF DESCRIPTION OF THE DRAWINGS

FIGS. 8A-C show compound evaluation summary regarding all examined aspects relating to therapeutic application of the treated T cells.

FIGS. 13A-E: (A) schematic of a two-stage tumor clearance and control model; (B) primary tumor control by CAR-T cells treated with DMSO, PI3K inhibitor, or PDK1 inhibitor in comparison to mice without CAR-T cell injection; (C) PDK1 inhibitor treated CAR-T cells displayed significantly (p=0.0061, 1-way ANOVA with Kruskal-Wallis correction) greater in vivo efficacy at day 11 post primary tumor injection, compared to DMSO treated CAR-T cells; (D) PDK1 inhibitor treated CAR-T cells demonstrated rapid control of secondary tumor; (E) the secondary tumor burden was significantly (p=0.0379) less within mice receiving PDK1 treated CAR-T cells compared to mice receiving PI3K treated CAR-T cells.

DETAILED DESCRIPTION OF THE INVENTION

Figure 1A:
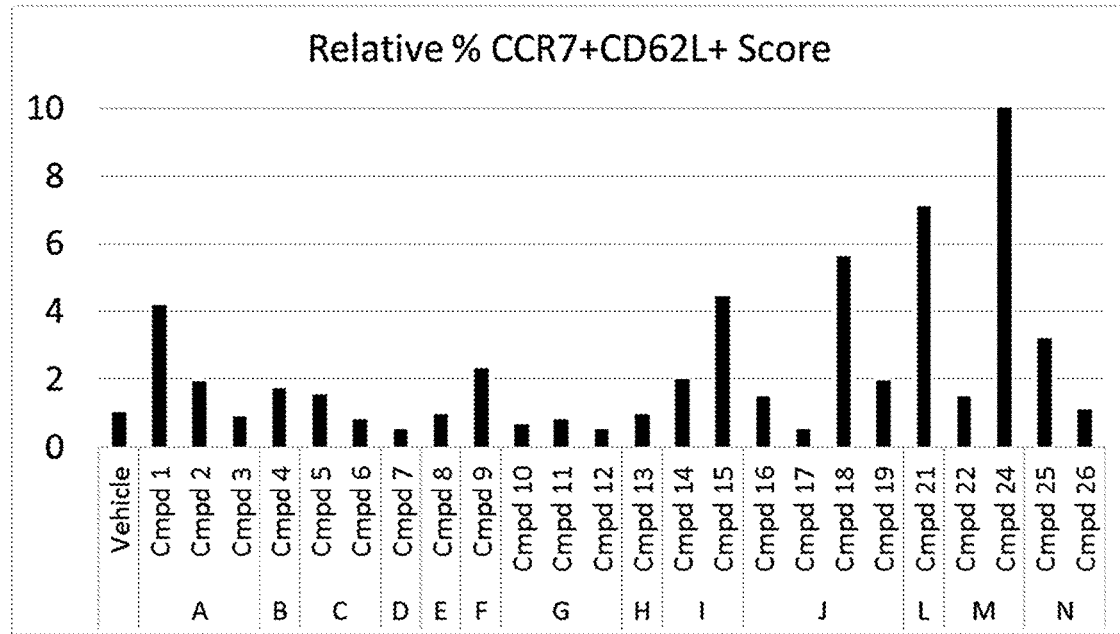
FIGS. 1A-D show that treatment using selected compounds impacts expression of markers that define T cell subsets: (A) relative % CCR7+CD62L+ score; (B) relative CD27 MFI score; (C) Tcm Mini Panel marker gene score; and (D) relative Tim-3 MFI (Inverse) score (refer to Table 1 for compound number and compound category).

The in vivo efficacy of T cell therapy can be strongly influenced by the manufacturing process, which is dependent upon both the starting population of T cells going into the process or feedstock, and the ex vivo expansion and activation methods utilized. The differentiation state of the administered T cells can significantly affect in vivo persistence and anti-tumor activity. T helper (CD4+ T cells) and cytotoxic T cells (CD8+), specifically, naïve (Tn), stem cell memory (Tscm) and central memory (Tcm) T cells, characterized by the expression of the CCR7 and CD62L markers, mediate superior anti-tumor activity in both mouse models (Sommermeyer et al. 2015) and in nonhuman primate models (Berger et al. 2008).

During the manufacturing process, therapeutic cells (or cell populations) are typically activated, optionally transduced or otherwise engineered to express a recombinant receptor, and expanded. This process generally drives differentiation of the cells and leads to an increase in the proportion of the cells in a more differentiated state—in the case of T-cells, the more differentiated cells are phenotypically characterized as effector memory or effector T cells. Once infused into patients, these more differentiated cells have a lower capacity to proliferate and a lower potential to persist as a long-lived or persistent population, as compared to cells in less differentiated states.

Moreover, since the final state of the cells, or specifically, the cell subtypes, going into the patient can be defined in large part by the manufacturing process, the importance of that process cannot be overstated. Preferentially maintaining or expanding cell subpopulations having a desired differentiation state, and/or adaptive immune cell characteristics during cell culture and expansion could be extremely beneficial for enhancing the efficacy of cell-based therapies. Improved cell manufacturing processes have multiple potential advantages including decreased time to dose, increased cellular uniformity, or an increased percentage of patients that reach the desired dose. In addition, functional improvements to the cells during the manufacturing process such as increased persistence and reduced toxicities may also lead to improved cell therapies.

Provided herein are compositions and methods of modulating immune cells to obtain a population or a subpopulation of cells having improved therapeutic potential for adoptive immunotherapies. Also provided are compositions comprising the modulated immune cells having improved therapeutic potential. Also provided are methods of using the modulated immune cells having improved therapeutic potential for treating diseases and conditions. In some embodiments, immune cells having improved therapeutic potential exhibit at least one, or at least two or at least three or more of the following: improved expansion, viability, persistence, cytotoxicity, and/or cell recall/memory. Also provided are methods and compositions for improving immune cell therapeutic potential by increasing the number or relative ratio of or enriching for a subpopulation of cells displaying at least one of the above qualities, such as in the therapeutic cell composition.

Definition

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" refer to one or to more than one of the grammatical object of the article. By way of example, a T cell means one T cell or more than one T cells.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), a T cell present among peripheral blood mononuclear cells (PBMCs), peripheral blood leukocytes (PBLs), a T cell that is among tumor infiltrating lymphocytes (TILs), memory T cells, naïve T cells, regulatory T cells, gamma delta T cells (γδ T cells). Additional types of helper T cells include cells such as Th3, Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

As used herein, the term "naïve T cell" or Tn, refers to mature T cells that, unlike activated or memory T cells, have not encountered their cognate antigen within the periphery. Naïve T cells are commonly characterized by the surface expression of L-selectin (CD62L); the absence of the activation markers CD25, CD44 or CD69; and the absence of the memory CD45RO isoform. They also express functional IL-7 receptors, consisting of subunits IL-7 receptor-α, CD127, and common-γ chain, CD132. In the naïve state, T cells are thought to be quiescent and non-dividing, requiring the common-gamma chain cytokines IL-7 and IL-15 for homeostatic survival mechanisms.

As used herein, the term "central memory T cells" or Tcm, refers to a subgroup or subpopulation of T cells that have lower expression of pro-apoptotic signaling genes, for example, Bid, Bnip3 and Bad, and have higher expression of genes associated with trafficking to secondary lymphoid organs, which genes include CD62L, CXCR3, CCR7, in comparison to effector memory T cells, or Tem.

As used herein, the term "stem memory T cells," or "stem cell memory T cells", or Tscm, refers to a subgroup or subpopulation of T cells that are capable of self-renewing and generating Tcm, Tem and Teff (effector T cells), and express CD27 and lymphoid homing molecules such as CCR7 and CD62L, which are properties important for mediating long-term immunity.

As used herein, the term "NK cell" or "Natural Killer cell" refer to a subset of peripheral blood lymphocytes defined by the expression of CD56 or CD16 and the absence of the T cell receptor (CD3).

As used herein, the terms "adaptive NK cell" and "memory NK cell" are interchangeable and refer to a subset of NK cells that are phenotypically CD3− and CD56+, expressing and have at least one of CD57+, NKG2C and CD57, and optionally, CD16, but lack expression of one or more of the following: +, low PLZF, low SYK, FceRγ, and low FcεRγ, low EAT-2, low TIGIT, low PD1, low CD7, low CD161, high LILRB1, high CD45RO, and low CD45RA. In some embodiments, isolated subpopulations of CD56+NK cells comprise expression of NKG2C and CD57. In some other embodiments, isolated subpopulations of CD56+ NK cells comprise expression of CD57, CD16, NKG2C, CD57, NKG2D, NCR ligands, NKp30, NKp40, NKp46, activating and inhibitory KIRs, NKG2A and/or DNAM-1. CD56+ can be dim or bright expression.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are recognized. Invariant or type I NKT cells express a very limited TCR repertoire—a canonical α-chain (Vα24-Jα18 in humans) associated with a limited spectrum of β chains (Vβ11 in humans). The second population of NKT cells, called nonclassical or noninvariant type II NKT cells, display a more heterogeneous TCR αβ usage. Type I NKT cells are considered suitable for immunotherapy. Adaptive or invariant (type I) NKT cells can be identified with the expression of at least one or more of the following markers, TCR Va24-Ja18, Vb11, CD1d, CD3, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, isolated from a tissue or biopsy sample. The term also includes a cell that is removed from at least one, some or all components as the cell is found in non-naturally occurring environments, for example, isolated from a cell culture or cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cell compositions, substantially pure cell compositions and cells cultured in a medium that is non-naturally occurring. Isolated cells may be obtained from separating the desired cells, or populations thereof, from other substances or cells in the environment, or from removing one or more other cell populations or subpopulations from the environment.

As used herein, the term "purify" or the like refers to increasing purity. For example, the purity can be increased to at least 50%, 60%, 70%, 80%, 90%, 95%, 99%, or 100%.

As used herein, the term "population" when used with reference to T, NK or NKT cells refers to a group of cells including two or more T, NK, or NKT cells, respectively. Using T cell as an example, the isolated, or enriched, population of T cells may include only one type of T cell, or may include a mixture of two or more types of T cell. The isolated population of T cells can be a homogeneous population of one type of T cell or a heterogeneous population of two or more types of T cell. The isolated population of T cells can also be a heterogeneous population having T cells and at least a cell other than a T cell, e.g., a B cell, a macrophage, a neutrophil, an erythrocyte, a hepatocyte, an endothelial cell, an epithelial cell, a muscle cell, a brain cell, etc. The heterogeneous population can have from 0.01% to about 100% T cell. Accordingly, an isolated population of T cells can have at least 50%, 60%, 70%, 80%, 90%, 95%, 98%, or 99% T cells. The isolated population of T cells can include one or more, or all of, the different types of T cells, including but not limited to those disclosed herein. In an isolated population of T cells that includes more than one type of T cells, the relative ratio of each type of T cell can range from 0.01% to 99.99%. The isolated population also can be a clonal population of T cells, in which all the T cells of the population are clones of a single T cell.

An isolated population of T, NK or NKT cells may be obtained from a natural source, such as human peripheral blood or cord blood. Various ways of dissociating cells from tissues or cell mixtures to separate the various cell types have been developed in the art. In some cases, these manipulations result in a relatively homogeneous population of cells. The T cells can be isolated by a sorting or selection process as described herein or by other methods known in the art. The proportion of T cells in the isolated population may be higher than the proportion of T cells in the natural source by at least about 10%, about 20%, about 30%, about 40%, about 50%, about 60%, about 70%, about 80%, about 85%, about 90%, or about 95%. The isolated population of T cells can be for T cells in general, or one or more specific types of T cells.

As used herein, the term "subpopulation" when used in reference to T, NK or NKT cells refers to a population of T, NK or NKT cells that includes less than all types of T, NK, or NKT cells, respectively, that are found in nature.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, "iPSCs," refers to stem cells produced from differentiated adult cells that have been induced or changed (i.e. reprogrammed) into cells capable of differentiating into tissues of all three germ or dermal layers: mesoderm, endoderm, and ectoderm.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta and are not totipotent.

As used herein, the term "progenitor cell" refers to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" is intended to mean that the referenced molecule or the referenced activity is introduced into, or non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

As used herein, the term "ex vivo" refers to activities that take place outside an organism, such as experimentation or measurements done in or on living tissue in an artificial environment outside the organism, preferably with minimum alteration of the natural conditions. The "ex vivo" procedures can involve living cells or tissues taken from an organism and cultured in a laboratory apparatus, usually under sterile conditions, and typically for a few hours or up to about 24 hours, but including up to 2 to 28 days, depending on the circumstances. Such tissues or cells can also be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo. Meanwhile, an "in vivo" activity takes place in an organism, for example, a mouse, wherein such activities may include cell engraftment, cell homing, self-renewal of cells, and expansion of cells.

As used herein, the term "in vitro" refers to activities performed or taking place in a test tube, culture dish, or elsewhere outside of a living organism.

As used herein, the terms "contact," "treat," or "modulate," when used in reference to an action carried out on an immune cell, are used interchangeably herein to refer to culturing, incubating or exposing an immune cell with one or more of the agents disclosed herein.

As used herein, a "noncontacted" or an "untreated" cell is a cell that has not been treated, e.g., cultured, contacted, or incubated with an agent other than a control or vehicle agent. Cells contacted with a control agent, such as DMSO, or contacted with another vehicle are examples of noncontacted cells.

As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an antimitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

As used herein, the term "analogue" refers to a chemical molecule that is similar to another chemical substance in structure and function, differing structurally by one single element or group, or more than one group (e.g., 2, 3, or 4 groups) if it retains the same chemical scaffold and function as the parental chemical. Such modifications include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), halogen addition, modifications to the level of saturation or unsaturation of side chains, and the addition of modified groups such as substituted phenyl and phenoxy. Analogues can also include conjugates, such as biotin or avidin moieties, enzymes such as horseradish peroxidase, and including radio-labeled, bioluminescent, chemiluminescent, or fluorescent moieties. Also, moieties can be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.).

As used herein, the term "increase" refers to the ability of an agent to produce or cause a greater physiological response (i.e., downstream effects) in a cell, as compared to the response caused by either vehicle or a control molecule/composition, e.g., increased production of interleukin 2 or TNF by an isolated population of T cells. The increase can be an increase in gene expression as a result of increased signaling through certain cell signaling pathways. An "increased" amount is typically a statistically significant amount, and can include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) compared to the response produced by vehicle (the absence of an agent) or a control composition.

As used herein, the term "decrease" refers to the ability of an agent to produce or cause a lesser physiological response (i.e., downstream effects) in a cell, as compared to the response caused by either vehicle or a control molecule/composition. The decrease can be a decrease in gene expression, a decrease in cell signaling, or a decrease in cell proliferation. A "decreased" amount is typically a statistically significant amount, and can include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the term "synergy" or "synergistic" refers to a combination of two or more entities for an enhanced effect such that the working together of the two or more entities produces an effect greater than the sum of their individual effects, as compared to "antagonistic," which is used when two or more entities in a combination counteract or neutralize each other's effect; and compared to "additive," which is used when two or more entities in a combination produce an effect nearly equal to the sum of their individual effects.

As used herein, the terms "substantially free of," when used to describe a composition, such as a cell population or culture media, refers to a composition that is free of a specified substance of any source, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. The range of quantity, level, value, number, frequency, percentage, dimension, size, amount, weight or length can be ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "subject," refers to a mammal. A subject can be a human or a non-human mammal such as a dog, cat, bovid, equine, mouse, rat, rabbit, or transgenic species thereof.

As used herein, the terms "treat," "treatment" "treated" and "treating", when used in reference to a subject in need of a therapeutic composition or method, refer to obtaining a desired pharmacologic and/or physiologic effect, including without limitation achieving an improvement or elimination or amelioration or preventing of one or more signs or symptoms of a disease. The effect can be prophylactic and/or can involve completely or partially preventing a disease or symptom thereof and/or can be therapeutic in terms of achieving an improvement or elimination of symptoms, or providing a partial or complete cure for a disease and/or adverse effect attributable to the disease. The term "treatment" includes any treatment of a disease in a mammal, particularly in a human, and includes in some embodiments: (a) preventing the disease from occurring in a subject which can be predisposed to the disease but has not yet been diagnosed as having it; (b) inhibiting the disease, or arresting its development; (c) relieving the disease, or causing regression of the disease, or completely or partially eliminating symptoms of the disease; and (d) restoring the individual to a pre-disease state, such as reconstituting the hematopoietic system.

As used herein, "genetic modification" may refer to genetic editing and can include modifications (1) derived from naturally-arising rearrangements, mutations, genetic imprinting and/or epigenetic modification, or (2) obtained through genomic engineering through insertion, deletion or substitution in the genome of a cell. Genetic modification, as used herein, can also include one or more retainable therapeutic attributes of a source-specific immune cell that is donor-, disease-, or treatment response-specific.

As used herein, the term "genetic imprint" refers to genetic or epigenetic information that contributes to preferential therapeutic attributes in a source cell. In the aspect of a source cell obtained from a specifically selected donor, disease or treatment context, the genetic imprint contributing to preferential therapeutic attributes may include any context-specific genetic or epigenetic modifications which manifest a retainable phenotype, i.e. a preferential therapeutic attribute, irrespective of the underlying molecular events being identified or not. Donor-, disease-, or treatment response-specific source cells may comprise genetic imprints that are retainable in iPSCs and derived hematopoietic lineage cells. Such genetic imprints include but are not limited to, a monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a common haplotype. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to the immunosuppressive effects of the tumor microenvironment; induction of bystander immune cells and desirable immune modulation; improved on-target specificity with reduced off-tumor effect; and resistance to treatment such as chemotherapy.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis or DNA replication, growth arrest, transcriptional and post-transcriptional genetic regulation and/or antibody-mediated depletion. In some instances, the safety switch protein is activated by an exogenous molecule, e.g. a prodrug, that, when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

A "therapeutically sufficient amount", as used herein, includes within its meaning sufficient and/or effective amount of the particular therapeutic and/or pharmaceutical composition to which it is referring to provide a desired therapeutic effect. The exact amount may vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

I. Modulating Agents for Improving Efficacy of Cell-Based Adoptive Immunotherapy The present invention in some embodiments provides a composition comprising one or more modulating agents in an amount sufficient for improving one or more properties, such as therapeutic potential, of immune cells such as modulated immune cells suitable for adoptive cell-based therapies. In some aspects, immune cells having improved therapeutic potential present improved proliferation, persistence, cytotoxicity, and/or cell recall/memory, as compared to cells produced or maintained under conditions, such as similar conditions, not including the one or more modulating agents. In some embodiments, by way of modulation of the immune cells using the agents or composition comprising the modulating agents, the immune cells obtained comprise one or more such improvement, such as an improvement in at least one attribute. In some aspects the at least one attribute includes, but is not limited to and/or includes at least one or more of: phenotype skewing (for example, from Teff or Tem to Tn, Tcm, and/or Tscm and/or an increased relative number of naïve, central memory and/or stem central memory T cells as compared to one or more other T cell subpopulations); increased cell expansion, increased cell viability; and/or enhanced capability in tumor clearance and persistence. In some embodiments, immune cells such as those suitable for adoptive cell-based therapies are contacted, treated, or modulated with one or more classes of modulating agents categorized by their respective targets. In some embodiments, cells are engineered through a process at least one or more steps of which is carried out in the presence of the composition or modulating agent or agents. As provided, the classes of modulating agents capable of improving therapeutic potential of an immune cell in at least one biological property include BET inhibitors, CDK inhibitors, CRAC channel inhibitors, Cox inhibitors, dopamine antagonists, ERK5 inhibitors, glucocorticoids, IGF-1R inhibitors, IKK inhibitors, JAK inhibitors, Lck inhibitors, PDK1 inhibitors, Raf inhibitors, and Syk inhibitors. For each provided class of modulating agents, some unlimiting and exemplary compounds are listed in Table 1.

As used interchangeably herein, "modulators" or "modulating agents" are used to refer to inhibitory or activating agents that possess the ability to regulate the expression or activity of a particular target (such as a protein or encoding polynucleotide). "Modulators" or "modulating agents" include inhibitors and activators, e.g., ligands, agonists, antagonists. A modulating agent, or a modulator, as used herein may be an organic compound (e.g., small chemical molecules), a polypeptide (e.g., a peptide or an antibody), a nucleic acid (e.g., DNA, RNA, double-stranded, single-stranded, an oligonucleotide, antisense RNA, small inhibitory RNA, micro RNA, a ribozyme, etc.), an oligosaccharide, or a lipid; or their similarly functioning (e.g. inhibition or activation towards the same target) homologs, mimetics, derivatives, analogues or salts, whether synthetic or naturally occurring.

Inhibitors are agents that may, e.g., decrease or eliminate the expression of a described target protein or other target; or partially or totally block stimulation or protease inhibitor activity of the target protein; or decrease, prevent, delay activation, inactivate, desensitize, or down regulate the activity of the target protein, e.g., antagonists. Activators are agents that may, e.g., induce or activate the expression of a described target protein, or stimulate, increase, activate, facilitate, enhance activation or protease inhibitor activity, sensitize or up regulate the activity of described target protein, e.g., agonists. Assays for inhibitors and activators include, e.g., applying putative modulator agents to cells expressing the described target protein and then determining the functional effects and extent of the effect on the described target protein expression and/or activity. Generally, control samples (untreated with modulators or treated with vehicle alone) are assigned a specific activity value of 100%. Inhibition of a described target protein is achieved when the activity value relative to the control is about 90%, optionally 80%, 70%, 60%, 50%, 25%, 10%, 5% or 1% or lower. Activation of the described target protein is achieved when the activity value relative to the control is 110%, optionally 150%, 200%, 300%, 400%, 500%, or 1000-3000% or higher.

To improve immune cell therapeutic potential generally involves certain improvements in the quality of the immune cells. Treatment with modulating agent(s) of some embodiments provided herein is shown herein to enhance certain biological properties of the treated immune cells, for example by modulating at least one of the following or potential for at least one of the following, for example, under or in response to certain conditions, which may be specified: cell phenotype skewing, expansion, maintenance, differentiation, dedifferentiation, survival, proliferation, cytotoxicity, persistence, and/or cell recall/memory, thereby improving the therapeutic potential of the immune cells. In a T cell population, for example, phenotype skewing towards naïve, stem cell memory, or central memory T cells results in an increased number or relative ratio of the naïve, stem cell memory, or central memory T cells subpopulation and/or decreased number or relative ratio effector memory or effector T cell subpopulation through modulating maintenance, expansion, differentiation, and/or de-differentiation thereof, are indicative of better quality of the T cells for improved in vivo adoptive therapeutic potential. In one embodiment, the number or proportion of naïve T cells, stem cell memory T cells, and/or central memory T cells increases in a T cell population upon treatment using one or more of the modulating agents comprising at least one of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor. In one embodiment, the phenotype skewing, or the increase of the number or proportion of naïve T cells, stem cell memory T cells, and/or central memory T cells is indicated by an increased expression of surface markers after the agent treatment. In one embodiment, the phenotype skewing, or the increase of the number or proportion of naïve T cells, stem cell memory T cells, and/or central memory T cells is indicated by the cytokine profile associated with naïve or memory T cells rather than effector cells after the agent treatment.

In some other embodiments, at least one of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor improves therapeutic potential of a T cell by improving the cell's in vitro killing ability.

In yet other embodiments, at least one of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor improves therapeutic potential of a T cell by increasing cell survival and expansion.

In still other embodiments, at least one of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor improves therapeutic potential of a T cell by enhancing the cell's persistence and capability in tumor clearance.

Similarly, in an NK cell population, for example, an increased number or relative ratio of adaptive NK cells through maintenance, subtype skewing, expansion, differentiation, and/or de-differentiation thereof is indicative of better quality of the NK cells for improved in vivo adoptive therapeutic potential. With respect to an NKT cell population, for example, an increased number or relative ratio of type I NKT cells through maintenance, subtype switching, expansion, differentiation, and/or de-differentiation thereof are indicative of better quality of the NKT cells for improved in vivo adoptive therapeutic potential.

The classes of modulating agents categorized/identified by their respective targets in Table 1 were discovered based on their potential to improve the therapeutic potential of an immune cell for adoptive therapy. Without being limited by the theory, they modulate and improve a therapeutic immune cell via regulating cell metabolism, nutrient sensing, proliferation, apoptosis, signal transduction, cytokine production, properties relating to infective process, and/or other aspects of cell function.

TABLE 1

Agents of Interest for Immune Cell Modulation:

| Target/Class Category No. | Target/Class | Exemplary Compound Name | CAS No. | Compound No. |
|---|---|---|---|---|
| A | BET inhibitor | OTX015 | 202590-98-5 | 1 |
|  |  | CPI-203 | 1446144-04-2 | 2 |
|  |  | JQ1 | 1268524-69-1 | 3 |
|  |  |  | 1268524-70-4 |  |
|  |  |  | 1268524-71-5 |  |
| B | CDK inhibitor | PHA-793887 | 718630-59-2 | 4 |
| C | CRAC channel inhibitor | Pyr6 | 79775-19-2 | 5 |
|  |  | BTP 2 | 223499-30-7 | 6 |
| D | Cox inhibitor | Etoricoxib | 202409-33-4 | 7 |
| E | Dopamine antagonist | Sertindole | 106516-24-9 | 8 |

TABLE 1-continued

Agents of Interest for Immune Cell Modulation:

| Target/Class Category No. | Target/Class | Exemplary Compound Name | CAS No. | Compound No. |
|---|---|---|---|---|
| F | ERK5 inhibitor | XMD8-92 | 1234480-50-2 | 9 |
| G | Glucocorticoid | Flunisolide | 3385-03-3 | 10 |
|   |   | Dexamethasone Acetate | 1177-87-3 | 11 |
|   |   | Amcinonide | 51022-69-6 | 12 |
| H | IGF-1R inhibitor | BMS-536924 | 468740-43-4 | 13 |
| I | IKK inhibitor | TPCA-1 | 507475-17-4 | 14 |
|   |   | Bardoxolone Methyl | 218600-53-4 | 15 |
| J | JAK inhibitor | Ruxolitinib | 941678-49-5 | 16 |
|   |   | Pacritinib | 937272-79-2 | 17 |
|   |   | Tofacitinib | 477600-75-2 | 18 |
|   |   | CEP33779 | 1257704-57-6 | 19 |
| K | Lck inhibitor | KIN001-051 | 213743-31-8 | 20 |
| L | PDK-1 inhibitor | GSK2334470 | 1227911-45-6 | 21 |
| M | Raf inhibitor | GDC-0879 | 905281-76-7 | 22 |
|   |   | AZ628 | 878739-06-1 | 23 |
|   |   | Dabrafenib | Dabrafenib | 24 |
| N | Syk inhibitor | R788 | 901119-35-5 | 25 |
|   |   | PRT062607 | 1370261-97-4 | 26 |

The term "BET inhibitor" refers to an agent that inhibits at least one activity of an BET (Bromodomain and Extra-Terminal motif) protein. BET proteins, containing bromodomains that bind to acetylated lysine residues, have been implicated in nucleosome remodeling and transcription regulation through their ability to regulate lysine acetylation at, for example, histones. In one embodiment, a BET inhibitor binds the bromodomain of a BET protein. In one embodiment, a BET inhibitor prevents protein-protein interaction between the BET protein and an acetylated histone or a transcription factor. In one embodiment, a BET inhibitor inhibits all or part of the activity of at least one of BRD2, BRD3, BRD4 and BRDT protein or any combinations thereof. In one embodiment, the BET inhibitor is a small chemical molecule. In one embodiment, the BET inhibitor is an antibody. In another embodiment, the BET inhibitor is a small RNA (antisense RNA, siRNA, miRNA). In some embodiments, the BET inhibitors include, but are not limited to, OTX015, CPI-203, JQ1, GSK1210151A, GSK525762, TEN-010, CPI-0610, olinone, RVX-208, PF-6405761, I-BET-762, GSK6853, EED226, Mivebresib, CPI-637, BI-9564, BI-7273, GSK602, PF-CBP1 HCl, SGC-CBP30, Bromosporine, UNC669, MS436, PFI-3, PFI-4, GSK2801, GSK1324726A, OF-1, UNC1215, and their derivatives or analogues. In one embodiment, the BET inhibitor for immune cell modulation comprises OTX015. In another embodiment, the BET inhibitor for immune cell modulation comprises CPI-203. In yet another embodiment, the BET inhibitor for immune cell modulation comprises JQ1.

The term "CDK inhibitor" refers to an agent that inhibits at least one activity of a cyclin-dependent kinase (CDK). CDKs are a family of serine-threonine protein kinases that are activated by binding cyclin and play a role in regulating cell cycle, transcription, mRNA processing, and cell differentiation. The activity of CDKs depends on their association with cyclins and their downstream effects require additional protein-protein interactions. In one embodiment, a CDK inhibitor inhibits the binding of a cyclin to a CDK or the binding of the CDK:cyclin protein to additional interacting proteins. In another embodiment, a CDK inhibitor inhibits the kinase function of a CDK by, for example, acting as a competitive or non-competitive ATP binding site inhibitor, as an allosteric inhibitor; or as a covalent inhibitor. In one embodiment, the CDK inhibitor is a small chemical molecule. In one embodiment, the CDK inhibitor is an antibody. In another embodiment, the CDK inhibitor is a small RNA (antisense RNA, siRNA, miRNA). In some embodiments, the CDK inhibitors include, but are not limited to, PHA-793887, PHA-767491, PHA-848125 (Milciclib), PD-0332991 (Palbociclib), Palbociclib Isethionate, CYC202 (Roscovitine), SNS-032, SCH727965 (Dinaciclib), Flavopiridol, Flavopiridol HCl, AT7519, JNJ-7706621, AZD5438, AZD5438, AZD5438, LY2835219 (abemaciclib), BMS-265246, R547, Ribociclib (LEE011), NU6027, P276-00, Kenpaullone, AT7519 HCl, LDC000067, THZ1, SU 9516, K03861, XL413 (BMS-863233), LY2857785, RO-3306, ON123300, LDC4297, Purvalanol A, ML167, TG003, and their derivatives or analogues. In one embodiment, the CDK inhibitor for immune cell modulation comprises PHA-793887.

CRAC (Ca2+ release-activated Ca2+) channel inhibitor (also called CRAC channel Ca entry blocker) disrupts the movement of calcium by preventing the opening of CRAC channels. The term "CRAC channel Ca entry blocker" refers to an agent that inhibits at least one activity of a CRAC channel. CRAC channels are a 2-component complex involving the STIM (ER Ca2+ sensor) and Orai (pore-forming sub-unit) proteins. When calcium ions (Ca2+) are depleted from the endoplasmic reticulum (ER) of mammalian cells, STIM oligomerizes, and interacts with and gates Orai to activate CRAC channels allowing Ca2+ replenishment in the ER. Ca2+ influx through CRAC channels is an important downstream event after T cell receptor activation required for cytokine production. In one embodiment, a CRAC channel inhibitor prevents the activation of a CRAC channel. In one embodiment, a CRAC channel inhibitor prevents at least one activity of a STIM protein. In one embodiment, a CRAC channel inhibitor prevents at least one activity of an Orai protein. In one embodiment, a CRAC channel inhibitor impedes the oligomerization of STIM. In one embodiment, a CRAC channel inhibitor blocks the STIM interaction with Orai. In one embodiment, a CRAC channel inhibitor prevents STIM from conformational unfolding and keeps STIM inactivated. In another embodiment, a CRAC channel inhibitor prevents Ca2+ from binding to Orai. In one embodiment, the STIM comprise STIM1 or STIM2. In one embodiment, the Orai comprises Orai1, Orai2 or Orai3. In one embodiment, the CRAC channel inhibitor is a small chemical molecule. In one embodiment, the CRAC channel inhibitor is an antibody. In another embodiment, the CRAC channel inhibitor is a small RNA (antisense RNA, siRNA, miRNA). In some embodiments, the CRAC channel inhibitors include, but are not limited to, pyrazole derivatives (BTP1, BTP2, BTP3, GSK7975A, GSK5503A), lanthanides, 2-APB, DPB162-AE, DPB163-AE, imidazole compounds (SKF-96365), Synta66, R02959, CM2489, CM3457, ML-9, and their derivatives or analogues. In one embodiment, the CRAC channel inhibitor for immune cell modulation comprises BTP2.

The term "Cox inhibitor" refers to an agent that inhibits at least one activity of a cyclooxygenase (COX). Cyclooxygenases are a family of isozymes responsible for formation of prostanoids, including thromboxane and prostaglandins such as prostacyclin. In one embodiment, a COX inhibitor inhibits activity of COX-1. In another embodiment, a COX inhibitor inhibits activity of COX-2. In yet another embodiment, a COX inhibitor inhibits both COX-1 and COX-2. In one embodiment, the COX inhibitor is a small chemical molecule. In one embodiment, the COX inhibitor is an antibody. In another embodiment, the COX inhibitor is a small RNA (antisense RNA, siRNA, miRNA). In some embodiments, the COX inhibitors include, but are not limited to, Etoricoxib, Celecoxib, Rofecoxib, Meloxicam, Valdecoxib, Naproxen, Diclofenac, Licofelone, Etodolac, Ketorolac, Flufenamic acid, Bufexamac, Piroxicam, and their derivatives or analogues. In one embodiment, the cyclooxygenase inhibitor for immune cell modulation comprises Etoricoxib.

The term "dopamine antagonist" refers to an agent that inhibits at least one activity of a dopamine receptor. Dopamine receptors are G protein-coupled receptors (GPCRs), whose signaling is primarily mediated by interaction with and activation of heterotrimeric GTP-binding proteins (G proteins). In addition, receptor oligomerization or receptor interactions with scaffolding and signal-switching proteins are important for the regulation of dopamine receptor signaling. In one embodiment, a dopamine antagonist binds to a dopamine receptor thereby blocking the receptor from recognizing and/or interacting with an effector molecule that contributes to the triggering of downstream responses including, but not limited to ion channels, phospholipases, protein kinases, and receptor tyrosine kinases. In one embodiment, the dopamine antagonist is a small chemical molecule. In one embodiment, the dopamine antagonist is an antibody. In another embodiment, the dopamine antagonist is a small RNA (antisense RNA, siRNA, miRNA). In some embodiments, the dopamine antagonists include, but are not limited to, Sertindole, Clebopride malate, Azaperone, Fluphenazine dihydrochloride, Amisulpride, Paliperidone, Amisulpride Hcl, Bromopride, and their derivatives or analogues. In one embodiment, the dopamine antagonist for immune cell modulation comprises Sertindole.

The term "ERK5/BMK1 inhibitor" or "ERK5 inhibitor" refers to an agent that inhibits at least one activity of ERK5 (extracellular signal regulated kinase 5), also known as big MAPK 1 (BMK1). ERK5 is a member of the MAPK family. ERK5 can be activated by growth factors, cytokines and stress and requires phosphorylation by MAPK kinase 5 (MEK5) for full activity. The ERK5 pathway plays an important role in regulating cell proliferation and differentiation through regulation of downstream transcription factors by phosphorylation. In one embodiment, the inhibitory agent of ERK5 prevents phosphorylation of ERK5. In one embodiment, the inhibitory agent of ERK5 prevents ERK5 dimerization. In another embodiment, the inhibitory agent of ERK5 disrupts ERK5 transactivation. In yet another embodiment, the inhibitory agent of ERK5 inhibits MEK5 activation. In one embodiment, the ERK5 inhibitor is a small chemical molecule. In one embodiment, the ERK5 inhibitor is an antibody. In another embodiment, the ERK5 inhibitor is a small RNA (antisense RNA, siRNA, miRNA). In some embodiments, the ERK5 inhibitors include, but are not limited to, XMD8-92, DEL-22379, indolinone-6-carboxamides (BIX02188, BIX02189), U0126, PD98059, and their derivatives or analogues. In one embodiment, the ERK5 inhibitor for immune cell modulation comprises XMD8-92.

The term "glucocorticoids" (GCs) refers to a class of steroid hormones that bind to and activate the glucocorticoid receptor (GR). The activated GR complex, in turn, regulates transcription through directly binding to glucocorticoid response elements within the promoters of target genes or by trans-repression through interaction with promoter-bound transcriptional complexes. GR plays a key role in many physiologically important processes. These include gluconeogenesis, glucose uptake in muscle and fat breakdown in adipose tissue. In addition, GCs, acting through the GR, exert potent immunosuppressive and anti-inflammatory effects due to their role in the development and homeostasis of T lymphocytes. GCs are part of the feedback mechanism in the immune system which reduces certain aspects of immune function. Exemplary glucocorticoids that activate GR (GR agonist) include, but are not limited to, Dexamethasone acetate, Amcinonide, Flunisolide, Beclometasone, Cortodoxone, Prednisolone, Fluticasone propionate, Mometasone furoate, Betamethasone, Beclometasone dipropionate, and their derivatives or analogues. In one embodiment, the glucocorticoid used for immune cell modulation comprises Flunisolide. In one embodiment, the glucocorticoid used for immune cell modulation comprises Dexamethasone acetate. In another embodiment, the glucocorticoid used for immune cell modulation comprises Amcinonide.

The term "IGF-1R inhibitor" refers to an agent that inhibits at least one activity of a Type I insulin-like growth factor receptor (IGF-1R). IGF-1R is a receptor tyrosine kinase composed of 2 alpha chains and 2 beta chains that are initially translated as a single polypeptide. The alpha chains are responsible for ligand binding and the beta chains include both the transmembrane and kinase domains. IGF-1R is activated by IGF-1 (insulin-like growth factor 1) and IGF-2. In response to ligand binding, the a chains of IGF-1R induce the tyrosine autophosphorylation of the β chains, which event triggers a cascade of intracellular signaling that promotes cell survival and cell proliferation. In one embodiment, an IGF-1R inhibitor prevents IGF-1R from binding to IGF-1 or IGF-2. In one embodiment, an IGF-1R inhibitor prevents IGF-1R β chain mediated kinase activity. In one embodiment, the IGF-1R inhibitor is a small chemical molecule. In one embodiment, the IGF-1R inhibitor is an antibody. In another embodiment, the IGF-1R inhibitor is a small RNA (antisense RNA, siRNA, miRNA). In some embodiments, the IGF-1R inhibitors include, but are not limited to, BMS-536924, Linsitinib, NVP-AEW541, GSK1904529A, NVP-ADW742, NT157, Tyrphostin, GSK1838705A, BMS-754807, PQ401, Picropodophyllin, and their derivatives or analogues. In one embodiment, the IGF-1R inhibitor for immune cell modulation comprises BMS-536924.

The term "IKK inhibitor" refers to an agent that inhibits at least one activity of IKK (inhibitor of nuclear factor κB kinase). IKK is an enzyme complex composed of IKK1, IKK2 and NEMO, and it phosphorylates the inhibitory IκBα protein. This phosphorylation results in the dissociation of IκBα from NF-κB. After dissociation, NF-κB migrates into the nucleus and activates the expression of genes involved in immune responses, inflammation and cell survival. Thus, IKK can be considered a master regulator of NF-κB activation. In one embodiment, an IKK inhibitor prevents phosphorylation of IκBα protein. In one embodiment, an IKK inhibitor prevents IKK from transferring a phosphate group to its substrate. In one embodiment, an IKK inhibitor impairs the catalytic function of a subunit of the IKK complex. In another embodiment, an IKK inhibitor reduces the regulatory function of a subunit of the IKK complex. In one embodiment, the IKK inhibitor is a small chemical molecule. In one embodiment, the IKK inhibitor is an antibody. In another embodiment, the IKK inhibitor is a small RNA (antisense RNA, siRNA, miRNA). In some embodiments, the IKK inhibitors include, but are not limited to, TPCA-1, Bardoxolone Methyl, Resveratrol, MLN120B, MRT67307, AmLexanox, BMS-345541, IKK 16, BI605906, ACHP Hydrochloride, PS-1145, Apigenin, SC-514, IKKc-IN-1, IMD-0354, LY2409881, AZD 3264, Icariin (Ieariline), Bay 65-1942 Hcl, Bay 65-1942, and their derivatives or analogues. In one embodiment, the IKK inhibitor for immune cell modulation comprises TPCA-1. In another embodiment, the IKK inhibitor for immune cell modulation comprises Bardoxolone Methyl.

The term "JAK inhibitor" refers to an agent that inhibits at least one activity of a Janus kinase (JAK). Janus kinases are a family of intracellular, nonreceptor tyrosine kinases that transduce cytokine-mediated signals via the JAK-STAT pathway. JAKs (JAK1, 2, 3, and TYK2) phosphorylate and activate downstream proteins involved in Type I and Type II cytokine receptor signal transduction pathways that play a role in the immune responses. For example, JAK1 and JAK2 recruit signal transducers and activators of transcription (STATs) to cytokine receptors. Upon phosphorylation by the JAKs, STATs dimerize and translocate to the nucleus where they bind DNA, and in turn, regulate gene expression. In one embodiment, a JAK inhibitor prevents JAK activation and thus inhibits the tyrosine kinases enzymatic activity. In one embodiment, a JAK inhibitor inhibits at least one Janus kinase. In one embodiment, a JAK inhibitor inhibits JAK1 activation. In one embodiment, a JAK inhibitor inhibits JAK2 activation. In another embodiment, a JAK inhibitor inhibits JAK3 activation. In yet another embodiment, a JAK inhibitor inhibits TYK2 activation. In one embodiment, the JAK inhibitor is a small chemical molecule. In one embodiment, the JAK inhibitor is an antibody. In another embodiment, the JAK inhibitor is a small RNA (antisense RNA, siRNA, miRNA). In some embodiments, the JAK inhibitors include, but are not limited to, Ruxolitinib, Pacritinib, Tofacitinib, CEP33779, Tasocitinib, Tofacitinib (CP-690550) Citrate, AZD1480, Fedratinib, AT9283, AG-490 (Tyrphostin B42), Momelotinib (CYT387), TG101209, WP1066, Gandotinib, NVP-BSK805 2HC1, Baricitinib, AZ 960, WHI-P154, XL019, ZM 39923 HCl, FLLL32, VX-509, and their derivatives or analogues. In one embodiment, the JAK inhibitor for immune cell modulation comprises Ruxolitinib. In one embodiment, the JAK inhibitor for immune cell modulation comprises Pacritinib. In another embodiment, the JAK inhibitor for immune cell modulation comprises Tofacitinib. In another embodiment, the JAK inhibitor for immune cell modulation comprises CEP33779.

The term "Lck inhibitor" refers to an agent that inhibits at least one activity of lymphocyte-specific protein tyrosine kinase (Lck). Lck, belonging to the Src family of tyrosine kinases, is expressed in T cells and natural killer (NK) cells and is a key component for the activation of and signaling through the T-cell receptor. Activation of this cascade results in the up regulation of inflammatory cytokines such as IL-2 and interferon (IFN)-γ. In one embodiment, the Lck inhibitor is a small chemical molecule. In one embodiment, the Lck inhibitor is an antibody. In another embodiment, the Lck inhibitor is a small RNA (antisense RNA, siRNA, miRNA). In some embodiments, the Lck inhibitors include, but are not limited to, KIN001-051, RK-24466, (7-Cyclopentyl-5-(4-phenoxyphenyl)-7H-pyrrolo[2,3-d]pyrimidin-4-amine), anilinopyrimidine, 2,3-diarylfuropyrimidines, benzimidazole-substituted anilinepyrimidines, pyrimidopyrazine derivative, 2-amino-6-carboxamidobenzothaizoles, BMS-354825, BMS-350751, BMS-358233, 2-(aminoheteroaryl)-thiazole-5-carbox amide, A-420983, Pyrrolo [2,3-d] pyrimidines, and their derivatives or analogues. In one embodiment, the Lck inhibitor for immune cell modulation comprises KIN001-051.

The term "PDK1 inhibitor" refers to an agent that inhibits at least one activity of Phosphoinositide-dependent kinase 1 (PDK1). PDK1 regulates both pathways associated with the AKT/mTOR and pathways independent of AKT. PDK1 mediated Akt-independent pathways have a main role in controlling cell proliferation, survival and cell motility. Other than AKT, AGC kinases such as protein kinase C (PKC), p70 ribosomal S6 kinase (S6K), serum- and glucocorticoid-regulated kinase (SGK), p90 ribosomal S6 kinase (RSK), and ROCK1 are among the direct downstream targets of PDK1 in these AKT-independent pathways. The mechanisms of AKT-independent PDK1 signaling are also different from that of AKT signaling. Some PDK1 inhibitors inhibit AKT not as potently as other AGC kinases. For example, GSK2334470 inhibits S6K and SGK more potently than inhibiting AKT, leading to mainly an AKT independent PDK1 signaling. In one embodiment, the PDK1 inhibitor is a small chemical molecule. In one embodiment, the PDK1 inhibitor is an antibody. In another embodiment, the PDK1 inhibitor is a small RNA (antisense RNA, siRNA, miRNA). In some embodiments, the PDK1 inhibitors include, but are not limited to, GSK2334470, Celecoxib, Enzastaurin, AR-12, PHT-427, 2,2-Dichloroacetophenone, BX-795, Staurosporine, BX-912, KP372-1, UCN-01, and their derivatives or analogues. In one embodiment, the PDK1 inhibitor for immune cell modulation comprises GSK2334470.

The term "Raf inhibitor" refers to an agent that inhibits at least one activity of Rapidly Accelerated Fibrosarcoma (Raf) kinase. The Rafs are serine/threonine kinases and are activated by interacting with RAS-GTP at the membrane. Activated Raf leads to phosphorylation and activation of MEK1 and MEK2, which activates the effector MAP kinases ERK1 and ERK2 by phosphorylation, a signaling cascade involved in cell proliferation, differentiation, migration and survival. In one embodiment, the Raf inhibitor inhibits Raf kinase's interaction with RAS-GTP. In another embodiment, the Raf inhibitor impairs Raf kinase's enzymatic activity. In one embodiment, the Raf inhibitor is a small chemical molecule. In one embodiment, the Raf inhibitor is an antibody. In another embodiment, the Raf inhibitor is a small RNA (antisense RNA, siRNA, miRNA). In some embodiments, the Raf inhibitors include, but are not limited to, GDC-0879, AZ628, Dabrafenib, Sorafenib, Sorafenib Tosylate, SB590885, ZM 336372, GW5074, TAK-632, MLN2480, LY03009120, and their derivatives or analogues. In one embodiment, the Raf inhibitor for immune cell modulation comprises GDC-0879. In another embodiment, the Raf inhibitor for immune cell modulation comprises AZ628. In another embodiment, the Raf inhibitor for immune cell modulation comprises Dabrafenib.

The term "Syk inhibitor" refers to an agent that inhibits at least one activity of Spleen tyrosine kinase (Syk). Syk is a cytoplasmic protein tyrosine kinase most highly expressed by haemopoietic cells and is a key integrator of intracellular signals triggered by activated immunoreceptors, including B cell receptors (BCR) and Fc receptors. Activation of the immunoreceptor leads to phosphorylation of ITAMs (immunoreceptor tyrosine-based activation motifs) by a receptor associated kinase and recruitment of Syk. Binding of Syk to the receptor leads to a conformational change of the Syk protein and Syk activation. The activated Syk-receptor complex can then phosphorylate adaptor proteins (e.g. BLNK/SLP-65, SLP-76 and LAT) and recruit and signal through various key regulatory effectors including PI3K/AKT, Ras/ERK, and IKK/NF-κB. In one embodiment, a Syk inhibitor inhibits the activation of Syk. In one embodiment, a Syk inhibitor prevents the binding of phosphotyrosine to the SH2 (Src homology 2) domains of Syk. In another embodiment, a Syk inhibitor inhibits the enzymatic activity of Syk. In one embodiment, the Syk inhibitor is a small chemical molecule. In one embodiment, the Syk inhibitor is an antibody. In another embodiment, the Syk inhibitor is a small RNA (antisense RNA, siRNA, miRNA). In some embodiments, the Syk inhibitors include, but are not limited to, PRT062607, Fostamatinib (R788), R406, R788 (Fostamatinib) disodium, PRT-060318, BAY-61-3606, Entospletinib, R09021, and their derivatives or analogues. In one embodiment, the Syk inhibitor for immune cell modulation comprises PRT062607. In another embodiment, the Syk inhibitor for immune cell modulation comprises R788.

As understood by those skilled in the art, the scope of the present invention also includes analogues or derivatives of all other agents functionally categorized under their respective class based on their targets, which analogues or derivatives include, but are not limited to, salt, ester, ether, solvate, hydrate, stereoisomer or prodrug.

In some embodiments, the composition for improving therapeutic potential of immune cells suitable for adoptive cell-based therapies comprises at least one class of modulating agent selected from the group consisting of BET inhibitors, CDK inhibitors, CRAC channel inhibitors, Cox inhibitors, dopamine antagonists, ERK5 inhibitors, glucocorticoids, IGF-1R inhibitors, IKK inhibitors, JAK inhibitors, Lck inhibitors, PDK1 inhibitors, Raf inhibitors, and Syk inhibitors.

In one embodiment, the composition comprising at least one class of modulating agent selected from the group consisting of BET inhibitors, CDK inhibitors, CRAC channel inhibitors, Cox inhibitors, dopamine antagonists, ERK5 inhibitors, glucocorticoids, IGF-1R inhibitors, IKK inhibitors, JAK inhibitors, Lck inhibitors, PDK1 inhibitors, Raf inhibitors, and Syk inhibitors further comprises an organic solvent. In certain embodiments, the organic solvent is substantially free of methyl acetate. In certain embodiments, the organic solvent is selected from the group consisting of dimethyl sulfoxide (DMSO), N,N-dimethylformamide (DMF), dimethoxyethane (DME), dimethylacetamide, ethanol, and combinations thereof. In some embodiments, the organic solvent is DMSO. In some embodiments, the organic solvent is ethanol. In some other embodiments, the organic solvent is a mixture of DMSO and ethanol.

In some embodiments, the composition for improving therapeutic potential of immune cells suitable for adoptive cell-based therapies comprises at least one compound selected from Table 1, or derivatives or analogues thereof. In some embodiments, the composition for improving therapeutic potential of immune cells comprises at least one agent, wherein the agent is a BET inhibitor, an IKK inhibitor, a JAK inhibitor, a PDK1 inhibitor, a Raf inhibitor, or a Syk inhibitor. In some embodiments, the composition for improving therapeutic potential of immune cells comprises at least a PDK1 inhibitor. In some other embodiments, the composition for improving therapeutic potential of immune cells comprises at least a Raf inhibitor. In some other embodiments, the composition for improving therapeutic potential of immune cells comprises at least a Syk inhibitor. In yet another embodiment, the composition for improving therapeutic potential of immune cells comprises at least one of GSK2334470, AZ628, GDC-0879, Dabrafenib, R788, pacritinib and PRT062607. In one embodiment, the composition for immune cell modulation comprises GSK2334470. In another embodiment, the composition for immune cell modulation comprises AZ628. In yet another embodiment, the composition for immune cell modulation comprises R788. In some other embodiments, the composition of one or more modulating agents comprises Bardoxolone methyl.

In some embodiments, the composition comprising at least one of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor, further comprises at least one of a GSK3 inhibitor, a MEK inhibitor, a ROCK inhibitor, and a TGFβ inhibitor, wherein the composition is useful for improving therapeutic potential of immune cells suitable for adoptive cell-based therapies.

In some embodiments, the composition comprises a combination of modulating agents comprising two or more of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor. In some embodiments, the two or more agents, when combined in the composition, have additive effect in modulating the cells for therapeutic use. As defined, "additive" refers to when two or more agents in a combination produce an effect nearly equal to the sum of their individual effects. In some embodiments, the two or more agents, when combined in the composition, have synergistic effect in modulating the cells for therapeutic use. As defined, "synergy" is an enhanced effect such that the working together of two or more agents to produce an effect greater than the sum of their individual effects. In some embodiments, one or more of the combined agents in the composition are from the same class in view of their target. In some embodiments, one or more of the combined agents in the composition are from different classes in that each affects a different target.

In some embodiments, the composition comprising one or more modulating agents selected from the group consisting of BET inhibitors, CDK inhibitors, CRAC channel inhibitors, cox inhibitors, dopamine antagonists, ERK5 inhibitors, glucocorticoids, IGF-1R inhibitors, IKK inhibitors, JAK inhibitors, Lck inhibitors, PDK1 inhibitors, Raf inhibitors, and Syk inhibitors, further comprises one or more additional additives. In one embodiment, the one or more additives are selected from the group consisting of peptides, cytokines, mitogens, growth factors, small RNAs, dsRNAs (double stranded RNA), mononuclear blood cells, feeder cells, feeder cell components or replacement factors, vectors comprising one or more polynucleic acids of interest, antibodies and antibody fragments thereof, and chemotherapeutic agent or radioactive moiety. In some embodiments, the additional additive comprises an antibody, or an antibody fragment. In some of these embodiments, the antibody, or antibody fragment, specifically binds to a viral antigen. In other embodiments, the antibody, or antibody fragment, specifically binds to a tumor antigen.

In some embodiments, the cytokines or growth factors as additives of the composition comprise one or more of the following: epidermal growth factor (EGF), acidic fibroblast growth factor (aFGF), basic fibroblast growth factor (bFGF), leukemia inhibitory factor (LIF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-γ), stem cell factor (SCF), thrombopoietin (Tpo), and erythropoietin (Epo). In some embodiments, the cytokine as an additive comprises at least interleukin-2 (IL-2), interleukin 7 (IL-7), interleukin 10 (IL-10), interleukin-12 (IL-12), interleukin-15, interleukin 18 (IL-18), interleukin 21 (IL-21), or any combinations thereof. In some embodiments, the growth factor of the composition comprises fibroblast growth factor. These cytokines may be obtained commercially, for example from R&D Systems (Minneapolis, Minn.), and may be either natural or recombinant. In particular embodiments, growth factors and cytokines may be added at concentrations contemplated herein. In certain embodiments growth factors and cytokines may be added at concentrations that are determined empirically or as guided by the established cytokine art.

In some embodiments, the mitogen as an additive of the composition comprises concanavalin A. In some other embodiments, the feeder cells of the composition are genetically modified. In some embodiments, the feeder cells of the composition comprise one or more of the followings: mononuclear blood cells, thymic epithelial cells, endothelial cells, fibroblasts, leukemic cells K562, Raji cells, or feeder cell components or replacement factors thereof.

In some embodiments, the small RNA of the composition comprises one or more of siRNA, shRNA, miRNA and antisense nucleic acids. In some other embodiments, the small RNA of the composition comprises one or more of the following: miR-362-5p, miR-483-3p, miR-210 and miR-598.

In some embodiments, the vector of the composition comprising one or more polynucleic acids of interest is integrating or non-integrating. In some embodiments, the vector of the composition comprising one or more polynucleic acids of interest further comprises backbones of an adenovirus vector, plasmid vector, adeno-associated virus vector, retrovirus vector, lentivirus vector, Sendai virus vector and episomal vector. In some embodiments, the plasmid vectors for the expression in animal cells include, for example, pAl-11, pXT1, pRc/CMV, pRc/RSV, pcDNAI/Neo, and the like. In some embodiments, the one or more polynucleic acids comprised in the vector encode one or more proteins or polypeptides. In some embodiments, the one or more polynucleic acids encode Delta-like 1 (DLL1), Delta-like 3 (DLL3), Delta-like 4 (DLL4), Jagged1 (Jag1), or Jagged2. In some embodiments, the one or more polynucleic acids encode Jagged 1.

In some embodiments, the composition additionally comprises at least one therapeutic agent. In one embodiment, the therapeutic agent comprises an antibody, or an antibody fragment. In some embodiments, the antibody may be a humanized antibody, a humanized monoclonal antibody, a chimeric antibody. In some embodiments, the antibody, or antibody fragment, specifically binds to a viral antigen. In some embodiments, the antibodies of the composition include, but are not limited to, anti-CD20 (retuximab, veltuzumab, ofatumumab, ublituximab, ocaratuzumab, obinutuzumab), anti-Her2 (trastuzumab), anti-CD52 (alemtuzumab), anti-EGFR (certuximab), and anti-CD38 (daratumumab), and their humanized and Fc modified variants. Additionally, the design of bi- and trispecific antibodies, fusing the Fab region of the antibody targeting the tumor cell antigen, such as the anti-CD19, CD20, and CD33 antigens, in combination with another Fab region recognizing a surface protein of the immune cell leads to stimulation of the cells followed by tumor cell killing.

In some embodiments, the additional additive to the composition comprises one or more of a chemotherapeutic agent, a radioactive moiety, and an immunomodulatory drug (IMiD). Immunomodulatory drugs such as thalidomide, lenalidomide, and pomalidomide stimulate both NK cells and T cells. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate.

Other suitable therapeutic agents are those that are approved for human use, including those that will be approved, as chemotherapeutics or radiotherapeutics, and known in the art. Such agents can be referenced through any of a number of standard physicians' and oncologists' references (e.g. Goodman & Gilman's The Pharmacological Basis of Therapeutics, Ninth Edition, McGraw-Hill, N.Y., 1995) or through the National Cancer Institute website (fda.gov/cder/cancer/druglistfrarne.htm), both as updated from time to time.

II. Immune Cells for Modulation and Modulated Immune Cells Therefrom

The present invention provides a population or subpopulation of modulated immune cells that has been modulated by contacting with one or more modulating agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor, in an amount sufficient to improve the therapeutic potential of the immune cells.

The present invention also provides a composition comprising a population or subpopulation of modulated immune cells that has been contacted with one or more modulating agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor, in an amount sufficient to improve the therapeutic potential of the immune cells.

The present invention further provides a population or subpopulation of isolated immune cells, and one or more modulating agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor, wherein treatment by contacting the population or subpopulation of the isolated immune cells using the one or more of said agents improves the therapeutic potential of the immune cells for adoptive therapy. The treatment can modify the biological properties of the immune cells to improve cell proliferation, cytotoxicity, persistence, and/or reduce the relapse rate of the cell therapy.

In some embodiments, the one or more modulating agents comprise at least one compound selected from Table 1, and derivatives or analogues thereof. In some embodiments, the one or more modulating agents comprise a BET inhibitor, an IKK inhibitor, a JAK inhibitor, a PDK1 inhibitor, a Raf inhibitor, or a Syk inhibitor. In some embodiments, the one or more modulating agents comprise at least a PDK1 inhibitor. In some other embodiments, the one or more modulating agents comprise at least a Raf inhibitor. In some other embodiments, the one or more modulating agents comprise at least a Syk inhibitor. In yet another embodiment, the one or more modulating agents comprise at least one of GSK2334470, AZ628, GDC-0879, Dabrafenib, R788, pacritinib, Bardoxolone methyl, and PRT062607. In one embodiment, the one or more modulating agents comprise GSK2334470. In another embodiment, the one or more modulating agents comprise AZ628. In yet another embodiment, the one or more modulating agents comprise R788. In some other embodiments, the composition of one or more modulating agents comprises Bardoxolone methyl.

In some embodiments, the population of modulated immune cells comprises T cells. In some embodiments, the population of modulated immune cells comprises NK cells. In some embodiments, the population of modulated immune cell comprises NKT cell.

In some embodiments, the population or subpopulation of T cells contacted with one or more modulating agents comprises an increased number or relative ratio of naïve T cells (Tn), stem cell memory T cells (Tscm), and/or central memory T cells (Tcm), and/or improved cell proliferation, cytotoxicity, cell recall, and/or persistence in comparison to the T cells without the same treatment. In some embodiments, the number of Tn, Tscm, and/or Tcm is increased by at least 10%, 20%, 30%, 40%, 50%, 60%, 70%, 80%, 90%, or more, or increased by at least 2, 3, 4, 5, 10, 15, or 20 fold, or more, compared to the number of Tn, Tscm, and/or Tcm in the cell population without the same treatment with one or more modulating agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor.

In some embodiments, a population or subpopulation of NK cells contacted with one or more of said modulating agents comprises an increased number or relative ratio of adaptive (or memory) NK cells, and/or improved cell proliferation, cytotoxicity, cell recall, and/or persistence in comparison to the NK cells without the same treatment. In some embodiments the number of adaptive NK cells is increased by at least 10%, 20%, 30%, 40%, 50%, 60%, 70%, 80%, 90%, or more, or increased by at least 2, 3, 4, 5, 10, 15, or 20 fold, or more, compared to the number of adaptive NK cells in the cell population without the same treatment with one or more of said agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor. In one embodiment, a population or subpopulation of NK cells contacted with one or more of said agents comprises an increased number or relative ratio of adaptive NK cells. In one embodiment, the adaptive NK cell is characterized by CD3− and CD56+, and at least one of CD57+, NKG2C+, low PLZF, low SYK, low FcεRγ, low EAT-2, low TIGIT, low PD1, low CD7, low CD161, high LILRB1, high CD45RO, and low CD45RA. In some embodiments, the adaptive NK cells are at least two of CD57+, NKG2C+, low PLZF, low SYK, low FcεRγ, low EAT-2, low TIGIT, low PD1, low CD7, low CD161, high LILRB1, high CD45RO, and low CD45RA. For example, the adaptive NK cell can be CD57+ and NKG2C+. In some embodiments, the adaptive NK cells are at least three of CD57+, NKG2C+, low PLZF, low SYK, low FcεRγ, low EAT-2, low TIGIT, low PD1, low CD7, low CD161, high LILRB1, high CD45RO, and low CD45RA. For example, the adaptive NK cell can be SYK-, FcεRγ-, and EAT-2-. In one embodiment, the population or subpopulation of NK cells contacted with one or more of said agents is further contacted with a GSK3 inhibitor, a MEK inhibitor, a ROCK inhibitor, a TGFβ inhibitor, a PDK1 agonist, and/or a rapamycin. In one embodiment, the GSK3 inhibitor is CHIR99021, BIO, TWS119, or Kenpaullone. In one embodiment, the GSK3 inhibitor is TWS119. In another embodiment, the GSK3 inhibitor is CHIR99021. In yet another embodiment the GSK3 inhibitor is BIO.

In some other embodiments, a population or subpopulation of NKT cells contacted with one or more modulating agents comprises an increased number or relative ratio of type I NKT cells vs type II, and/or improved cell proliferation, cytotoxicity, cell recall, and/or persistence in comparison to the isolated population or subpopulation of NKT cells without the treatment with one or more of said modulating agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor. In some embodiments, the number of type I NKT cells is increased by at least 10%, 20%, 30%, 40%, 50%, 60%, 70%, 80%, 90%, or more, or increased by at least 5, 10, 15, or 20 fold, or more, compared to the number of type I NKT cells in the cell population without the same treatment with one or more of said agents.

In some non-limiting embodiments, the increased number or relative ratio of naïve T cells (Tn), stem cell memory T cells (Tscm), central memory T cells (Tcm), adaptive NK cells, and/or type I NKT cells in a modulated immune cell population are due to improved maintenance and expansion of these cell subtypes, and/or increased cell dedifferentiation/reprogramming from more mature cell subtypes to cell subtypes in a desired differentiation state, and/or phenotype skewing from one to another.

In some embodiments, after contacting a population of immune cell with one or more of said modulating agents, the number of naïve T cells (Tn), stem cell memory T cells (Tscm), central memory T cells (Tcm) in the modulated cell population is increased in comparison to untreated immune cell population, wherein the Tn, Tscm and Tcm are characterized by co-expression of CCR7 and/or CD62L.

In some embodiments, after contacting a population of immune cells with one or more of said modulating agents, the number of adaptive NK cells in the modulated cell population is increased in comparison to untreated immune cell population, wherein the adaptive NK cells are characterized by CD3−, CD56+, CD16+, NKG2C+, and CD57+. In some other embodiments, the adaptive NK cells are characterized by CD3−, CD56+, and at least one, two or three of CD57+, NKG2C+, low PLZF, low SYK, low FcεRγ, low EAT-2, low TIGIT, low PD1, low CD7, low CD161, high LILRB1, high CD45RO, and low CD45RA.

In some embodiments, after contacting a population of immune cells with one or more of said modulating agents, the number of type I NKT cells in the modulated cell population is increased in comparison to untreated immune cell population, wherein the type I NKT cells are characterized by surface antigens CD3+, CD56+, TCR Vα24+, and/or TCR Vβ11+.

In some embodiments, the population or subpopulation of T, NK or NKT cells for treatment by the modulating agents disclosed herein can be isolated from a human or a non-human mammal. Examples of such non-human mammals include, but are not limited to rabbit, horse, bovine, sheep, pigs, dogs, cats, mice, rats, and transgenic species thereof.

The population or subpopulation of T cells for modulation can be obtained or isolated from a number of sources, including but not limited to peripheral blood, bone marrow, lymph node tissue, cord blood, thymus tissue, and tissue from a site of infection, ascites, pleural effusion, spleen tissue, and tumors. The bone marrow can be obtained from femurs, iliac crest, hip, ribs, sternum, and other bones. In addition, the T cell lines available in the art can also be used, such as Jurkat, SupT1, and others.

The population or subpopulation of NK cells for modulation can be obtained, or can be enriched, from a number of sources, including but not limited to peripheral blood, cord blood, and tumors.

Fully mature NKT cells for modulation can be obtained, or can be enriched, from peripheral blood, with smaller populations of mature NKT cells potentially found in bone marrow, lymph node tissue and cord blood, thymus tissue.

In certain embodiments of the present invention, an isolated or enriched population or subpopulation of immune cells comprising T, NK, and/or NKT cells for modulation can be obtained from a unit of blood using any number of techniques known to the skilled artisan, such as Ficoll™ separation. In one embodiment, T, NK or NKT cells from the circulating blood of an individual are obtained by apheresis. The apheresis product typically contains cells, including T cells, monocytes, granulocytes, B cells, NK cells, NKT cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, Ca-free, Mg-free PBS, PlasmaLyte A, or other saline solution with or without buffer. Alternatively, the undesirable components of the apheresis sample can be removed and the cells directly resuspended in culture media.

In another embodiment, the population of immune cells comprising T, NK or NKT cells, or subpopulations thereof for modulation are isolated or enriched from peripheral blood lymphocytes by lysing the red blood cells and depleting the monocytes, for example, by centrifugation through a PERCOLL™ gradient or by counterflow centrifugal elutriation.

In one embodiment, a specific subpopulation of T cells for modulation, can be further isolated or enriched by positive or negative selection techniques such as CD3, CD28, CD4, CD8, CD45RA, CD45RO, CD62L, CCR7, CD27, and/or CD122 antibodies. For example, in one embodiment, blood cells (e.g. from a leukopak) are purified through a Ficoll gradient to remove platelets and red cells. The remaining PBMCs are then purified, for example to yield CD3+ T cells, CD4+ T cells or CD8+ T cells using either positive selection with an EasySep system (StemCell Technologies) or negative selection with a MACS system (Miltenyi Biotec). Longer incubation times can be used to isolate T cells in any situation where there are few T cells as compared to other cell types, such in isolating tumor infiltrating lymphocytes (TIL) from tumor tissue or from immunocompromised individuals. The skilled artisan would recognize that multiple rounds of selection can also be used in the context of this invention. In certain embodiments, it can be desirable to perform the selection procedure and use the "unselected" cells in the activation and expansion process. "Unselected" cells can also be subjected to further rounds of selection.

Isolation or enrichment of a population of immune cells comprising T, NK, NKT cells or subpopulations thereof for modulation by negative selection can be accomplished with a combination of antibodies directed to surface markers unique to the negatively selected cells. One method is cell sorting and/or selection via negative magnetic immunoadherence or fluorescence-activated cell sorting that uses a cocktail of monoclonal antibodies directed to cell surface markers present on the cells negatively selected. For example, to enrich for CD3+ cells by negative selection, a monoclonal antibody cocktail typically includes antibodies to CD14, CD20, CD11b, CD16, and HLA-DR. In certain embodiments, it can be desirable to enrich for or positively select for regulatory T cells which typically express CD4+, CD25+, CD62Lhi, GITR+, and FoxP3+. Alternatively, in certain embodiments, T regulatory cells are depleted by anti-CD25 conjugated beads or other similar method of selection. In some embodiments, a desired T cell subpopulation for immunotherapy is enriched or selected from the modulated immune cells comprising T cells by CCR7 and CD62L. Alternatively cells of interest may be selected according to physical parameters including differential size, density, granularity, deformability, resistance or capacitance.

In one embodiment, a population of immune cells comprising adaptive NK cells for modulation is enriched by selecting within the modulated immune cells comprising NK cells for those phenotypically CD3− and CD56+, using the identifiers such as include positive expression of CD16, NKG2C, and CD57. Further, negative selection of adaptive subpopulation can be based on lack of expression of NKG2C and/or CD57, and additionally lack expression of one or more of the following: low PLZF, low SYK, low FcεRγ, low EAT-2, low TIGIT, low PD1, low CD7, low CD161, high LILRB1, high CD45RO, and low CD45RA.

In one embodiment, a population or subpopulation of NKT cells for modulation is enriched by selecting within the population of NK cells for those phenotypically expressing the invariant TCRα chain, and specifically the following combination of markers: CD3+, CD56+, TCR Vα24+, and/or TCR Vβ11+. Alternatively, NKT cells can be selected based on a combination of phenotype combined with expression of the invariant TCRα chain.

The blood samples or apheresis product from a subject can be collected at a time period prior to when the immune cells as described herein are isolated. As such, the source of the cells to be modulated can be collected at any of a number of suitable time points, and desired cells, such as T cells, NK cells and NKT cells, isolated and frozen for later use in cell-based immunotherapy for any number of diseases or conditions that would benefit from such cell therapy, such as those described herein. In one embodiment, a blood sample or an apheresis product is collected from a generally healthy subject. In certain embodiments, a blood or an apheresis product is collected from a generally healthy subject who is at risk of developing a disease, but who has not yet developed a disease, and the cells of interest are isolated and frozen for later use. In other embodiments, a blood sample or apheresis product is collected from a subject with a specific disease (e.g. cancer). In yet another embodiment, a blood sample or an apheresis product is collected from a subject who has been previously administered genetically modified immune cells (genetically engineered or derived from rearrangements, mutations, genetic imprinting and/or epigenetic modification). In certain embodiments, the T, NK, NKT or other immune cells can be expanded, frozen, and treated and used at a later time. In certain embodiments, samples are collected from a patient shortly after diagnosis of a particular disease as described herein but prior to any treatments. In some embodiments, the cells are isolated from a subject presenting CMV (cytomegalovirus) seropositivity. In a further embodiment, the cells are isolated from a blood or an apheresis product from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, mycophenolic acid, steroids, FR901228, and irradiation. In a further embodiment, the cells are isolated from a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, the immune cells for modulation comprising T, NK or NKT cells, and/or subpopulations thereof are genomically engineered, which may include insertion, deletion, or nucleic acid replacement. Modified immune cells may express cytokine transgenes, silenced inhibitory receptors, or overexpress activating receptors, or CARs for retargeting the immune cells. In some embodiments, the population of immune cells isolated for modulation from a subject, or donor, or isolated from or comprised in peripheral blood, bone marrow, lymph node tissue, cord blood, thymus tissue, tissue from a site of infection, ascites, pleural effusion, spleen tissue, tumors of a subject/donor may be genetically modified. In some embodiments, the isolated population of immune cells and the modulated immune cells obtained therefrom are genomically engineered and comprise an insertion, a deletion, and/or a nucleic acid replacement. In some particular embodiments, the immune cells for modulation and the modulated immune cells obtained therefrom comprise an exogenous nucleic acid encoding a T Cell Receptor (TCR), a Chimeric Antigen Receptor (CAR), and/or overexpression of CD16 or a variant thereof.

Generally, the chimeric antigen receptor (CAR) comprises an ectodomain that includes an antigen recognition region, a transmembrane domain linked to the ectodomain, and an endodomain linked to the transmembrane domain. The endodomain comprises one or more signaling domains that activates the cells expressing the CAR upon binding of the antigen recognition region to antigen-expressing target cells. In some embodiments, the antigen can be expressed as a peptide or as an intact protein or portion thereof.

Antibodies include antigen binding fragments thereof, comprising at least a light chain or heavy chain immunoglobulin variable region which specifically recognizes and binds an epitope of an antigen, such as a peptide, lipid, polysaccharide, or nucleic acid containing an antigenic determinant. Variable forms of antibodies or antigen binding fragments thereof include, but are not limited to, Camel Ig (or, "camelid $V_HH$"; Muyldermans et al., Protein Eng., 7:1129-1135, 1994); Ig NAR (new antigen receptor, Nuttall et al., Mol. Immunol., 38:313-326, 2001), Fab fragments, Fab' fragments, F(ab)'2 fragments, F(ab)'3 fragments, Fv, single chain Fv proteins ("scFv"), bis-scFv, (scFv)2, minibodies, diabodies, triabodies, tetrabodies, disulfide stabilized Fv proteins ("dsFv"), and single-domain antibody (sdAb, Nanobody) and portions of full length antibodies responsible for antigen binding. The term "antibody" also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.) In certain embodiments, the extracellular antigen-binding domain is a humanized scFv. In certain embodiments, the scFv is a murine scFv. In certain embodiments, the extracellular antigen binding domain is a Fab, which is optionally crosslinked. In certain embodiments, the extracellular antigen-binding domain is a F(ab)L. In certain embodiments, any of the foregoing molecules may be comprised in a fusion protein with a heterologous sequence to form the extracellular antigen-binding domain. In certain embodiments, the scFv is identified by screening scFv phage library with an antigen-Fe fusion protein. The scFv can be derived from a mouse bearing human VL and/or VH genes. The scFv can also be substituted with a camelid heavy chain, or a partial natural ligand for a cell surface receptor.

In certain embodiments, the immune cells for modulation and the modulated immune cells obtained therefrom comprise a CAR specific to a tumor antigen. In certain embodiments, the immune cells for modulation and the modulated immune cells obtained therefrom comprise a CAR specific to a pathogen antigen. Non-limiting examples of tumor or pathogen antigens include AChR (fetal acetylcholine receptor), ADGRE2, AFP (alpha fetoprotein), BAFF-R, BCMA, CAIX (carbonic anhydrase IX), CCR1, CCR4, CEA (carcinoembryonic antigen), CD3, CD5, CD8, CD7, CD10, CD13, CD14, CD15, CD19, CD20, CD22, CD30, CD33, CLLI, CD34, CD38, CD41, CD44, CD49f, CD56, CD61, CD64, CD68, CD70, CD74, CD99, CD117, CD123, CD133, CD138, CD44v6, CD267, CD269, CDS, CLEC12A, CS1, EGP-2 (epithelial glycoprotein-2), EGP-40 (epithelial glycoprotein-40), EGFR(HER1), EGFR-VIII, EpCAM (epithelial cell adhesion molecule), EphA2, ERBB2 (HER2, human epidermal growth factor receptor 2), ERBB3, ERBB4, FBP (folate-binding protein), Flt3 receptor, folate receptor-a, GD2 (ganglioside G2), GD3 (ganglioside G3), GPC3 (glypican-3), GPI00, hTERT (human telomerase reverse transcriptase), ICAM-1, integrin B7, interleukin 6 receptor, IL13Ra2 (interleukin-13 receptor 30 subunit alpha-2), kappa-light chain, KDR (kinase insert domain receptor), LeY (Lewis Y), L1CAM (L1 cell adhesion molecule), LILRB2 (leukocyte immunoglobulin like receptor B2), MART1, MAGE-A1 (melanoma associated antigen A1), MAGE-A3, MSLN (mesothelin), MUC16 (mucin 16), MUCI (mucin I), NKG2D ligands, NY-ESO-1 (cancer-testis antigen), PRI (proteinase 3), TRBCI, TRBC2, TIM-3, TACI, tyrosinase, survivin, hTERT, oncofetal antigen (h5T4), p53, PSCA (prostate stem cell antigen), PSMA (prostate-specific membrane antigen), hROR1, TAG-72 (tumor-associated glycoprotein 72), VEGF-R2 (vascular endothelial growth factor R2), WT-1 (Wilms tumor protein), and antigens of HIV (human immunodeficiency virus), hepatitis B, hepatitis C, CMV (cytomegalovirus), EBV (Epstein-Barr virus), HPV (human papilloma virus), and others.

In one embodiment, the immune cells for modulation and the modulated immune cells obtained therefrom comprise at least a CAR specific to CD19. In another embodiment, the immune cells for modulation and the modulated immune cells obtained therefrom comprise at least a CAR specific to BCMA.

In one embodiment, the genomically engineered immune cells for modulation and the modulated immune cells obtained therefrom comprise one or more genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region; (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In some embodiments, the T, NK or NKT cells, for modulation or modulated therefrom, comprise an exogenous nucleic acid. In some embodiments, the exogenous nucleic acid is introduced to the immune cells via direct genomic editing of the cells. In some other embodiments, the exogenous nucleic acid is introduced to the immune cells via retaining the same from a genomically engineered hematopoietic stem or progenitor cell or iPSC, which gives rise to the immune cell through differentiation. In some embodiments, the exogenous nucleic acid for a T cell can encode a TCR (T Cell Receptor), a CAR (Chimeric Antigen Receptor), a bi-specific T cell engager (BiTE), a tri-specific T cell engager, a multi-specific T cell engager, or a universal engager compatible with multiple immune cell types. In some embodiments, the exogenous nucleic acid for an NK cell can encode a TCR, a CAR, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid for an NKT cell can be an altered TCR or CAR. In some embodiments, the exogenous nucleic acid can encode a CD19 CAR. In some embodiments, the exogenous nucleic acid can encode a BCMA CAR. In some embodiments, CD16 variants comprise high-affinity CD16 (HACD16), non-cleavable CD16, and high-affinity non-cleavable CD16 (hnCD16).

In some embodiments, the population or subpopulation of immune cells for modulation is differentiated in vitro from a stem cell or progenitor cell. In some embodiments, the isolated population or subpopulation of T, NK or NKT cells can be differentiated from a stem cell, a hematopoietic stem or progenitor cell (HSC), or a progenitor cell. The progenitor cell can be a CD34+ hemogenic endothelium cell, a multipotent progenitor cell, a T cell progenitor, an NK cell progenitor, or an NKT cell progenitor. The stem cell can be a pluripotent stem cell, such as induced pluripotent stem cells (iPSCs) and embryonic stem cells (ESCs). The iPSC is a non-naturally occurring reprogrammed pluripotent cell. Once the cells of a subject have been reprogrammed to a pluripotent state, the cells can then be programmed or differentiated to a desired cell type or subtypes, such as T, NK, or NKT cells.

In some embodiments, the iPSC is differentiated to a T, NK or NKT cells by a multi-stage differentiation platform wherein cells from various stages of development can be induced to assume a hematopoietic phenotype, ranging from mesodermal stem cells, to fully differentiated T, NK or NKT cells (See e.g. U.S. Applications 62/107,517 and 62/251, 016, and US20180072992A1, the disclosures of which are incorporated herein in their entireties). In some embodiments, the iPSC, HSC, or progenitor for T, NK or NKT cell differentiation is genomically engineered, which may include insertion, deletion, or nucleic acid replacement.

In some embodiments, the genomically engineered iPSC, HSC or hematopoietic progenitor cells comprise one or more genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSC, HSC, progenitor, or their derived cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any of the HLA genes in the chromosome 6p21 region; or (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, surface triggering receptors for coupling with bi- or multi-specific or universal engagers, a TCR (T Cell Receptor), or a CAR (Chimeric Antigen Receptor). In some embodiments, the iPSC, HSC, or progenitor for T, NK or NKT cell differentiation comprises modified HLA class I and/or II. In some embodiments, the iPSC, HSC, or progenitor for T, NK or NKT cell differentiation with modified HLA class I and/or II comprises null or low expression of at least one of B2M, HLA-E/G, PDL1, A2AR, CD47, LAG3, TIM3, TAP1, TAP2, Tapasin, NLRC5, PD1, RFKANK, CIITA, RFX5, and RFXAP. In some embodiments, the iPSC, HSC, or progenitor for T, NK or NKT cell differentiation has an exogenous nucleic acid. In some embodiments, the exogenous nucleic acid can encode, a bi-specific T cell engager (BiTE), a tri-specific T cell engager, a multi-specific T cell engager, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid encodes hnCD16 in the iPSC, HSC, or progenitor for T, NK or NKT cell differentiation. In some embodiments, the exogenous nucleic acid encodes a CD19 CAR in the iPSC, HSC, or progenitor for T, NK or NKT cell differentiation. In some embodiments, the exogenous nucleic acid encodes a BCMA CAR in the iPSC, HSC, or progenitor for T, NK or NKT cell differentiation.

In some embodiments, the population or subpopulation of immune cells is trans-differentiated in vitro from a non-pluripotent cell of non-hematopoietic fate to a hematopoietic lineage cell or from a non-pluripotent cell of a first hematopoietic cell type to a different hematopoietic cell type, which can be a T, NK, or NKT progenitor cell or a fully differentiated specific type of immune cell, such as T, NK, or NKT cell (See e.g. U.S. Pat. No. 9,376,664 and U.S. application Ser. No. 15/072,769, the disclosure of which is incorporated herein in their entirety). In some embodiments, the non-pluripotent cell of non-hematopoietic fate is a somatic cell, such as a skin fibroblast, an adipose tissue-derived cell and a human umbilical vein endothelial cell (HUVEC). Somatic cells useful for trans-differentiation may be immortalized somatic cells.

Various strategies are being pursued to induce pluripotency, or increase potency, in cells (Takahashi, K., and Yamanaka, S., Cell 126, 663-676 (2006); Takahashi et al., Cell 131, 861-872 (2007); Yu et al., Science 318, 1917-1920 (2007); Zhou et al., Cell Stem Cell 4, 381-384 (2009); Kim et al., Cell Stem Cell 4, 472-476 (2009); Yamanaka et al., 2009; Saha, K., Jaenisch, R., Cell Stem Cell 5, 584-595 (2009)), and improve the efficiency of reprogramming (Shi et al., Cell Stem Cell 2, 525-528 (2008a); Shi et al., Cell Stem Cell 3, 568-574 (2008b); Huangfu et al., Nat Biotechnol 26, 795-797 (2008a); Huangfu et al., Nat Biotechnol 26, 1269-1275 (2008b); Silva et al., Plos Bio 6, e253. Doi: 10.1371/journal. Pbio. 0060253 (2008); Lyssiotis et al., PNAS 106, 8912-8917 (2009); Ichida et al., Cell Stem Cell 5, 491-503 (2009); Maherali, N., Hochedlinger, K., Curr Biol 19, 1718-1723 (2009b); Esteban et al., Cell Stem Cell 6, 71-79 (2010); and Feng et al., Cell Stem Cell 4, 301-312 (2009)), the disclosures of which are hereby incorporated by reference in their entireties.

III. Method of Modulating Immune Cells for Adoptive Therapies

The present invention in some embodiments provides a method of modulating a population or a subpopulation of immune cells suitable for adoptive cell-based therapies, and the method comprises contacting the immune cells with a composition comprising one or more modulating agents comprising at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor, wherein the population or subpopulation of immune cells contacted with the one or more of said agents has improved therapeutic potential in comparison to the cells without the modulation. The modulation with one or more of said agents can modify the biological properties of the immune cells to improve cell proliferation, cytotoxicity, persistence, and/or reduce the relapse rate in a cell therapy. In some embodiments, the composition of one or more modulating agents comprises at least one compound selected from Table 1, and derivatives or analogues thereof. In some embodiments, the composition of one or more modulating agents comprises a BET inhibitor, an IKK inhibitor, a JAK inhibitor, a PDK1 inhibitor, a Raf inhibitor, or a Syk inhibitor. In some embodiments, the composition of one or more modulating agents comprises at least a PDK1 inhibitor. In some other embodiments, the composition of one or more modulating agents comprises at least a Raf inhibitor. In some other embodiments, the composition of one or more modulating agents comprises at least a Syk inhibitor. In yet another embodiment, the composition of one or more modulating agents comprises at least one of GSK2334470, AZ628, GDC-0879, Dabrafenib, R788, pacritinib, Bardoxolone methyl, and PRT062607. In one embodiment, the composition of one or more modulating agents comprises GSK2334470. In another embodiment, the composition of one or more modulating agents comprises AZ628. In yet another embodiment, the composition of one or more modulating agents comprises R788. In some other embodiments, the composition of one or more modulating agents comprises Bardoxolone methyl.

In one embodiment, the method of modulating a population or a subpopulation of immune cells comprises contacting the immune cells with a composition comprising at least one modulating agent, wherein the at least one modulating agent comprises a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor; and wherein the contacted immune cells obtain at least one desirable therapeutic attribute including, but not limited to: increased cell expansion; increased number or relative ratio of one or more desired cell subpopulations; improved proliferation, cytotoxicity, or cell recall; and improved persistence, in comparison to immune cells without contacting the same composition.

In some embodiments, the method of modulating a population or a subpopulation of immune cells suitable for adoptive cell-based therapies comprises contacting the immune cells with a composition comprising at least one said agent in a sufficient amount to improve at least one desirable therapeutic attribute in comparison to immune cells without contacting the same composition. In one embodiment, the modulating agent for immune cell treatment is between about 0.1 nM to about 50 µM. In one embodiment, the agent for immune cell treatment is about 0.1 nM, 0.5 nM, 1 nM, 5 nM, 10 nM, 50 nM, 100 nM, 500 nM, 1 µM, 5 µM, 10 µM, 20 µM, or 25 µM, or any concentration in-between. In one embodiment, the modulating agent for immune cell treatment is between about 0.1 nM to about 5 nM, is between about 1 nM to about 100 nM, is between about 50 nM to about 250 nM, between about 100 nM to about 500 nM, between about 250 nM to about 1 µM, between about 500 nM to about 5 µM, between about 3 µM to about 10 µM, between about 5 µM to about 15 µM, between about 12 µM to about 20 µM, or between about 18 µM to about 25 µM, or any range in-between.

In some embodiments, the method of modulating a population or a subpopulation of immune cells suitable for adoptive cell-based therapies comprises contacting the immune cells with a composition comprising at least one said modulating agent for a sufficient length of time to improve at least one desirable therapeutic attribute in comparison to immune cells without contacting the same composition. In one embodiment, the immune cells are contacted with one or more of said agents for at least 10 minutes, 30 minutes, 1 hours, 2, hours, 5 hours, 12 hours, 16 hours, 18 hours, 1 day, 2 days, 3 days, 4 days, 5 days, 6 days, 7 days, 10 days, 15 days, 20 days, 25 days, 30 days, or any length of period in between. In one embodiment, the immune cells are contacted with one or more of said agents for between about 0.5 hour to about 2 hours, between about 1 hour to about 12 hours, between about 10 hours to about 2 days, between about 1 day to about 3 days, between about 2 days to about 5 days, between about 3 days to about 6 days, between about 5 days to about 8 days, between about 7 days to about 14 days, between about 12 days to about 22 days, between about 14 days to about 25 days, between about 20 days to about 30 days. In some embodiments, the immune cells are contacted with one or more of said agents for no less than 16 hours, 14 hours, 12 hours, 10 hours, 8 hours, 6 hours, 4 hours, 2 hours, or any length of time in between. As such, said sufficient length of time, for example, is no less than 15, 13, 11, 9, 7, 5, 3, or 1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, 90 hour(s).

The method of modulating a population or a subpopulation of immune cells suitable for adoptive cell-based therapies that comprises contacting the immune cells with a composition comprising at least one said agent, may further comprise enriching or isolating one or more desired subpopulations from the immune cells after the contact, wherein the one or more desired subpopulations comprise naïve T cell, stem cell memory T cell, central memory T cell, adaptive NK cell, or type I NKT cell.

In some embodiments, the immune cells for modulation are obtained from a subject who is CMV seropositive, or who has been previously administered genetically modified immune cells. In some embodiments, after modulation, the genetically modified immune cells obtained from a subject may be administered autologously or allogeneically. In some embodiments, the donor derived immune cells for modulation comprise an exogenous nucleic acid encoding a T Cell Receptor (TCR) and/or a Chimeric Antigen Receptor (CAR).

In some other embodiments, the isolated immune cells for modulation are genetically modified (genetically engineered or derived from rearrangements, mutations, genetic imprinting and/or epigenetic modification). In some embodiments, the isolated immune cells for modulation comprise at least one genetically modified modality as previously described. In some embodiments, the isolated population of immune cells are genomically engineered to comprise an insertion, a deletion, and/or a nucleic acid replacement. In some particular embodiments, the genomically engineered immune cells comprise an exogenous nucleic acid encoding a T Cell Receptor (TCR), a Chimeric Antigen Receptor (CAR), and/or overexpression of CD16 or a variant thereof.

Alternatively, the population of immune cells for modulation may be differentiated in vitro from stem cells, hematopoietic stem or progenitor cells, or progenitor cells; or trans-differentiated from non-pluripotent cells of hematopoietic or non-hematopoietic lineage. In some embodiments, the stem cells, hematopoietic stem or progenitor cells, progenitor cells, or non-pluripotent cells from which the immune cells for modulation are derived are genomically engineered to comprise an insertion, a deletion, and/or a nucleic acid replacement, which are also comprised in the derived immune cells therefrom. In some particular embodiments, the derived immune cells comprise an exogenous nucleic acid encoding a T Cell Receptor (TCR), a Chimeric Antigen Receptor (CAR), and/or overexpression of CD16 or a variant thereof.

IV. Therapeutic Use of the Modulated Immune Cells, Immune Cell Population or Subpopulations The present invention provides a therapeutic composition comprising an isolated population or subpopulation of immune cells that have been contacted, treated, or modulated with one or more modulating agents in an amount sufficient to improve the therapeutic potential of the immune cells, wherein the one or more modulating agents comprise at least a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, or a Syk inhibitor. In one embodiment, the contacted, treated, or modulated immune cells obtain at least one desirable therapeutic attributes including, but not limited to, increased cell expansion; increased number or relative ratio of one or more desired cell subpopulations; improved proliferation, cytotoxicity, or cell recall; and improved persistence, in comparison to immune cells without contacting the same agent(s). In some embodiments, the one or more modulating agents comprise at least one compound selected from Table 1, or derivatives or analogues thereof. In some embodiments, the one or more modulating agents comprise a BET inhibitor, an IKK inhibitor, a JAK inhibitor, a PDK1 inhibitor, a Raf inhibitor, or a Syk inhibitor. In some embodiments, the one or more modulating agents comprise at least a PDK1 inhibitor. In some other embodiments, the one or more modulating agents comprise at least a Raf inhibitor. In some other embodiments, the one or more modulating agents comprise at least a Syk inhibitor. In yet another embodiment, the one or more modulating agents comprise at least one of GSK2334470, AZ628, GDC-0879, Dabrafenib, R788, pacritinib, Bardoxolone methyl, and PRT062607. In one embodiment, the one or more modulating agents comprise at least GSK2334470. In another embodiment, the one or more modulating agents comprise at least AZ628. In yet another embodiment, the one or more modulating agents comprise R788. In some other embodiments, the composition of one or more modulating agents comprise Bardoxolone methyl.

In one embodiment, the isolated population or subpopulation of immune cells that has been contacted with one or more of said agents comprise an increased number or relative ratio of naïve T cells, stem cell memory T cells, and/or central memory T cells. In one embodiment, the isolated population or subpopulation of immune cells that has been contacted with one or more of said agents comprise an increased number or relative ratio of type I NKT cells. In another embodiment, the isolated population or subpopulation of immune cells that has been contacted with one or more of said agents comprise an increased number or relative ratio of adaptive NK cells.

Also provided herein is a combinational therapeutic composition comprising the modulated immune cells as disclosed and one or more therapeutic additives/agents. In some embodiments of the combinational therapeutic composition, the one or more therapeutic additives comprise a peptide, a cytokine, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD).

In some embodiments, the additional therapeutic agent comprises an antibody, or an antibody fragment. In some embodiments, the antibody may be a humanized antibody, a humanized monoclonal antibody, a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the modulated cells to better recognize and lysis of the target cell. In some embodiments, the antigen, as an additional therapeutic agent, activates the modulated NK cells to make use of antibody-dependent cellular cytotoxicity (ADCC). Monoclonal antibodies (mAbs) bind to the target cell plus engaging CD16 on NK cells and other cell types resulting in killing of tumor cell by ADCC both in vivo and in vitro. mAbs can also enhance ADCC and stimulate NK cells by blocking NK cell inhibition. In some embodiments, the NK cell mediated ADCC is through expressed CD16 and genetically engineered variants thereof by the modulated NK cells. The genetically engineered variants of CD16 include, but are not limited to, non-cleavable CD16, high affinity CD16 (haCD16), and high affinity non-cleavable CD16 (hnCD16). Additionally, the design of bi- and trispecific antibodies, fusing the Fab region of the antibody targeting the tumor cell antigen, such as the anti-CD19, CD20, and CD33 antigens, in combination with another Fab region recognizing CD16 on NK cell leads to stimulation of the NK cells followed by tumor cell killing. In some embodiments, the antibodies suitable for combinational treatment with modulated immune cells provided herein include, but are not limited to, anti-CD20 (retuximab, veltuzumab, ofatumumab, ublituximab, ocaratuzumab, obinutuzumab), anti-Her2 (trastuzumab), anti-CD52 (alemtuzumab), anti-EGFR (certuximab), and anti-CD38 (daratumumab), and their humanized and Fc modified variants.

In some embodiments, the additional therapeutic agent comprises one or more of a chemotherapeutic agent, a radioactive moiety, or an immunomodulatory drug.

Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art. In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, a vinca alkaloid, an epipodophyllotoxin, or an interleukin. Exemplary chemotherapeutic agents include, but are not limited to, cyclophosphamide, mechlorethamine, mephalin, chlorambucil, heamethylmelamine, thiotepa, busulfan, carmustine, lomustine, semustine, methotrexate, fluorouracil, floxuridine, cytarabine, 6-mercaptopurine, thioguanine, pentostatin, vincristine, vinblastine, vindesine, etoposide, etoposide orthoquinone, teniposide, daunorubicin, doxorubicin, mitoxantrone, bisanthrene, actinomycin D, plicamycin, puromycin, gramicidine D, paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topotecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's *The Pharmacological Basis of Therapeutics*, Ninth Edition, McGraw-Hill, N.Y., 1995) or through the National Cancer Institute website (fda.gov/cder/cancer/druglistfrarne.htm), both as updated from time to time. Immunomodulatory drugs (IMiDs) such as thalidomide, lenalidomide, and pomalidomide stimulate both NK cells and T cells. As provided herein, IMiDs may be used with the modulated therapeutic immune cells for cancer treatments.

The present invention also provides methods of treating a subject, i.e., inhibiting, preventing, ameliorating a condition, by using immune cells modulated with at least one of a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, an Lck inhibitor, a PDK1 inhibitor, a Raf inhibitor, and a Syk inhibitor, and optionally, by one or more additional therapeutic agents as described.

In one aspect, the modulated immune cells can be used to treat, prevent, or ameliorate hematological malignancies, solid cancers, precancerous conditions, autoimmune disorders, viral infections in a subject by introducing or administering the modulated immune cells to the subject suitable for adoptive cell therapy. In another aspect, the modulated immune cells can be used to enhance anti-tumor immune responses by introducing the cells to a subject in need of such a treatment.

The terms "treating," "treatment," are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of a disease or an injury. The treatment of ongoing disease, where the treatment stabilizes or reduces the undesirable clinical symptoms of the patient, is also of particular interest. In particular embodiments, the subject in need of a treatment has a disease, a condition, and/or an injury that can be treated, ameliorated, and/or improved in at least one associated symptom by a cell therapy. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g. a hyperproliferative disorder or a cancer of hematopoietic system, a subject having or at risk of developing a tumor, e.g., a solid tumor, a subject who has or is at risk of having a viral infection or a disease associated with a viral infection.

Examples of hematological malignancies include, but are not limited to, acute and chronic leukemias (acute myelogenous leukemia (AML), acute lymphoblastic leukemia (ALL), chronic myelogenous leukemia (CML), lymphomas, non-Hodgkin lymphoma (NHL), Hodgkin's disease, multiple myeloma, and myelodysplastic syndromes. Solid cancers include, but are not limited to, cancer of the brain, prostate, breast, lung, colon, uterus, skin, liver, bone, pancreas, ovary, testes, bladder, kidney, head, neck, stomach, cervix, rectum, larynx, and esophagus. Examples of various autoimmune disorders include, but are not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis *nodosa*, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's). Examples of viral infections include, but are not limited to, HIV-(human immunodeficiency virus), HSV- (herpes simplex virus), KSHV- (Kaposi's sarcoma-associated herpesvirus), RSV- (Respiratory Syncytial Virus), EBV- (Epstein-Barr virus), CMV-(cytomegalovirus), VZV (Varicella zoster virus), adenovirus-, a lentivirus-, a BK polyomavirus-associated disorders.

The therapeutic composition comprising the modulated immune cells as disclosed can be administered in a subject before, during, and/or after other treatments. As such the method of a combinational therapy can involve the administration or preparation of modulated cells before, during, and/or after the use of an additional therapeutic agent. As provided above, the one or more therapeutic additives comprise a peptide, a cytokine, a mitogen, a growth factor, a small RNA, a dsRNA (double stranded RNA), mononuclear blood cells, feeder cells, feeder cell components or replacement factors thereof, a vector comprising one or more polynucleic acids of interest, an antibody, a chemotherapeutic agent or a radioactive moiety, or an immunomodulatory drug (IMiD). The administration of the modulated immune cells can be separated in time from the administration of an additional therapeutic agent by hours, days, or even weeks. Additionally or alternatively, the administration can be combined with other biologically active agents or modalities such as, but not limited to, an antineoplastic agent, a non-drug therapy, such as, surgery.

Both autologous and allogeneic immune cells can be modulated and used in cell therapies as described above.

In some embodiments, the number of modulated immune cells in the therapeutic composition is at least $0.1 \times 10^5$ cells, at least $1 \times 10^5$ cells, at least $5 \times 10^5$ cells, at least $1 \times 10^6$ cells, at least $5 \times 10^6$ cells, at least $1 \times 10^7$ cells, at least $5 \times 10^7$ cells, at least $1 \times 10^8$ cells, at least $5 \times 10^8$ cells, at least $1 \times 10^9$ cells, or at least $5 \times 10^9$ cells.

In some embodiments, the number of modulated immune cells in the therapeutic composition is about $0.1 \times 10^5$ cells to about $1 \times 10^6$ cells; about $0.5 \times 10^6$ cells to about $1 \times 10^7$ cells; about $0.5 \times 10^7$ cells to about $1 \times 10^8$ cells; about $0.5 \times 10^8$ cells to about $1 \times 10^9$ cells; about $1 \times 10^9$ cells to about $5 \times 10^9$ cells; about $0.5 \times 10^9$ cells to about $8 \times 10^9$ cells, or any range in-between.

In some embodiments, the number of modulated immune cells in the therapeutic composition is about $0.5 \times 10^6$ cells to about $1 \times 10^6$ cells; about $0.5 \times 10^7$ cells to about $1 \times 10^7$ cells; about $0.5 \times 10^8$ cells to about $1 \times 10^8$ cells; about $0.5 \times 10^9$ cells to about $5 \times 10^9$ cells; about $1 \times 10^9$ cells to about $8 \times 10^9$ cells, or any range in-between.

In some other embodiments, the number of modulated immune cells in the therapeutic composition is about $0.1 \times 10^5$ cells to about $0.5 \times 10^6$ cells; about $0.5 \times 10^6$ cells to about 0.5×10$^7$ cells; about 0.5×10$^7$ cells to about 0.5×10$^8$ cells; about 0.5×10$^8$ cells to about 0.5×10$^9$ cells; about 0.5×10$^9$ cells to about 8×10$^9$ cells, or any range in-between.

In one embodiment, the number of modulated immune cells in the therapeutic composition is the number of immune cells in a partial or single cord of blood, or is at least 0.1×10$^5$ cells/kg of bodyweight, at least 0.5×10$^5$ cells/kg of bodyweight, at least 1×10$^5$ cells/kg of bodyweight, at least 5×10$^5$ cells/kg of bodyweight, at least 10×10$^5$ cells/kg of bodyweight, at least 0.75×10$^6$ cells/kg of bodyweight, at least 1.25×10$^6$ cells/kg of bodyweight, at least 1.5×10$^6$ cells/kg of bodyweight, at least 1.75×10$^6$ cells/kg of bodyweight, at least 2×10$^6$ cells/kg of bodyweight, at least 2.5×10$^6$ cells/kg of bodyweight, at least 3×10$^6$ cells/kg of bodyweight, at least 4×10$^6$ cells/kg of bodyweight, at least 5×10$^6$ cells/kg of bodyweight, at least 10×10$^6$ cells/kg of bodyweight, at least 15×10$^6$ cells/kg of bodyweight, at least 20×10$^6$ cells/kg of bodyweight, at least 25×10$^6$ cells/kg of bodyweight, at least 30×10$^6$ cells/kg of bodyweight, 1×10$^8$ cells/kg of bodyweight, 5×10$^8$ cells/kg of bodyweight, or 1×10$^9$ cells/kg of bodyweight, or 8×10$^9$ cells/kg of bodyweight.

The modulated immune cells provided by the invention can be administered to a subject without being expanded ex vivo or in vitro prior to administration. In particular embodiments, the modulated population of immune cells can be washed to remove the modulating agent(s). In some embodiments, the isolated population of modulated immune cells derived hematopoietic lineage cells can be recombinantly produced to express TCR, CAR or other proteins.

The therapeutic compositions suitable for administration to a patient can include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, 17$^{th}$ ed. 1985, the disclosure of which is hereby incorporated by reference in its entirety).

In particular embodiments, therapeutic cell compositions having an isolated population of modulated cells also have a pharmaceutically acceptable cell culture medium, or pharmaceutically acceptable carriers and/or diluents. A therapeutic composition comprising a population of modulated immune cells as disclosed herein can be administered separately by intravenous, intraperitoneal, enteral, or tracheal administration methods or in combination with other suitable compounds to affect the desired treatment goals.

These pharmaceutically acceptable carriers and/or diluents can be present in amounts sufficient to maintain a pH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the pH of the therapeutic composition is in the range from about 4 to about 10. Alternatively, the pH of the therapeutic composition is in the range from about 5 to about 9, from about 6 to about 9, or from about 6.5 to about 8. In another embodiment, therapeutic composition includes a buffer having a pH in one of said pH ranges. In another embodiment, the therapeutic composition has a pH of about 7. Alternatively, the therapeutic composition has a pH in a range from about 6.8 to about 7.4. In still another embodiment, the therapeutic composition has a pH of about 7.4.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the modulated immune cells of the invention are suitable for use as a pharmaceutical cell culture medium. In particular embodiments, the pharmaceutically acceptable cell culture medium is a serum free, and/or feeder-free medium.

In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of media suitable for use in the present invention and that there are many suitable media known and available to those in the art.

EXAMPLES

The following examples are offered by way of illustration and not by way of limitation.

Example 1—Selected Compounds for Immune Cell Modulation

To assess the ability of the compound groups in Table 1 to impact T cells in immunotherapy, a number of in vitro systems and in vivo models were used and data were analyzed. The impact of individual compounds on naïve, stem cell memory, or central memory T cells were assessed in cells from additional donors. It was shown that each of the compounds in Table 1 positively affect treated T cells in at least one of the following aspects: (1) producing a higher proportion or greater absolute number of phenotypically identified naïve, stem cell memory, or central memory T cells; (2) improving target cell killing ability; (3) increasing cell survival and expansion; (4) increasing cytokine production; and (5) possessing in vivo efficacy, including increased ability in tumor clearance, improved cell persistence in vivo post-transfer, increased ability to reduce tumor burden, or increased ability to promote animal survival following challenge with high tumor dose.

In Vitro T Cell Culture.

Fresh leukopaks (AllCells, Alameda, Calif.; Key Biologics, Memphis, Tenn.) were obtained from healthy donors, from which T cells were negatively selected using, for example, the EasySep Human T Cell Enrichment Kit (Stem Cell Technologies, Vancouver, Canada). The freshly isolated T cells were aliquoted and cryopreserved. On the day the assays were initiated, T cells were thawed and washed into X-Vivo 15 with supplements including IL-2 and pen/strep. Cells were dispensed into flat-bottom 384-well plates at 5×10$^5$ cells/ml with anti-CD3/Anti-CD28 beads. Individual compounds were added at a final concentration over the range of 10 μM to 10 nM to each well from column 3 to column 22 of each plate. Positive and negative controls were added to additional wells. Cells were incubated for about 6 days at 37 degrees with 5% $CO_2$.

Phenotypic Profiling:

These studies were performed with T cells from healthy donors. Six days post-initiation of culture in the presence of anti-CD3/CD28 beads and compound addition, cells were harvested and stained with a fixable viability marker and fluorophore-conjugated antibodies: CD3, CD4, CD8, CD62L, CCR7, CD27, and Tim3 (BD Biosciences, San Jose, Calif.; and BioLegend, San Diego, Calif.). Fluorescent absolute counting beads (Spherotech, Lake Forest, IL) were added just prior to acquisition. Data acquisition was performed on a BD Fortessa™ X-20 (BD Biosciences) and data were analyzed using Treestar™ software (FlowJo, Ashland, Oreg.) and Spotfire (Tibco, Boston, Mass.). The expression of surface markers including CD62L, CCR7 and CD27 was used to identify naïve, stem cell memory, or central memory T cells. After the treatment with each of the compounds, the surface marker expression profile of the treated cells was evaluated along with characterization of cell proliferation and viability. Compounds were scored on expression of these individual Tcm markers as well as CD62L/CCR7 double positive cells. Gene expression scores were also obtained based on a panel of selected 12 genes (Table 2) that are maximally differentially expressed in CD8 Tcm cells relative to Tem.

Cytokine Production:

The ability of T cells to respond to a variety of stimuli can be important to their function. The capacity of T cells to produce multiple cytokines in response to non-specific stimulation is a measure of their 'multifunctionality'. To assess whether compounds affect this 'multifunctional' response, the ability of modulated T cells to produce interferon-γ (IFNγ), IL-2 and/or TNFα post-stimulation was determined. After $CD8^+$ T cell treatment with each of the selected compounds, cells were stimulated with a mixture of PMA/ionomycin for four hours. Following stimulation, cytokine production was measured using intracellular cytokine staining with antibodies recognizing these cytokines conjugated to different fluorophores. Fluorescence was measured using flow cytometry. Cell were defined as multifunctional if they produced two or more cytokines. The proportion of T cell subsets that produce specific single, double or triple cytokines was examined and compared to cells without modulation using a selected compound.

Cytotoxicity and Expansion after Antigen Exposure:

An informative clinical parameter that can in some contexts be indicative of likelihood of successful adoptive cell therapy in clinical trials is the ability and extent of expansion of the transferred cells in the patient post-treatment and/or persistence and continued function following initial expansion, e.g., in the context of continued exposure to antigen. The ability of engineered T cells to persist and continue expanding over multiple rounds of antigen stimulation can be indicative of such features and/or likelihood of in vivo function or clinical response. An in vitro serial killing/restimulation assay, where the T cells treated by each compound were evaluated for various functions, including expansion and ability to kill tumor cells expressing the target antigen in vitro over multiple rounds of exposure to and withdrawal from antigen, was used as a model system. Such assays were carried out on cells treated with or without compounds, to assess the impact of individual compounds on cell function after repeated encounter with antigen, and cell expansion or persistence in such contexts.

Metabolic Profiling:

The differential influence of the selected compounds on the metabolism of the treated T cells was described using oxygen consumption rate (OCR), a measure of mitochondrial respiration, reflecting one of the factors that could lead to an altered T cell functionality. After compound treatment, the OCR was determined using a Seahorse™ XFe96 system (Agilent Technologies, Santa Clara). To do this, the cells were washed and resuspended in non-buffered assay medium. The cells were then seeded in 96-well assay plates, and subjected to the Seahorse™ mitostress test assay. Basal OCR was measured, and Spare Respiratory Capacity (SRC) was determined based on the difference between basal OCR and maximal OCR following addition of the ionophore FCCP into the assay plate. The average SRC and basal OCR for two donors were obtained in this assay.

In Vivo Profiling:

To interrogate aspects of the functionality of compound-treated CAR-T cells, a $CD19^+$ xenograft model was used to characterize the ability of compound-treated CAR-T cells to clear tumor. $CD4^+$ and $CD8^+$ T cells were transduced with a vector containing a construct encoding the CAR and activated with anti-CD3/anti-CD28 beads. The $CD4^+$ and $CD8^+$ CAR-T cells were expanded separately in the presence of vehicle alone or compound in G-rex plates (Wilson-Wolf, St. Paul, Minn.). The $CD4^+$ and $CD8^+$ CAR-T cells were cryopreserved after 6 days of expansion. CAR-T cells were thawed, mixed at a 1:1 ratio of $CD4^+$ and $CD8^+$ CAR-T cells. A suboptimal therapeutic dose (~$2.5 \times 10^5$) of compound-treated CD19 directed CAR-T cells was administered to the NSG mice bearing Nalm-6-luc $CD19^+$ disseminated tumors. Tumor burden was measured based on the total radiance measured in each mouse which is dependent upon the amount of luciferase which is expressed by the Nalm-6-luc $CD19^+$ tumor cells.

Comprehensive compound evaluation regarding all aspects above are presented in FIGS. 8A-C according to the assays and data further detailed in the following examples. As provided herein, BET inhibitor, CDK inhibitor, CRAC channel Ca entry blocker, cyclooxygenase inhibitor, dopamine antagonist, ERK5/BMK1 inhibitor, Glucocorticoid, IGF-1R inhibitor, IKK inhibitor, JAK inhibitor, Lck inhibitor, PDK-1 inhibitor, Raf inhibitor, and Syk inhibitor are useful for modulating T cells for adoptive immunotherapies, wherein the modulated T cells have at least one desired characteristic associated with a therapeutic advantage, wherein such characteristics comprise: a higher proportion of naïve, stem cell memory, or central memory T cells; improved target cell killing ability; and increased potency, survival, expansion or persistence.

Example 2—Phenotypic Profiling of T Cells Under Treatment with Selected Compound Groups T cell subsets include Tcm, naïve (Tn), effector memory (Tem) and CD45RA+ effector memory (Temra) cells. Tn and Tcm cells are the least differentiated and have the greatest proliferative potential while Temra cells are the most fully differentiated, have poor proliferative potential but strong effector function (D'Asaro et al. 2006). Studies in both non-human primate and NOD/Scid IL-2RγCnull (NSG) mouse models have demonstrated that T cells with a central memory (Tcm) phenotype have improved persistence after adoptive transfer (Berger et al. 2008; Wang et al. 2011). In addition, CAR-expressing CD4 and CD8 central memory T cell (Tcm) subsets were administered to Non-Hodgkin lymphoma patients after hematopoietic stem cell transplantation, and the Tcm-derived CAR-T cells demonstrated improved expansion, indicating that Tcm may have a therapeutic advantage in treatment of human cancers.

The selected groups of compounds were assessed for their ability to skew T cell phenotype. The ability of a compound to produce a higher proportion or greater absolute number of phenotypically central memory T cells (Tcm) is one indicator of a compound's ability to skew T cell phenotype. Tcm is characterized herein by expression of both CCR7 and CD62L. The expression of either CD62L or CCR7 on T cells, as indicative of the desired T cell subsets, indicates a favorable functional characteristic for CAR-T cell therapy, and potentially other adoptive T cell therapies. The phenotypic studies use flow cytometry to measure the expression levels of these key surface proteins. Compounds were scored on expression of these individual Tcm markers as well as CD62L/CCR7 double positive cells (FIG. 1A). The scores in FIG. 1A were generated using the values obtained from four donors and the formula:

Score=Normalized StDev over Vehicle×Significance (−log 10(p-value))+1

Scores for other graphs in this figure used the same formula.

Figure 2A:
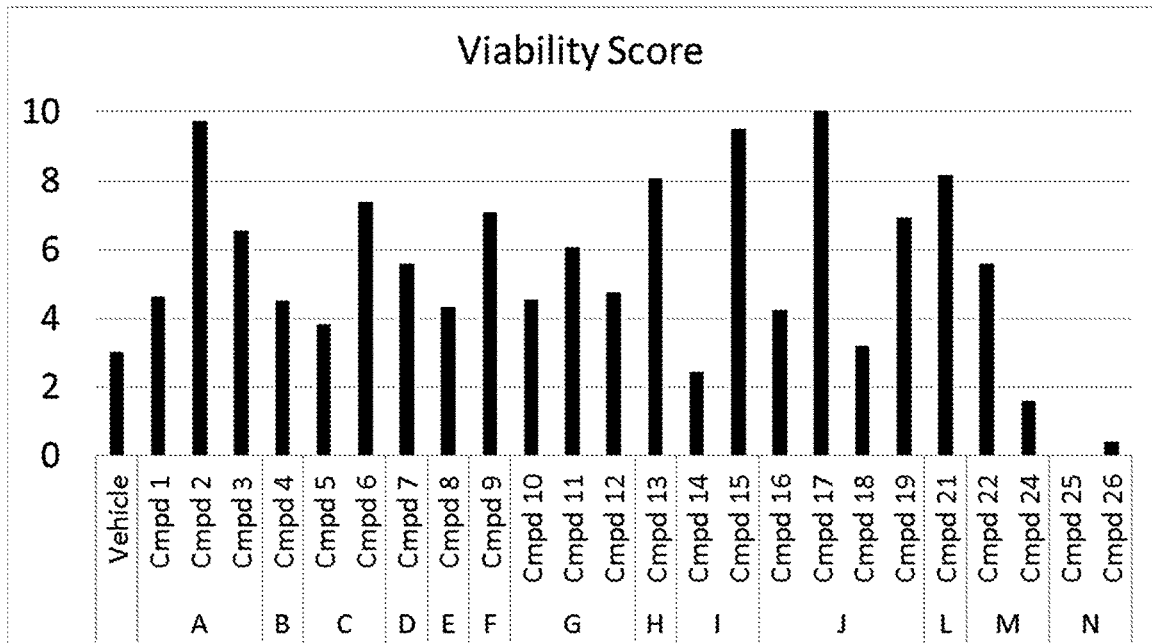
FIGS. 2A-C show that treatment using selected compounds impacts viability and expansion of the T cells: (A) viability score; (B) expansion score (refer to Table 1 for compound number and compound category); and (C) PDK1 inhibitor treatment improves expansion of CD8+ CAR-T cells (n=5 donors).
Figure 2B:
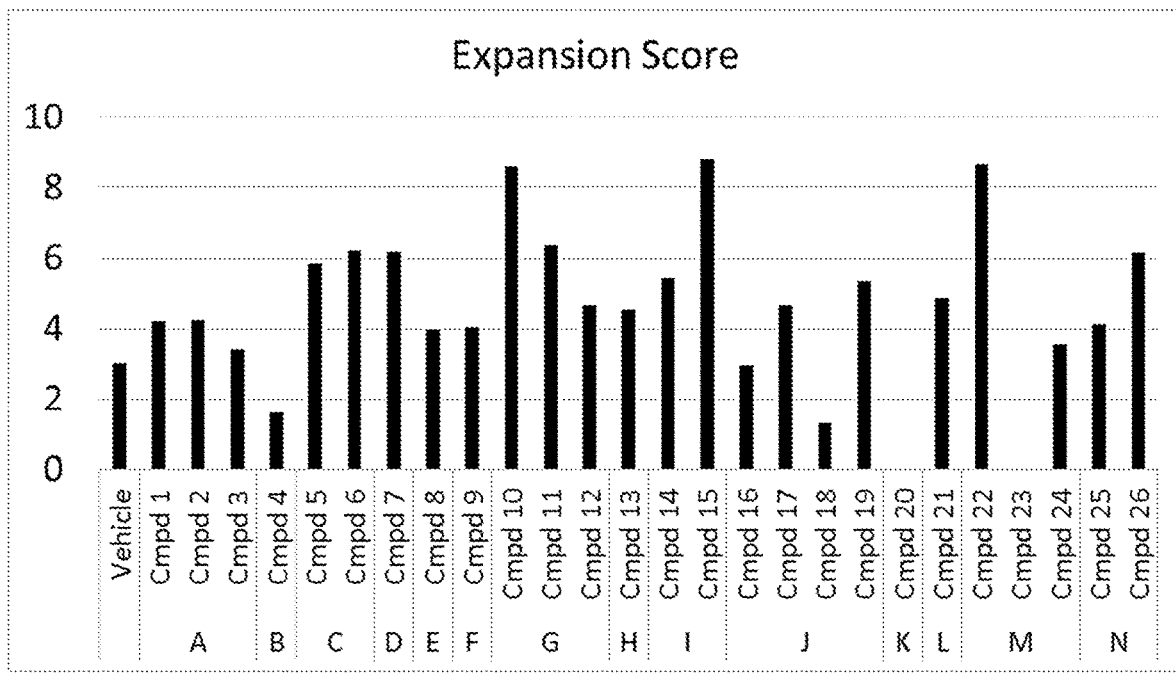

The phenotypic studies of the surface markers also included characterization of cell viability (FIG. 2A) and cell expansion (FIG. 2B). Scores for the graphs in FIGS. 2A-B were obtained using the formula:

(Test value−minimum value)/(maximum value−minimum value)×10

As shown in FIG. 1A, compound groups including BET inhibitor, IKK inhibitor, JAK inhibitor, PDK1 inhibitor, Raf inhibitor and Syk inhibitor produce a favorable Tcm phenotype. For example, a PDK1 inhibitor (for example, compound 21) increases the percentage of CCR7, CD62L double positive cells by approximately 7 fold relative to the vehicle, DMSO; while Dabrafenib, a Raf inhibitor (for example, compound 24), increases the percentage of Tcm by about 10 fold. On the other hand, although some selected compounds have minimal effect on improving Tcm percentage, such as the cyclooxygenase inhibitor (etoricoxib), dopamine antagonist (Sertindole), and glucocorticoids (flunisolide, dexamethasone acetate, amcinonide), they act to enhance cell viability and/or expansion relative to vehicle treatment (FIGS. 2A, 2B, and 8A-C).

Figure 1B:
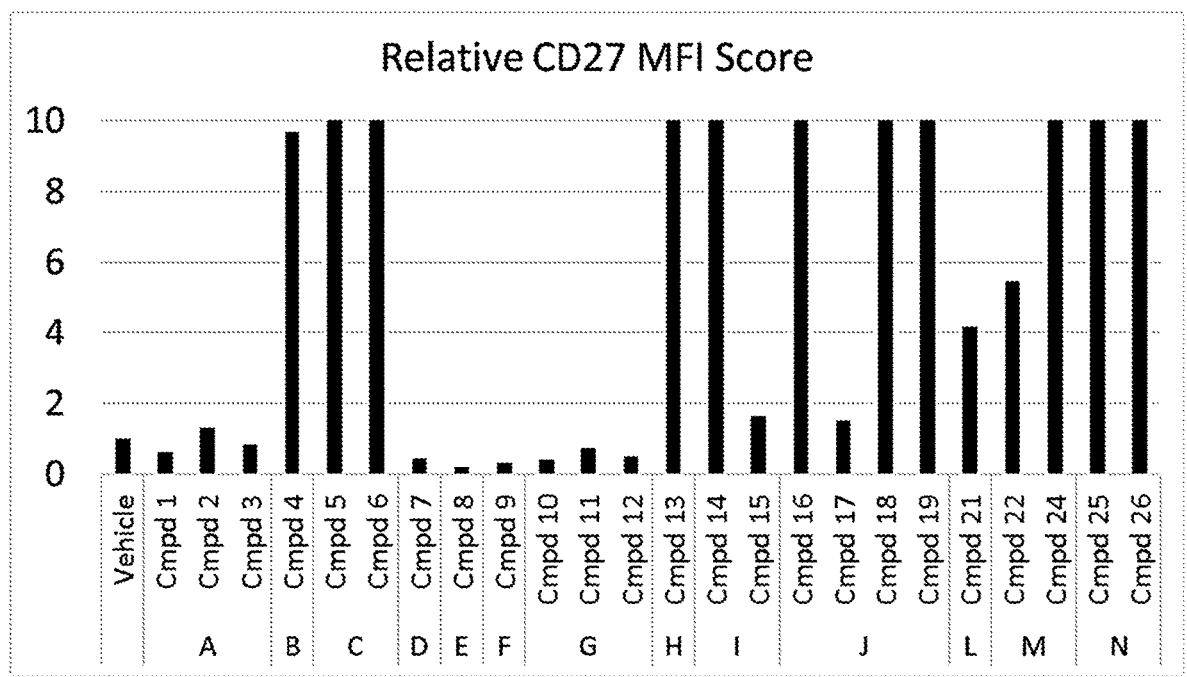

Further desired phenotypic properties include increased expression of CD27 (FIG. 1B). CD27 is a T cell costimulatory molecule with roles in T cell maturation and memory (Hendriks et al. 2000). As such, compounds that positively impact both the memory cell phenotype (CCR7-CD62L double positive or CD27 expression) and cell viability/expansion include the following: BET inhibitor, CRAC channel Ca entry blocker, ERK5/BMK1 inhibitor, IGF-1R inhibitor, IKK inhibitor, JAK inhibitor, PDK1 inhibitor, Raf inhibitor, and Syk inhibitor (FIGS. 1A, 1B, 2A, 2B, and 8A-C).

Figure 2C:
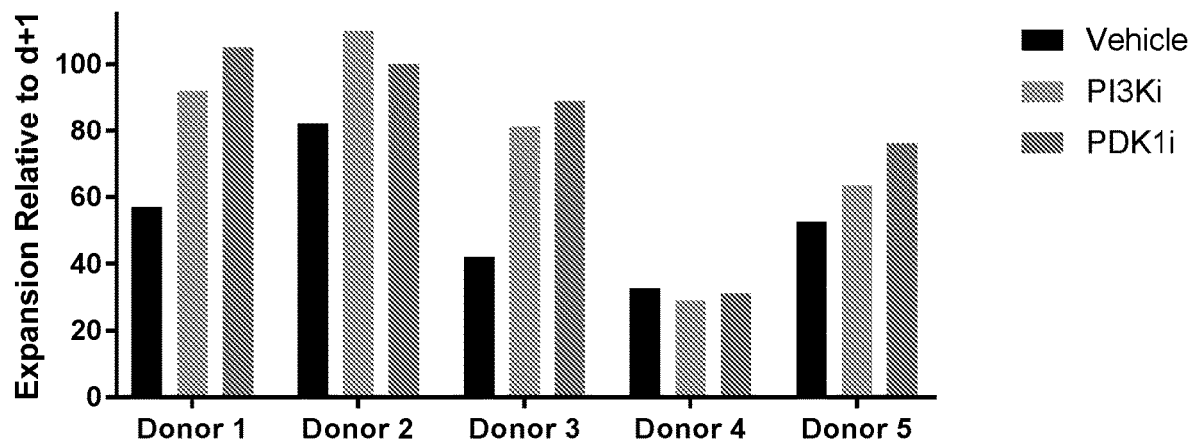

To further confirm PDK1 inhibitor's ability to enhance CAR-T cell expansion, CAR-T cells were generated in the presence of vehicle (DMSO), PI3K inhibitor, or PDK1 inhibitor. Compounds were added at the time of transduction, one-day post-activation with anti-CD3/CD28 beads, and the cells were cultured for a further six days. CAR-T cells were prepared from 5 healthy donors. After harvesting, the expansion of CD8+ CAR-T cells was assessed with counting beads on the flow cytometer. As shown in FIG. 2C, in 4 out of 5 donors, treatment with PDK1i significantly improved the expansion of CD8+ CAR-T cells in comparison to vehicle treatment, and overall had comparable, if not better, performance in expanding CAR-T cells relative to PI3K inhibitor treated CAR-T cells.

Figure 1C:
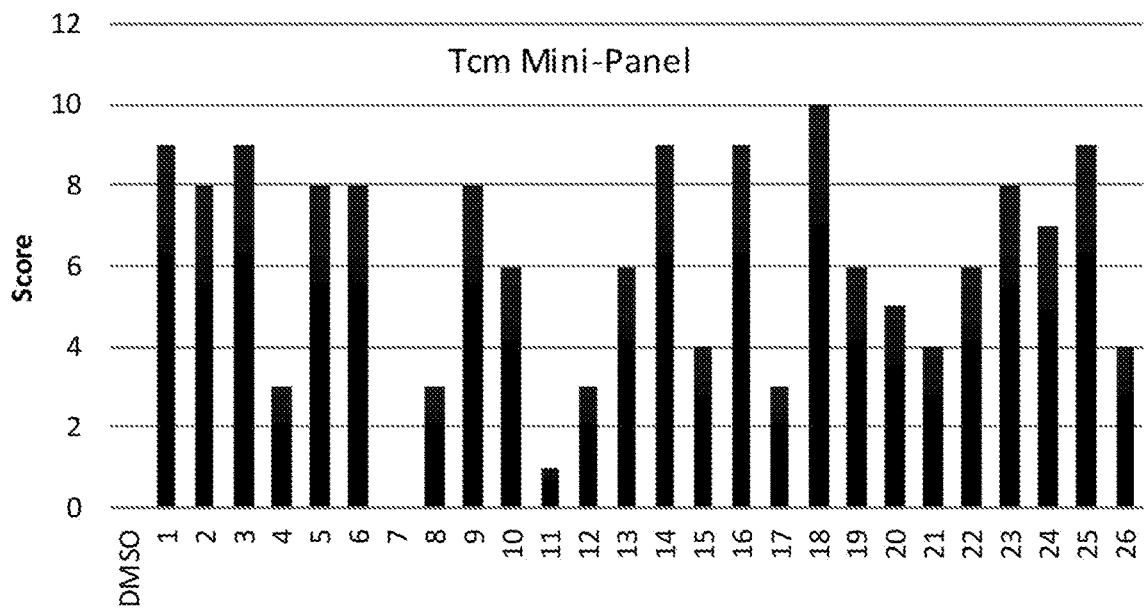

A unique panel of 96 genes chosen based on their differential expression across different T-cell subsets (Tn, Tscm, Tcm, Tem and Teff) was further employed to determine or confirm T cell phenotype skewing after compound treatment. Of special interest are a group of 12 genes (Tcm mini-panel) that include CCR7, SELL, CD27, LEF1, ICOS, NELL2, TESPA1, PRKCA, BACH2, TCF7, FAM129A, and LRNN3, which are maximally differentially expressed in CD8 Tcm cells relative to Tem (Table 2). Consistent with the findings based on CD62L, CCR7 and CD27 surface marker expression, many compounds' ability to greatly enhance the Tcm phenotype relative to vehicle was further confirmed by the Tcm mini-panel score, which provides a comprehensive evaluation of cell phenotype skewing capability of a given compound using marker gene expression (FIG. 1C).

TABLE 2

Genes in Tcm Mini-Panel

| | Gene | Protein Name | UniProtKB/Swiss-Prot Entry Identifier |
|---|---|---|---|
| 1 | TCF7 | Transcription factor 7 | P36402 |
| 2 | CD27 | CD27 antigen | P26842 |
| 3 | LEF1 | Lymphoid enhancer-binding factor 1 | P27782 |
| 4 | SELL | L-selectin | P14151 |
| 5 | CCR7 | C-C chemokine receptor type 7 | P32248 |
| 6 | ICOS | Inducible T-cell costimulator | Q9Y6W8 |
| 7 | NELL2 | Protein kinase C-binding protein NELL2 | Q99435 |
| 8 | TESPA1 | Thymocyte-expressed positive selection-associated protein 1 | A2RU30 |
| 9 | PRKCA | Protein kinase C alpha type | P17252 |
| 10 | BACH2 | Transcription regulator protein BACH2 | Q9BYV9 |
| 11 | FAM129A | Cell growth-inhibiting gene 39 protein | Q9BZQ8 |
| 12 | LRNN3 | Leucine-rich repeat neuronal protein 3 | Q9H3W5 |

As shown in FIG. 1C, all but one compound tested (compound 7 was not tested) have an increased Tcm mini-panel score relative to vehicle. Those compound groups leading to the highest Tcm mini-panel scores include BET inhibitor, CRAC channel Ca entry blocker, ERK5/BMK1 inhibitor, IKK inhibitor, JAK inhibitor, Raf inhibitor, and Syk inhibitor (FIG. 8B, column 5).

Figure 1D:
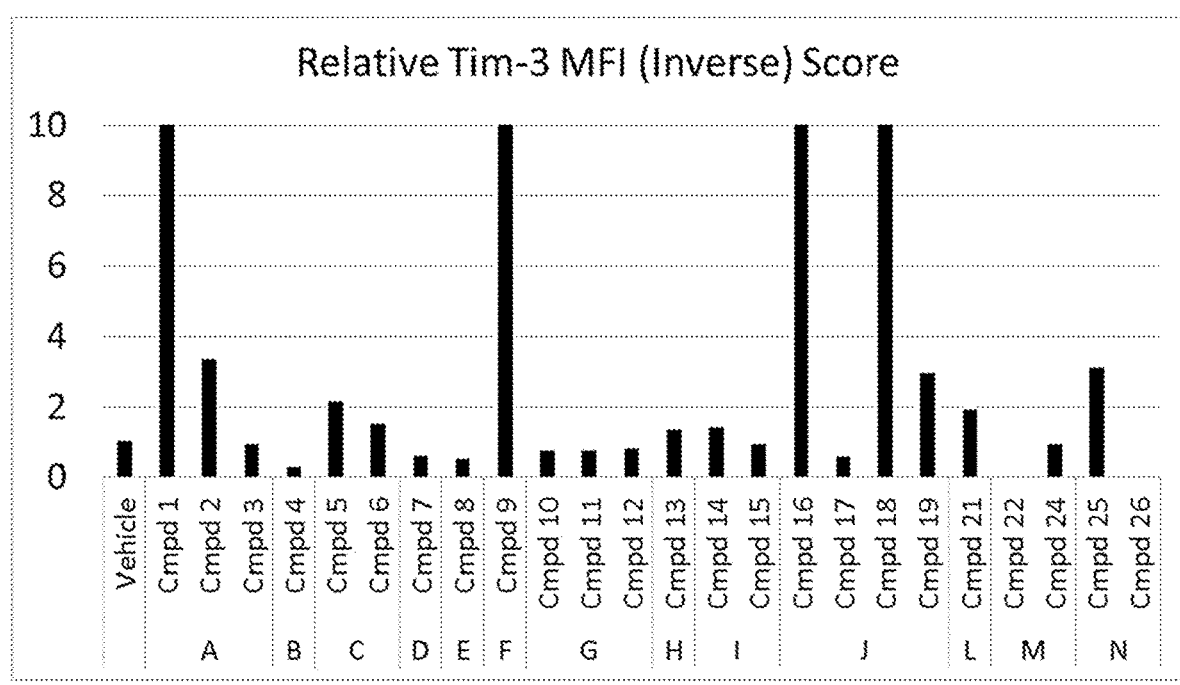

To determine the effect of compound treatment of T cells on exhaustion marker expression, cells from four different donors were prepared and treated by each compound of Table 1, and then stained for Tim-3 expression (UniProtKB/Swiss-Prot Entry Identifier: Q8TDQ0) by flow cytometry. T cell exhaustion is characterized by poor effector cell function and increased expression of exhaustion markers including PD-1 and Tim-3. T cell dysfunction due to 'exhaustion' is a state that can preclude adequate control of cancer or infection. Therefore, strategies that result in decreased exhaustion marker expression are desirable in cells for adoptive therapies. As shown in FIG. 1D, multiple compounds reduce Tim-3 expression as compared to vehicle. Scores for Tim-3 expression in FIG. 1D are presented as the inverse of the Tim-3 expression; thus a 10 exemplifies much lower expression while a 1 defines the higher expression observed with vehicle-treated cells. An enhanced reduction in Tim-3 expression was most markedly observed in treatments with BET inhibitor, CRAC channel Ca entry blocker, ERK5/BMK1 inhibitor, JAK inhibitor, PDK1 inhibitor, or Syk inhibitor. The data herein indicate that treating T cells with these inhibitors enhances T cell anti-tumor capability by reducing cell exhaustion that contributes to immune dysfunction.

According to the above analyses, all compounds in Table 1 are capable of at least one of the following: increasing Tcm percentage, improve cell viability/expansion, or reducing cell exhaustion. BET inhibitor, CRAC channel Ca entry blocker, ERK5/BMK1 inhibitor, IGF-1R inhibitor, IKK inhibitor, JAK inhibitor, PDK1 inhibitor, Raf inhibitor and Syk inhibitor appear to be particularly advantageous in enhancing T cell immune therapies for improving multiple desired phenotypic features of the treated T cells (FIG. 8A-C).

Example 3—Cytokine Production by T Cells Treated with the Selected Compounds

The ability of T cells to respond to a variety of stimuli is important for their function. The capacity of T cells to produce multiple cytokines in response to non-specific stimulation is a measure of their "multifunctionality". To assess whether selected compounds affect this "multifunctional" response in view of their phenotype skewing effect on the treated cells, the ability of treated cells to produce interferon-γ (IFNγ), IL-2 and TNFα post-stimulation was determined. After treatment of CD8+ T cells with a compound from Table 1, cells were stimulated with a mixture of PMA/ionomycin for four hours. Following stimulation, cytokine production was measured by intracellular cytokine staining with fluorescence-emitting antibodies recognizing these cytokines conjugated to different fluorophores. Fluorescence was measured using flow cytometry. Cells were defined as multifunctional if they produced at least two of the three cytokines.

Figure 3A:
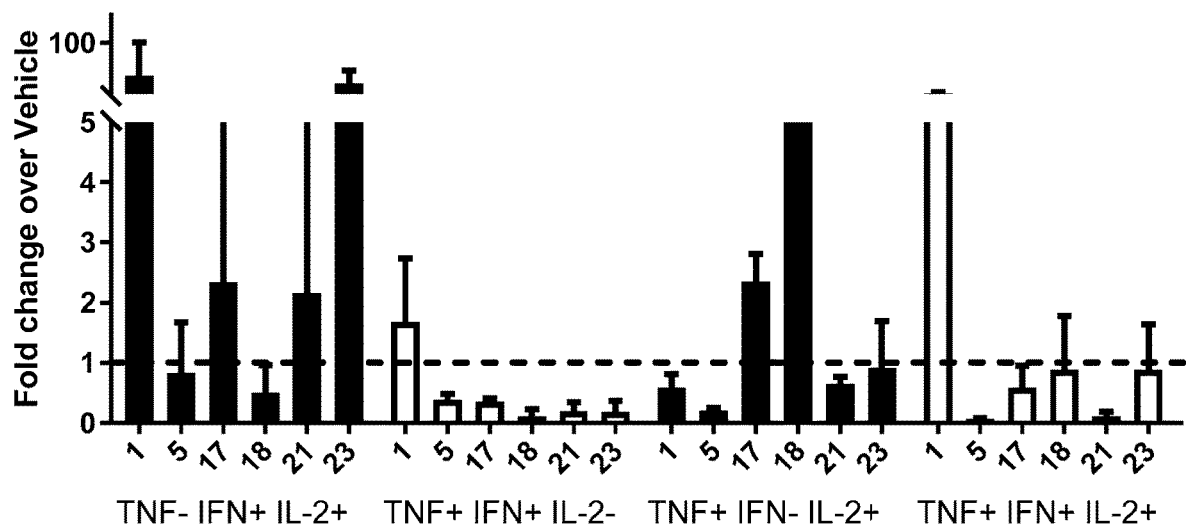
FIGS. 3A-D show that treatment using selected compounds impacts cytokine expression profile (TNFα, IFNγ or IL-2) of the T cells: (A) fold change of different subpopulations that are double or triple positive in selected cytokines; (B) fold change of subpopulations that produce at least 2 cytokines (FC: folder change); (C) fold change of different subpopulations that are single-positive in selected cytokines; and (D) fold change of different subpopulations that are single-, double- or triple positive in selected cytokines (refer to Table 1 or FIG. 3D for compound number and compound category).
Figure 3B:
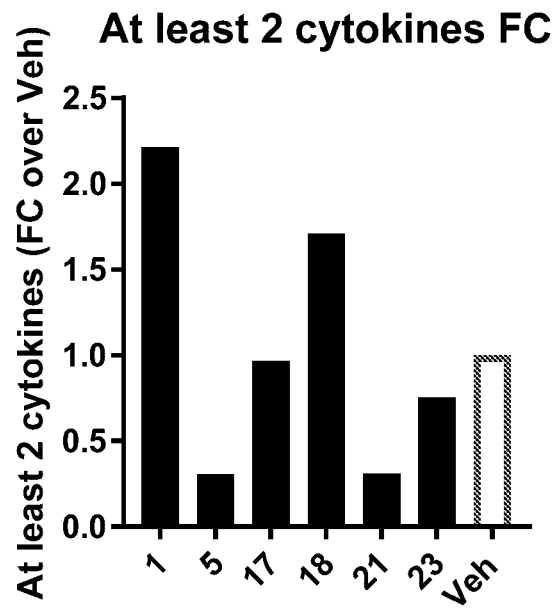
Figure 3C:
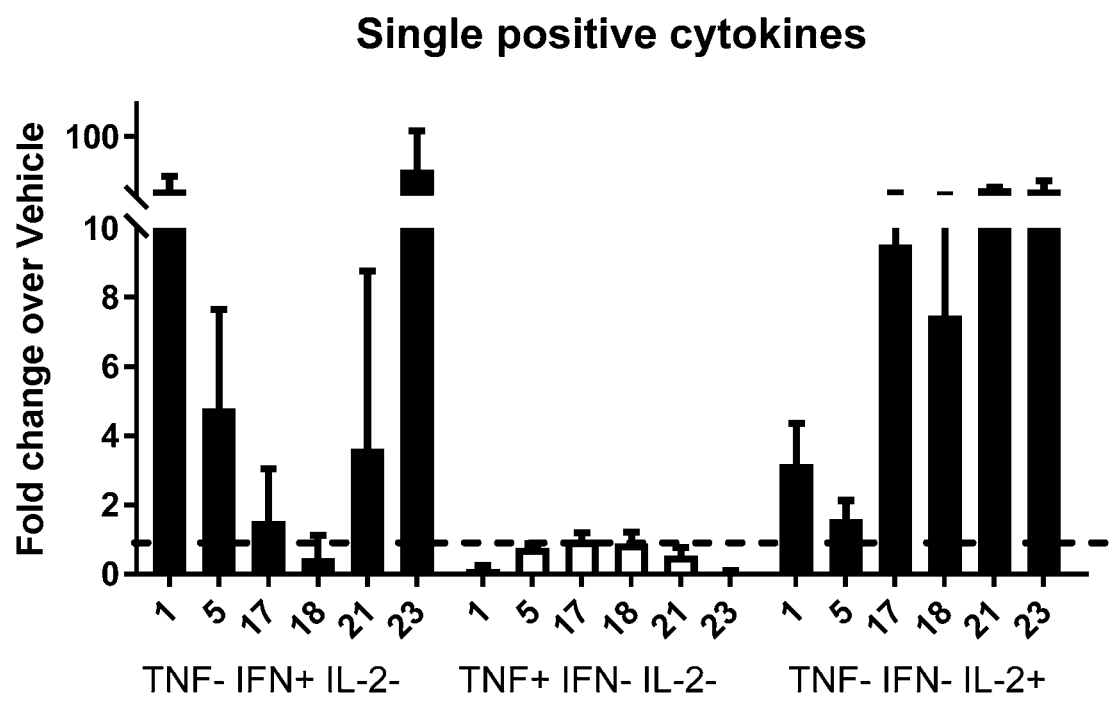
Figures 3D, 4A:
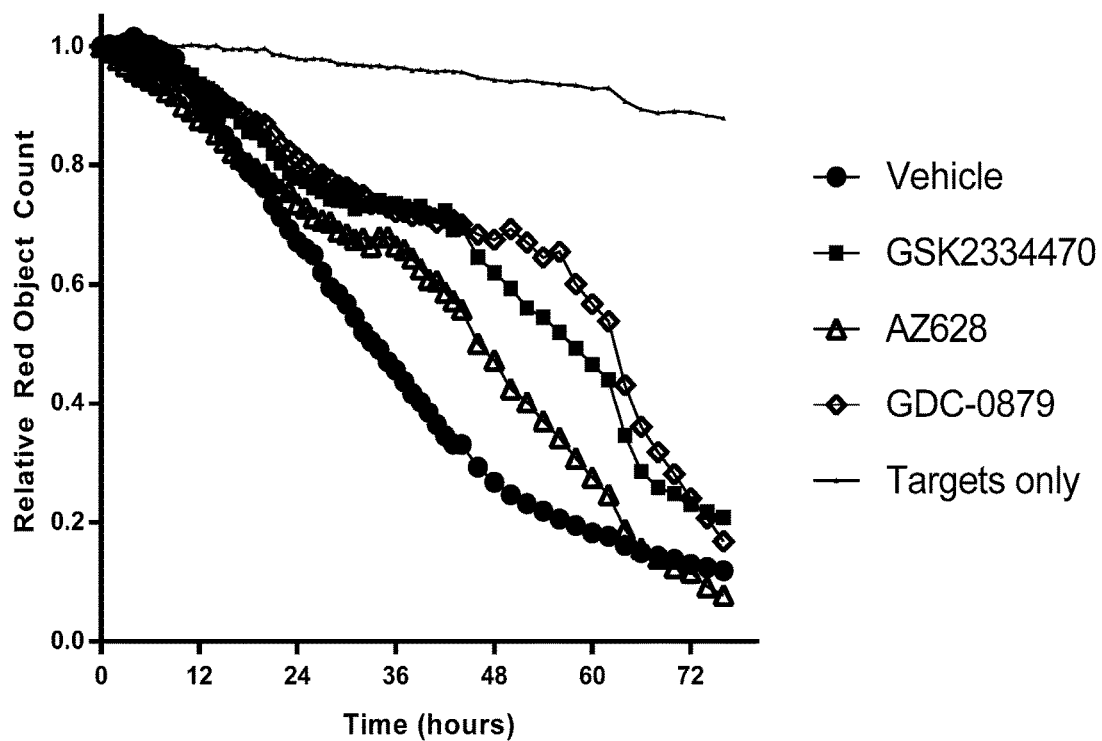
FIGS. 4A-B show compound-treated CAR-T cells can kill irradiated K562 cells expressing CD19 and mKate2: (A) target cell clearance over time by T cells treated with their respective selected compounds based on the relative red object count indicative of the loss of mKate2 labeled K562 cells; and (B) relative AUC (Area Under the Curve) for target cell killing (refer to Table 1 for compound number and compound category).

As can be seen in FIG. 3A for the 6 compounds tested, 5 maintained multifunctionality greater than vehicle. Treatment of the T cells with OTX015, a BET inhibitor, increased the total multifunctional subpopulation by nearly 16 fold, with the increase of cells producing all three cytokines being almost 13 fold (FIGS. 3A, 3B and 3D). Interestingly, all tested compounds also significantly increased the subpopulation of T cells producing a single cytokine: either IFNγ or IL-2 (FIG. 3C). For example, the IFNγ+ only subpopulation increased by about 33, 116 and 10 fold after the treatment with OTX015 (BET inhibitor), AZ628 (Raf inhibitor) and GSK2334470 (PDK1 inhibitor), respectively; whereas the IL-2 only subpopulation increased by about 11, 4, 19 and 18 fold after treatment with Pacritinib (JAK inhibitor), Tofacitinib (JAK inhibitor), GSK2334470 and AZ628, respectively (FIG. 3D). In addition, almost all of the compounds reduced the TNF+ IFN+ double positive population (FIGS. 3A and 3D). Without being limited by theory, the overall increase in the single cytokine (IFNγ or IL-2) producing subpopulation and reduction in the double positive TNF+ IFN+ producing subpopulation may be explained by, among other reasons, the cell phenotype skewing towards central memory T cells. For example, Tcm are predominantly quiescent, secreting IL-2 but not effector cell lineage cytokines (Pepper et al., Nat Immunol. 2011, 12(6): 467-471; Flynn et al., Clin. Trans. Immunol. 2014, 3(7): e20-. Doi: 10.1038/cti.2014. 16; Mahnke et al., Eur. J. Immunol. 2013, 43: 2797-2809).

Example 4—Compound-Treated T Cells Show Improved Expansion in a Serial Re-Stimulation Assay while Killing Target Cells An in vitro serial killing/re-stimulation assay, where CAR-T cells are tested for the ability to "clear" tumor cells in vitro over multiple rounds, can be used as a model to assess CAR-T expansion in the presence of tumor cells that express the antigen recognized by the CAR.

CD8 T cells were transduced with CARs and the cells were then cryopreserved. After thawing, the CAR-T cells were co-cultured with irradiated K562 tumor cells that express transgenic mKate2, a far-red fluorescent protein, and CD19, the antigen recognized by the CAR. Expression of Thy1.1 in the CD19BBz CAR-T cells and mKate2 in the target cells allow easy and reliable identification and counting of both cell populations in the serial killing assay. Prior to starting each round of killing, cell numbers were adjusted to the same total number of CAR-T cells and the same ratio of CAR-T cell to K562 target cell across the CAR-T cell cultures generated from different treatments using each of the compounds in Table 1.

CAR-Ts treated with vehicle (DMSO only), a PDK1 inhibitor (GSK2334470), a Raf inhibitor AZ628, or another Raf inhibitor GDC-0879 are included in FIG. 4A as an illustration. FIG. 4A shows data generated from an IncuCyte™ (Essen Bioscience, Ann Arbor) instrument which takes images over time and counts the mKate2-expressing target cells that are co-cultured with or without CAR-T cells, and the CAR-T cells that are vehicle- or compound-treated. When cultured in the absence of CAR-T cells, irradiated target cells alone show an ~10% decrease in number over time. However, addition of CAR-T cells results in a much faster decrease in target cell numbers. The compound treated cells, like the untreated CAR-T cells, can still recognize and lyse the K562 target cells. Although the kinetics of target cell killing for compound-treated cells was slower than for vehicle at earlier time points (24 to 65 hours), as illustrated, a similar number of target cells remained after 72 hours for both vehicle and compound treated CAR-T cells (FIG. 4A). With longer incubation time, target cells were fully cleared by all compound treated T-cells (data not shown). The slower killing kinetics observed for many of the compound-treated cells can be advantageous in the clinic by reducing certain side effects of tumor cell killing including cytokine release syndrome. The analyses also showed that the decrease in target cell number is CD19-dependent, as K562 target cells that do not express CD19 were not killed by the CD19BBz CAR-T cells (not shown), demonstrating that the compound treatments do not change T-cell antigen specificity.

Figure 4B:
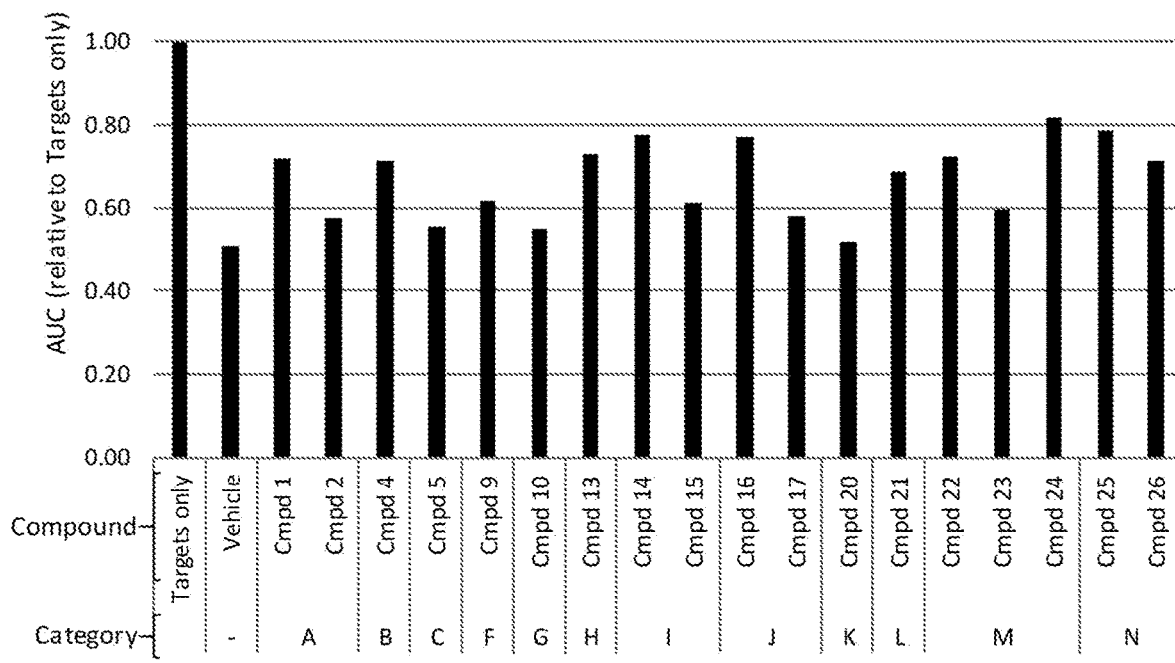

The reduction of target cell numbers over time can be plotted from the data acquired using the Incucyte as shown in FIG. 4A. From this, the Area Under the Curve (AUC) for CAR-T cells treated with each compound can be calculated. AUC reflects the potency (killing ability) of the T-cell under different treatments, which is affected by both the killing rate and the length of time it takes to clear the target cell. To determine the effect of compound treatment on the killing ability of CAR-T cells, the AUC relative to target cells alone was determined. As shown in FIG. 4B, the AUC for target cells only is set to 1.00, resulting in target cells co-cultured with vehicle-treated T cells having a relative AUC of 0.50. The relative AUC for T-cells treated with additional compounds in Table 1 are also shown in FIG. 4B. Interestingly, at the start of the serial killing/re-stimulation assay, most of the compound-treated CAR-T cells seem to have a larger AUC in comparison to that of untreated CAR-T cells, indicative of a decreased potency at least in the first round of killing. The compound-treated CAR-T cells, however, were able to clear the target cells over multiple rounds. Without being limited by theory, this may be explained by the observation that these compounds maintain a population of less differentiated, younger (or memory-like) T cells, which may not be as potent as a more differentiated T cell possessing full effector function at first. As shown in the examples above, this notion is consistent with the observations in phenotype profiling, and expansion ability of these treated cells.

Figure 5A:
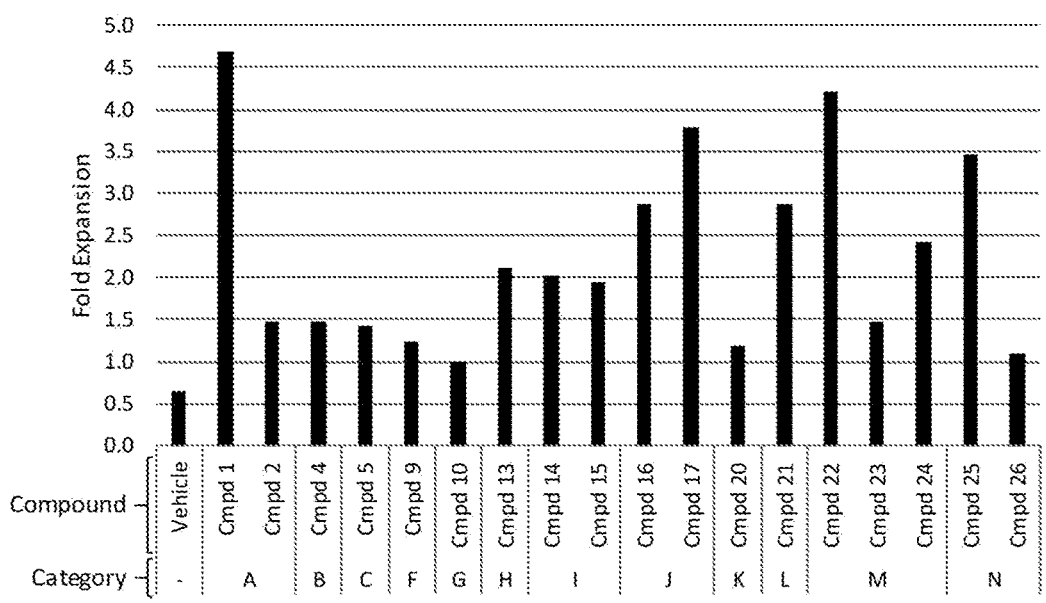
FIGS. 5A-C show improved T cell expansion at the end of round 3 and round 4 in a serial re-stimulation assay with irradiated target cells: (A) fold expansion of cells in round 3; (B) fold expansion of cells in round 4; and (C) total cell expansion over 4 rounds of target cell stimulation (refer to Table 1 for compound number and compound category).
Figure 5B:
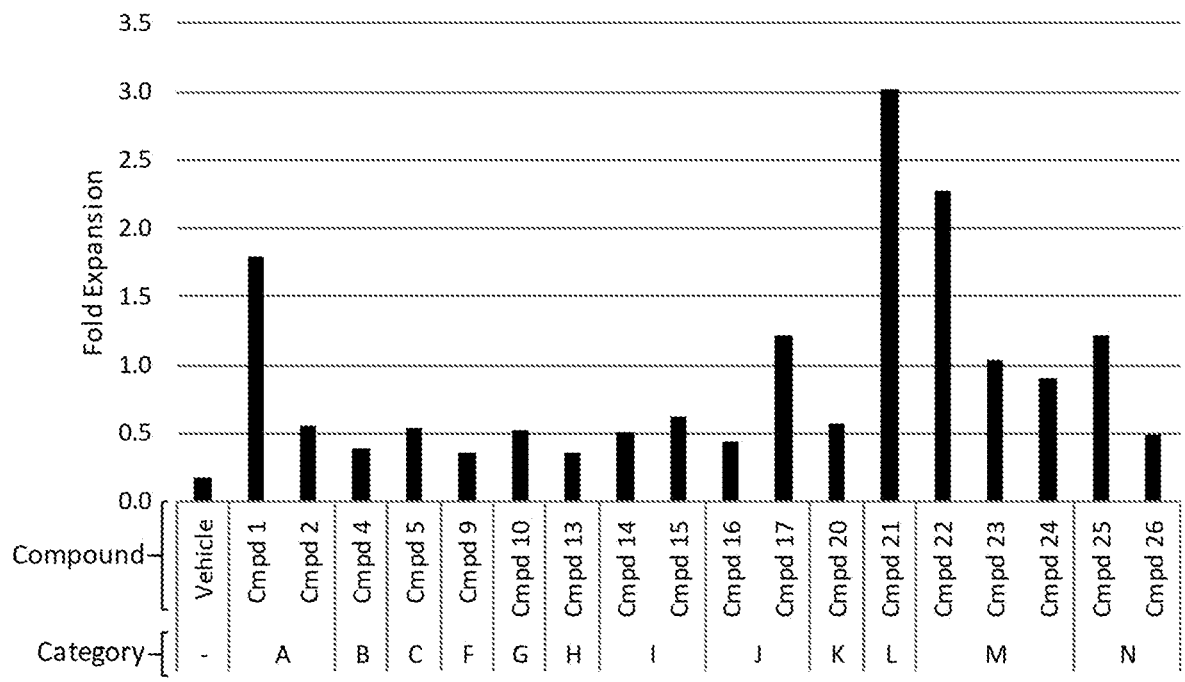
Figure 5C:
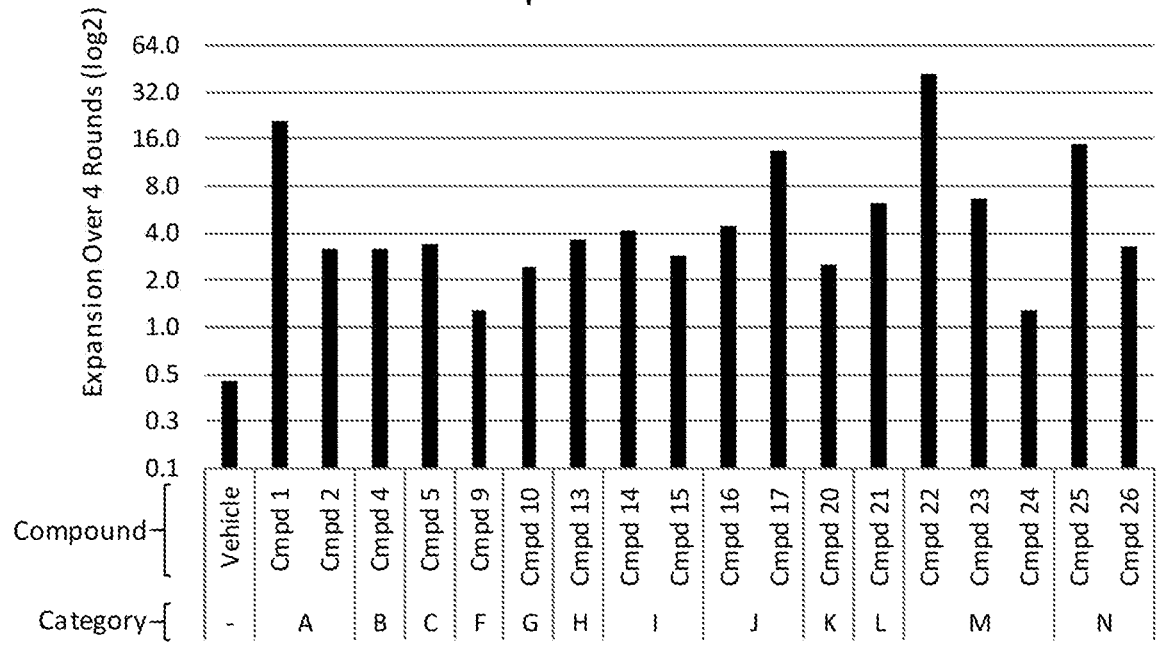

Further, a serial re-stimulation assay was deployed to evaluate the expansion capability of the treated T cells during target cell killing. It is shown that by round 3 and round 4 of the serial re-stimulation assay, the expansion in cell number of compound-treated CAR-T cells is much higher compared to the vehicle control, which show significantly decreased expansion (FIGS. 5A and 5B). Therefore, treatment with the classes of agents exemplified by the compounds in Table 1 enables increased expansion of the T cells through multiple rounds of killing/re-stimulation. The total expansion in CAR-T cell number through all 4 rounds under each compound treatment was also determined, and all the treated CAR-T cells showed greater expansion compared to the vehicle control (FIG. 5C). Taken together, these data show that compound treatment can confer the desirable effect of continued and increased expansion of treated T cells despite multiple exposure to target tumor cells. The killing ability along with cell expansion presented over a longer period is indicative of cell persistence, in addition to reduced risk of cytokine release syndrome due to rapid tumor cell killing. The relative scoring of all selected compounds of Table 1 based on the serial re-stimulation and killing assays are further summarized in FIG. 8C, columns 9-12. As shown, BET inhibitor, JAK inhibitor, PDK1 inhibitor, Raf inhibitor, and Syk inhibitor have the most consistent and the highest level of impact on improving T cell expansion under re-stimulation while maintaining the target cell killing ability and specificity.

Example 5—Metabolic Profile Alterations of T Cells Under Treatment with Selected Groups of Compound Cells generally utilize two major energy pathways, glycolysis and oxidative phosphorylation. It has been shown that mitochondrial spare respiratory capacity (SRC), which is the extra capacity available in cells to produce energy in response to increased stress or work, is increased in T memory cells but not in T effector cells, such as Temra (van der Windt and Pearce 2012). However, increased SRC and the reliance on oxidative phosphorylation may not be essential for memory CD8+ T cells (Phan et al. 2016). Despite the differences observed in publications by Van der Windt and Pearce and Phan et al., it is clear, from these publications as well as from the observations herein, that changes in T cell metabolism are linked to T cell function.

Figure 6A:
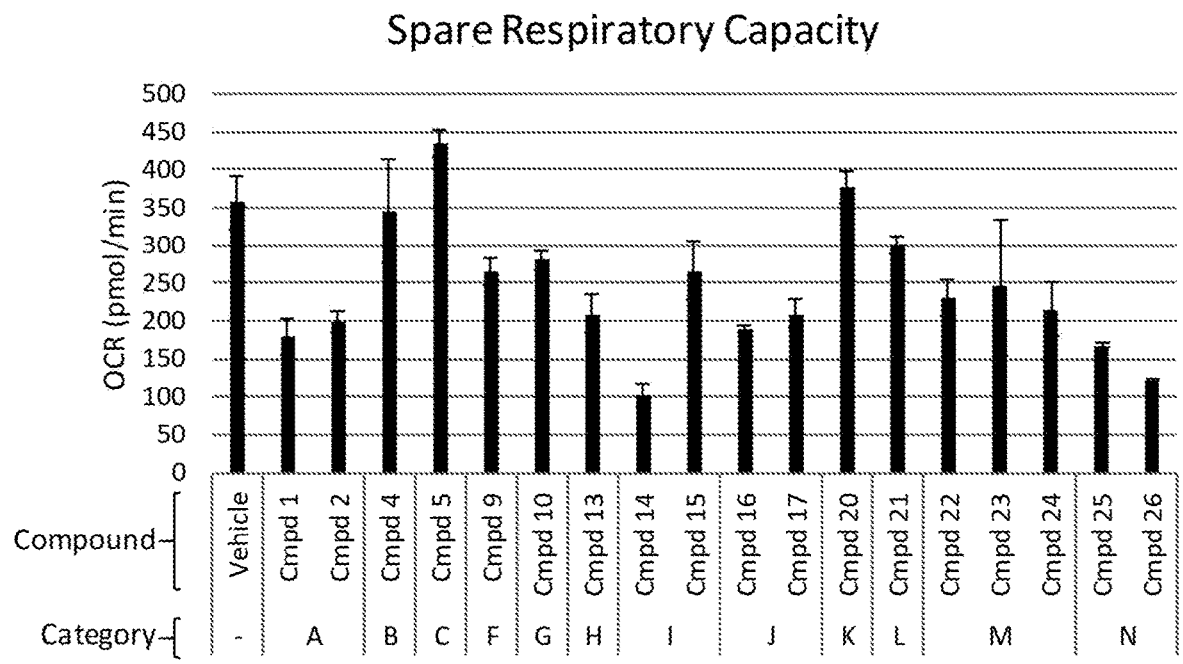
FIGS. 6A-B show that compound treatment can change the metabolic profiles of treated T cells: (A) oxygen consumption rate (OCR) in cells treated under DMSO, or various selected compounds; and (B) basal OCR in cells treated under DMSO, or various selected compounds (refer to Table 1 for compound number and compound category).
Figure 6B:
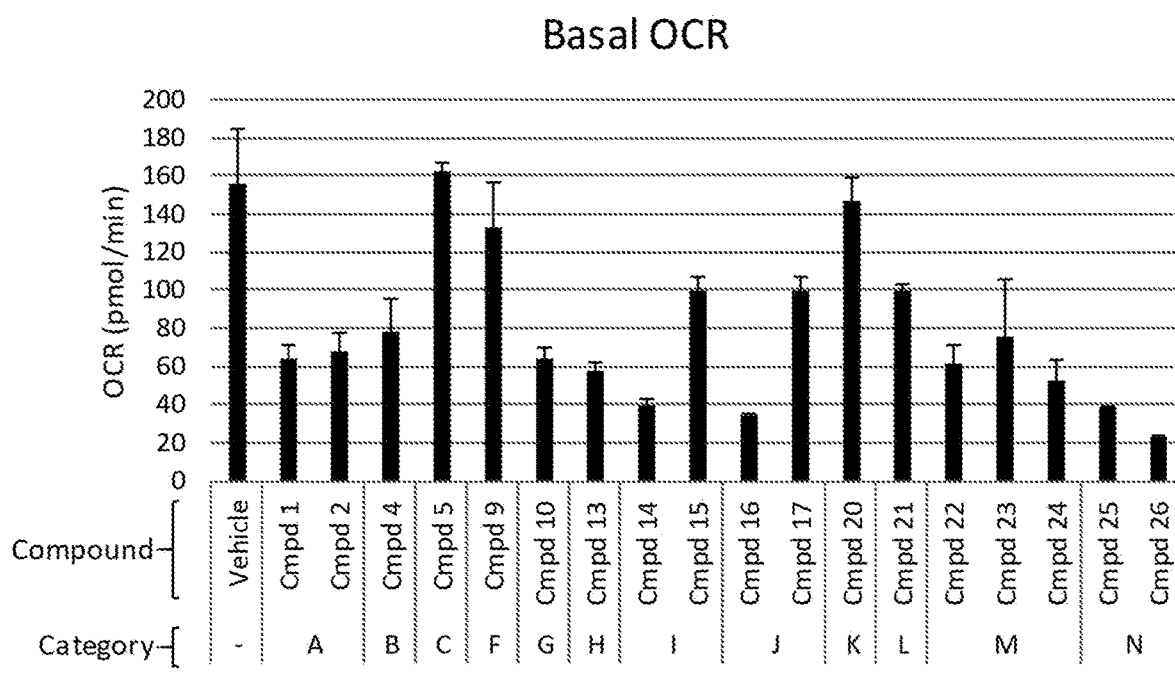

We tested whether compound treatment influenced the metabolism of CD8+ CAR-T cells. After treatment, the cells were washed and resuspended in non-buffered assay medium, and then were seeded in 96-well assay plates and subjected to the Seahorse™ mitostress test assay to measure the basal OCR. The maximal OCR of the cells was measured following addition of the ionophore FCCP into the assay plate. SRC was then determined based on the difference between basal OCR and maximal OCR. The average SRC and basal OCR of treated T cells obtained from two donors are shown in FIGS. 6A-B. Most of the compound-treated T cells had both lower SRC and basal OCR compared to the vehicle control, while IKK inhibitor and Syk inhibitor significantly reduced SRC and basal OCR. T cells treated with CDK inhibitor or Lck inhibitor maintained a similar SRC; and T cells treated with CRAC channel Ca entry blocker, ERK5/BMK1 inhibitor, or Lck inhibitor maintained a similar basal OCR, as the vehicle control (FIGS. 6A and 6B). In addition, T cells treated by the CRAC channel Ca entry blocker, while maintaining similar OCR, have an increased SRC in comparison to the vehicle control. These data indicate that the selected compound treatments can alter the metabolic profile of treated T cells.

Example 6—In Vivo Profiling of T Cells Treated with Selected Compounds

A CD19+ xenograft model designed to interrogate the in vivo functionality of CAR-T cells was used to characterize the ability of the cells to clear tumor after being treated with a selected compound. In brief, a suboptimal therapeutic dose of compound-treated CD19-targeted CAR-T cells was administered to NSG mice bearing Nalm-6-luc CD19+ disseminated tumors. By this stress test, i.e., using a suboptimal dose of CAR-T cells which would fail to control or eliminate tumor, we are able to detect any advantage gained by the CAR-T cells as a result of a compound treatment. CD4+ and CD8+ T cells were transduced with the CAR and activated with anti-CD3/anti-CD28 beads. The CD4+ and CD8+ CAR-T cells were cultured with vehicle or with a compound of Table 1. The CD4+ and CD8+ CAR-T cells were cryopreserved after the 6-day treatment was completed. The treated T cells were thawed, mixed at a 1:1 ratio of CD4+ and CD8+ T cells, and administered to mice at a dose of about $2.5 \times 10^5$ cells. Tumor burden was determined using an IVIS Lumina Series III imaging system (Waltham, Mass.) which measures the total radiance in each mouse and is dependent upon the amount of luciferase expressed by the Nalm-6-luc CD19+ tumor cells.

Figure 7:
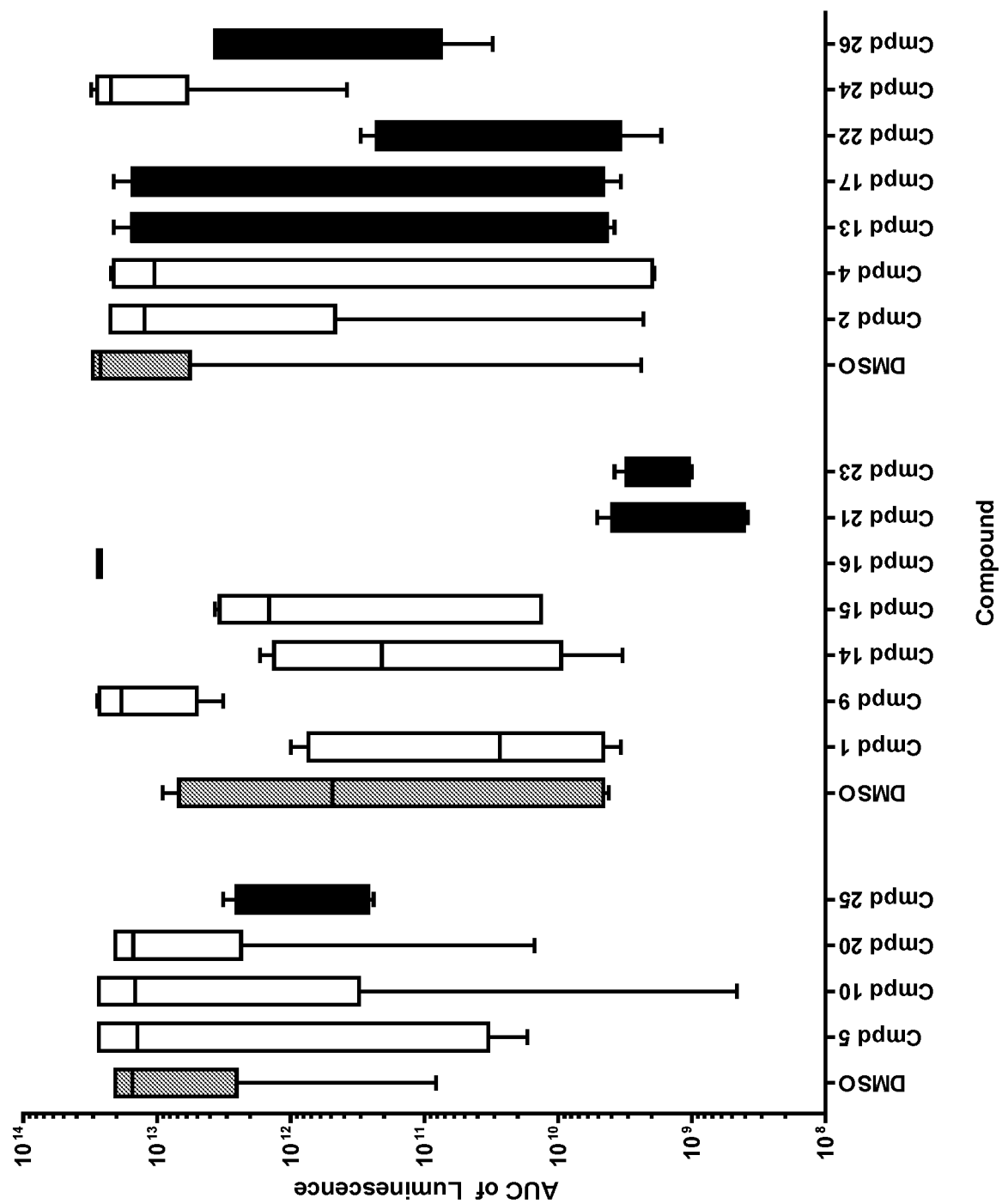
FIG. 7 shows in vivo efficacy of CAR-T cells treated by their respective selected compounds using AUC (Area Under the Curve) of the luminescence representing the remaining tumor cells for the duration of the experiment for each compound-treated CAR-T group (refer to Table 1 for compound number and compound category).

Tumor growth in mice administered CAR-T cells treated with vehicle (DMSO) or individual compounds were compared. FIG. 7 shows the AUC (Area Under the Curve) calculated for the luminescence for the duration of the experiment for each compound-treated CAR-T group. Generally, the lower the AUC, the fewer tumor cells in the animal, and the better the tumor clearance mediated by the transferred cells. As shown, among the tested compounds, Syk inhibitor, Raf inhibitor, PDK1 inhibitor, JAK inhibitor, and IGF-1R inhibitor resulted in improved tumor clearance relative to DMSO (FIG. 7).

Further, in vivo persistence of compound-treated CAR-T cells during and after tumor clearance was also investigated. One of the main correlates of successful CAR-T cell therapy in patients is the persistence of CAR-T cells (i.e., through cell survival and/or cell expansion in vivo). To model CAR-T cell persistence in vivo, CD4+ and CD8+ T cells were separately expanded and transduced with a lentivirus encoding CAR-T2A-Thy1 and cultured in the presence of DMSO or a lentivirus encoding CAR-T2A-GFP and cultured in the presence of a testing compound (Table 3). Then a cohort of mice were injected with a curative dose ($2 \times 10^{\wedge}6$) of CAR-T cells that was composed of CAR-T cell subsets from two different expansion protocols and mixed at approximately a 1:1:1:1 ratio, and the initial ratio of the CAR-T cells subsets in the injection mix was further determined prior to injection. All mice in the cohort had received Nalm-6-luc cells 4 days earlier and were able to clear the tumor by the injected CAR-T cells.

TABLE 3

Cell Subsets for Testing in vivo Persistence During and Post Tumor Clearance

| Cell Subset | Tag | Treatment |
| --- | --- | --- |
| CD4 | Thy1 | DMSO |
| CD8 | Thy1 | DMSO |
| CD4 | GFP | Testing compound |
| CD8 | GFP | Testing compound |

Figure 9:
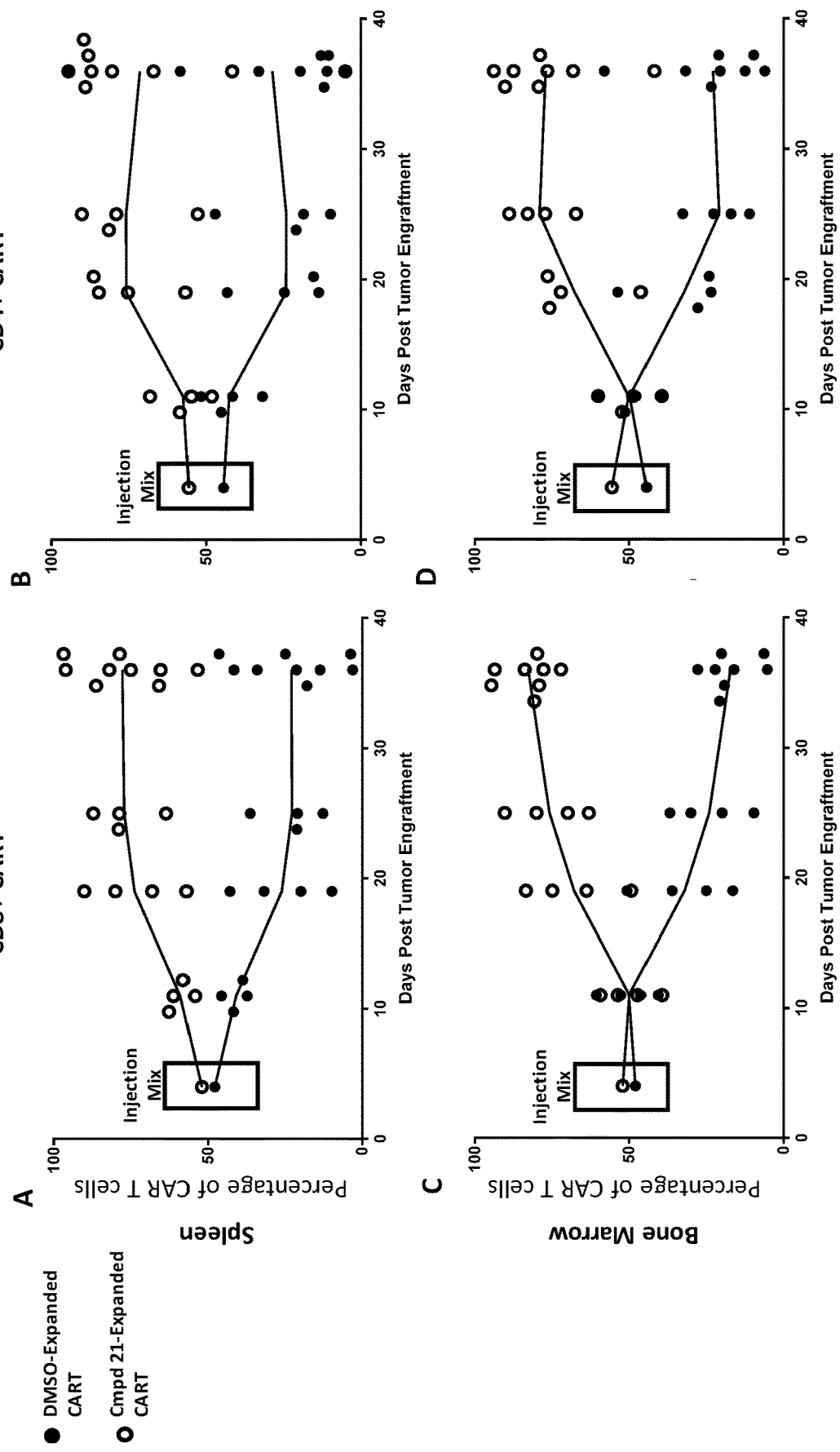
FIG. 9 shows increased persistence of PDK1 inhibitor treated CAR-T cells during and after tumor clearance in vivo: (A) CD8+ CAR-T cells in spleen; (B) CD4+ CAR-T cells in spleen; (C) CD8+ CAR-T cells in bone marrow; (D) CD4+ CAR-T cells in bone marrow.

At day 7, 15, 21, and 32 post CAR-T cell injection (day 0: tumor engraftment, day 4: CAR-T cell injection) mice were sacrificed and the relative proportions of the CAR-T cells expanded in DMSO or the testing compound in both spleen and bone marrow were determined. FIG. 9 exemplifies the effect of a PDK1 inhibitor treatment on CAR-T cell in vivo persistence. As shown, the relative proportions of cells recovered at 7 day-post CAR-T cell injection did not significantly change and roughly reflected the frequency that was present upon injection. However, at 15 days post injection, and every time point thereafter, the proportion of the PDK1 inhibitor treated CAR-T (CD8+ and CD4+) cells was significantly increased relative to the DMSO treated CAR-T cells in the secondary lymphoid organs such as spleen and bone marrow. This indicates increased in vivo persistence and fitness of CAR-T cells treated by the PDK1 inhibitor, offering the potential of a more durable CAR-T cell response and preventing tumor relapse.

To compare the effect of modulation with the PDK1 inhibitor and the PI3K inhibitor on CAR-T cell manufacturing, CAR-T cells were produced in the presence of vehicle (DMSO), PI3K inhibitor (for example, PI103) or PDK1 inhibitor (for example, compound 21) for 8 days. At the end of the manufacturing process, the cells were frozen prior to subsequent functional analysis.

Figure 10A:
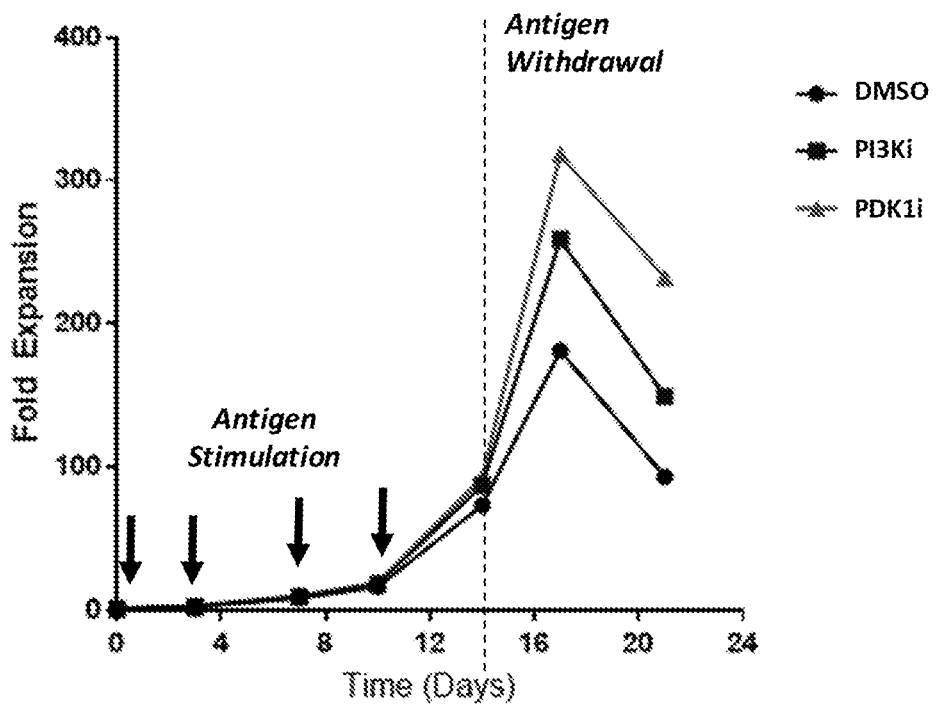
FIGS. 10A-D show that treatment with either a PI3K inhibitor or a PDK1 inhibitor improves CAR-T cell expansion (i) after antigen stimulation and withdrawal: (A) time course of CAR-T cell expansion; (B) total CAR-T cell expansion; and (ii) AUC values for expansion curve over 14 days with stimulation from anti-CAR antibody coated beads: (C) CD19 CAR-T cell expansion with CD19-Fc coated beads; (D) BCMA CAR-T cell expansion with BCMA-Fc coated beads.
Figure 10B:
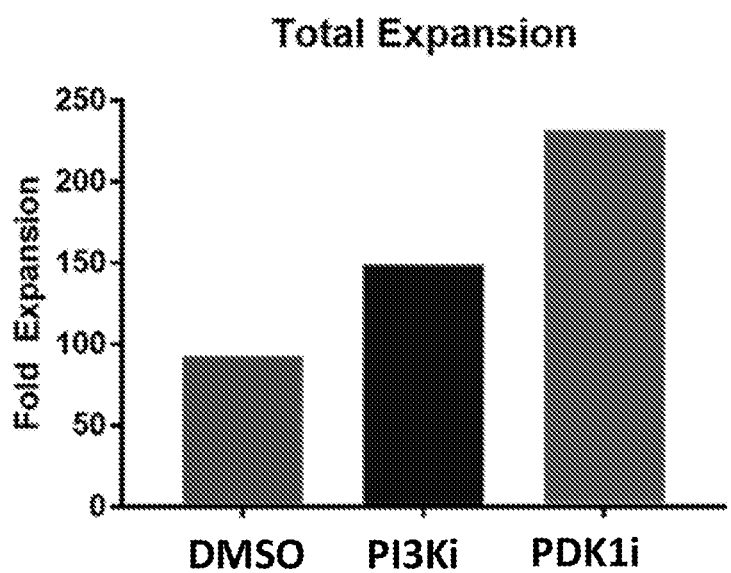
Figure 10C:
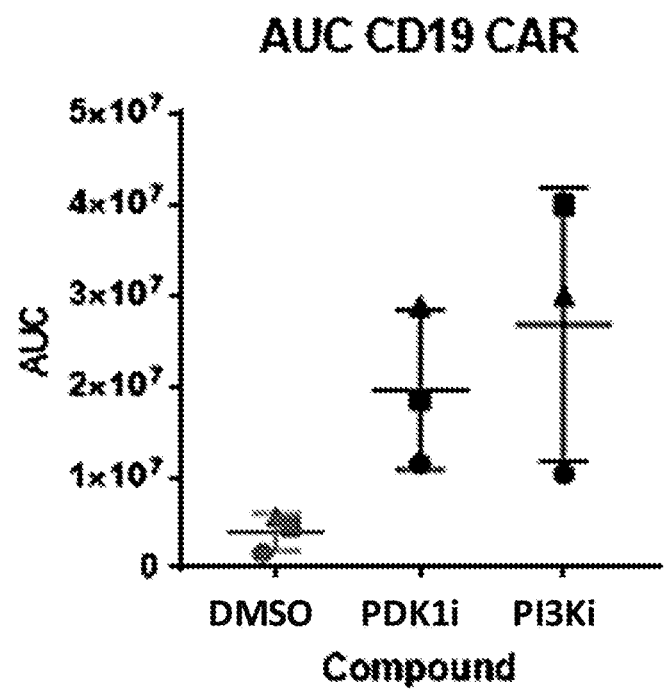
Figure 10D:
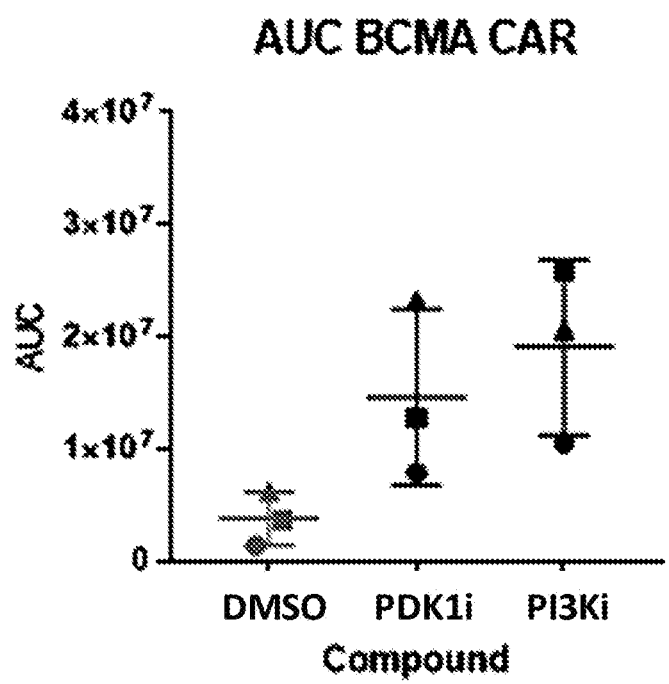

The ability of CAR-T cells produced in the presence of vehicle, PI3K inhibitor, or PDK1 inhibitor to expand through multiple rounds of antigen stimulation was measured in a serial restimulation assay, wherein cryopreserved CAR-T cells were thawed and co-cultured in the presence of antigen-bearing, irradiated target cells. Every 3 to 4 days the CAR-T and target cell ratios were readjusted to approximately 1:1. Over the course of the serial restimulation assay (FIG. 10A), and as measured by total expansion (FIG. 10B), CAR-T cells generated in the presence of PDK1 inhibitor, expanded to a greater extent, compared to DMSO vehicle control and PI3K inhibitor treated CAR-T cells. As an alternative to using antigen-bearing, irradiated target cells for CAR-T cell stimulation, cryopreserved CAR-T cells from three independent donors produced in the presence of vehicle, PI3Ki or PDKli were thawed in T cell growth media and subsequently assessed for expansion and survival, as measured by AUC (area under the curve) of the expansion over 14 days of stimulation with anti-CAR antibodies conjugated to beads. PDK1-inhibitor treatment during production improved the overall accumulation of both CD19 and BCMA CAR-T cells relative to CAR-T cells generated in the presence of DMSO in all three donors tested (FIGS. 10C and 10D). Additionally, the expansion and survival of both CD19 and BCMA CAR-T cells generated in the presence PDK1 inhibitor was comparable to those generated in the presence of PI3K inhibitor.

Figure 11A:
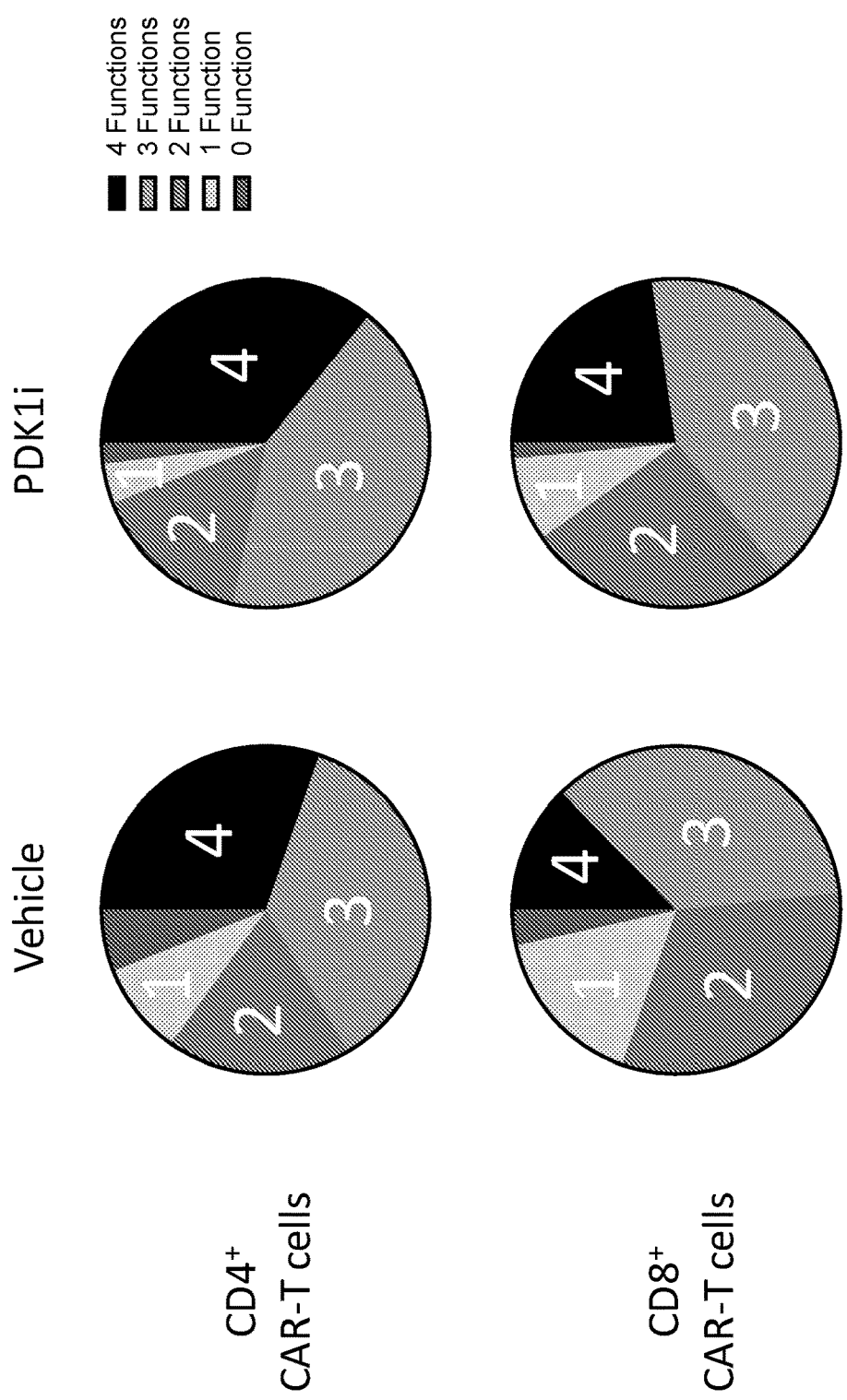
FIGS. 11A-C: (A) shows that PDK1 inhibitor treatment increases the portion of multifunctional cells as defined by cytokine production (IL-2, IFNγ and TNFα), or surface expression of CD107a, thus improving CAR-T functionality; (B) production of IL-2, IFNγ and TNFα in CD19 CAR-T cells treated with PDK1 inhibitor; and (C) production of IL-2, IFNγ and TNFα in BCMA CAR-T cells treated with PDK1 inhibitor, upon initial stimulation ("Day 0") or upon restimulation ("Day 14") with target cells.
Figure 11B:
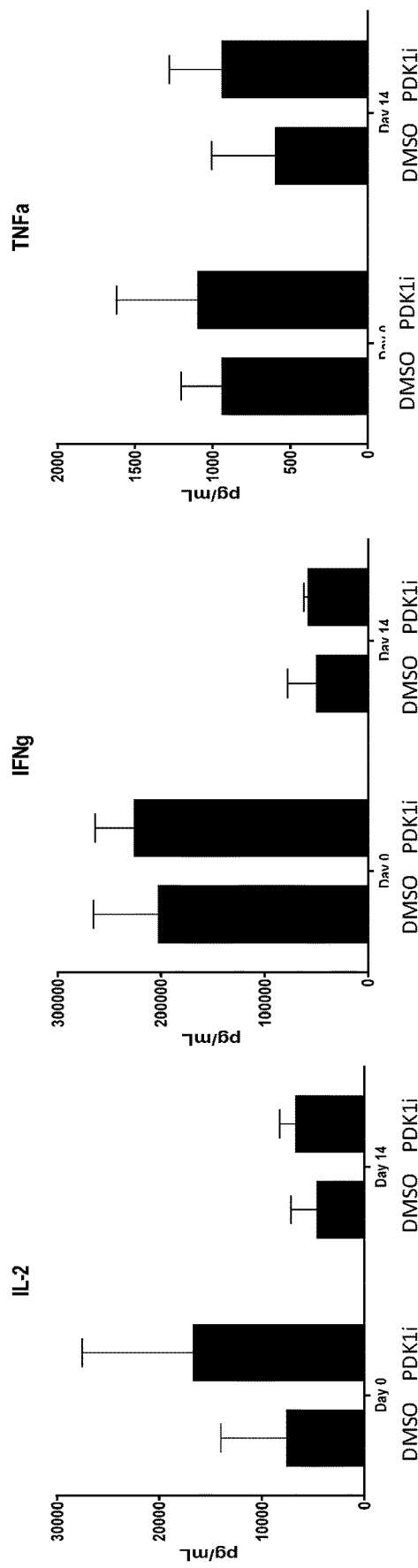
Figure 11C:
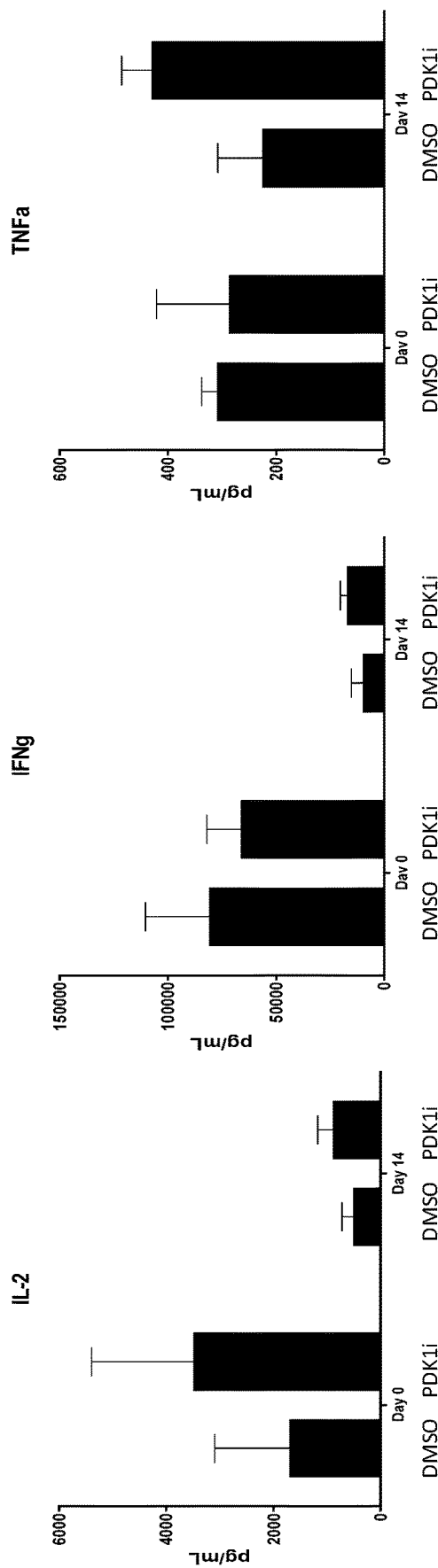

To assess the polyfunctionality of CAR-T cells that had been repeatedly restimulated in vitro, an intracellular cytokine staining was carried out on DMSO or PDK1 inhibitor treated CD19 CAR-T cells following 3 rounds of in vitro antigen stimulation of the cells as described above. For each stimulation session DMSO or PDK1 inhibitor treated CAR-T cells were co-cultured with irradiated K562-CD19 target cells at 1:1 ratio overnight. Following this co-culture, the CAR-T cells were stimulated with PMA and ionomycin in the presence of protein transport inhibitors and incubated for a further 4 hours. Cells were then washed, fixed, permeabilized and stained for IFNγ, TNFα, IL-2 and CD107a expression by flow cytometry. Polyfunctionality was determined by calculating the combinations of cytokines produced by each of the compound treated CAR-T cell types. As shown in FIG. 11A, both PDK1 inhibitor treated CD4+ and CD8+ CAR-T cells populations comprise higher percentages of cells that can elicit 3 or 4 effector function compared to DMSO, suggesting CAR-T production with PDK1 inhibitor treatment can also increase CAR-T cell polyfunctionality. The kinetics of cytokine production was further dissected by stimulating CAR-T cells with antigen-bearing cells (i) immediately following thaw (day 0) and (ii) following 14 days of anti-CAR antibody driven activation and expansion via MSD analysis. As shown in FIGS. 11B and 11C, CD19 and BCMA CAR-T cells generated in the presence of PDK1 inhibitor produced, on the whole, greater amounts of IL-2 immediately following thaw, compared to CAR-T generated alongside DMSO treatment. IFNγ and TNF production post thaw were comparable between PDK1 inhibitor and DMSO treated CAR-T cells. After 14 days of CAR activation, both PDK1 and DMSO treated CAR-T cells were again stimulated with antigen-bearing target cells and cytokine production was similarly assessed. Compared to post thaw, overall cytokine IL-2, IFNγ, and TNF production was reduced after 14 days of stimulation, however CAR-T cells generated along with PDK1 inhibitor expressed overall greater amounts of IL-2 compared to DMSO treated CAR-T cells.

Figure 12A:
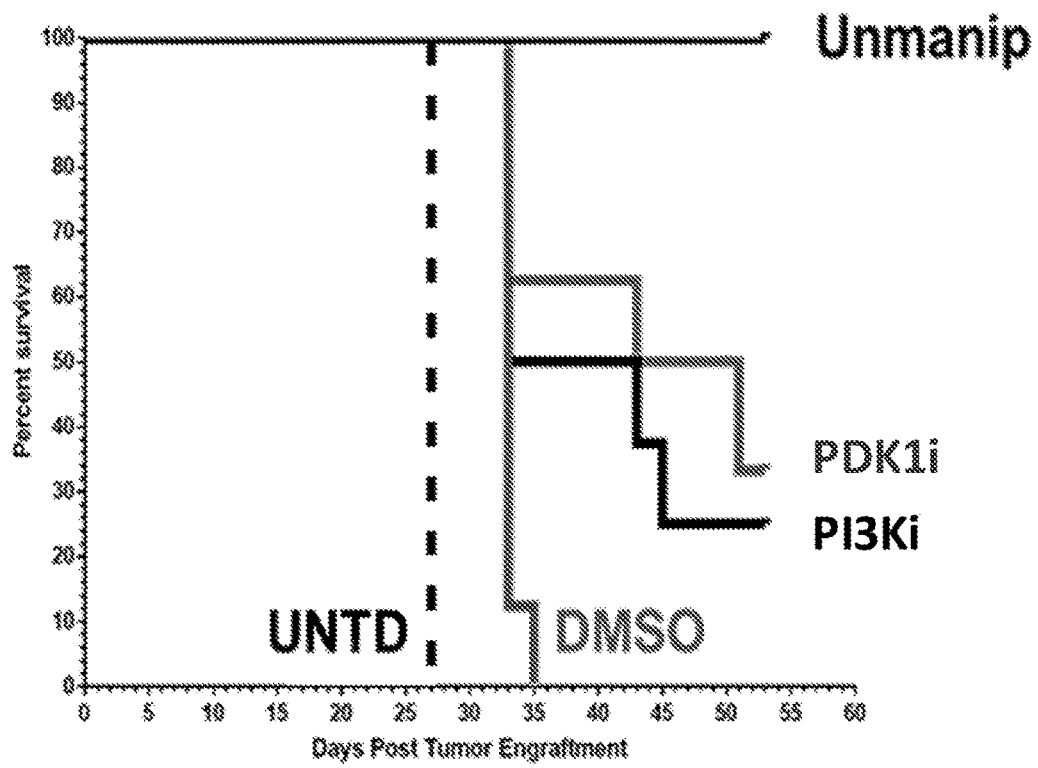
FIGS. 12A-B show that CAR-T cells produced in the presence of either a PI3K inhibitor or a PDK1 inhibitor improves survival in (A) a Nalm6/NSG tumor model; (B) Raji/NSG tumor model.
Figure 12B:
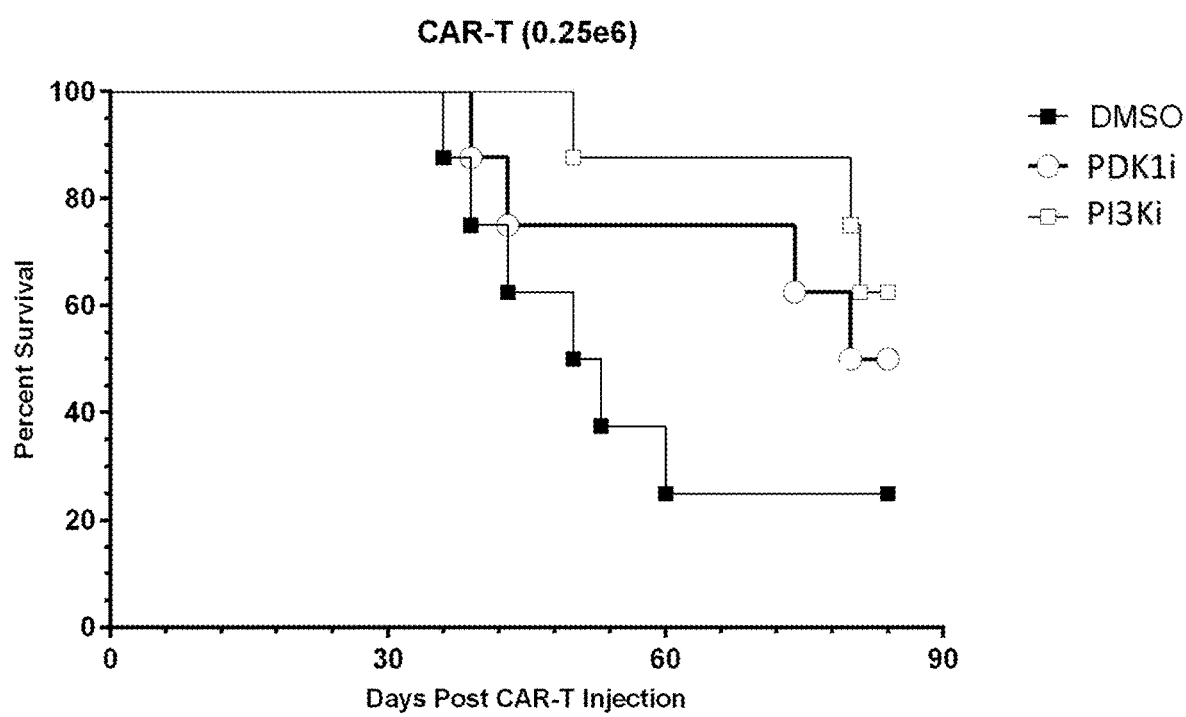

Next, an in vivo assay was conducted to further characterize CAR-T cells produced in the presence of a PI3K inhibitor or a PDK1 inhibitor for tumor clearance. NSG mice were injected with a human leukemia line, Nalm-6. Four days later, mice were treated with a suboptimal dose ($3\times10^5$) of freshly thawed CD19 CAR-T cells generated in the presence of vehicle ("DMSO" n=8), PI3K inhibitor (n=8), or PDK1 inhibitor (n=8). Some tumor bearing mice (n=2) also received expanded T cells that were not transduced with CAR (untransduced or "UNTD"). Negative control mice (n=2, "Unmanip") received neither tumor nor CAR T cells. As shown in FIG. 12A, this suboptimal dose of CAR-T cells fails to protect mice receiving DMSO generated CAR-T cells. On the other hand, even at this low dose of CAR-T cells, mice receiving CAR-T cells generated alongside either PDK1 inhibitor or PI3K inhibitor demonstrated prolonged survival. In an additional demonstration, NSG mice intravenously engrafted with an alternative human tumor line, Raji. Seven days later, a suboptimal dose ($2.5\times10^5$) of CD19 CAR-T cells produced in the presence of DMSO, PDK1 inhibitor, or PI3K inhibitor were transferred and the survival of the tumor bearing mice was monitored. The survival of mice receiving CAR-T cells generated with PDK1 inhibitor or PI3K inhibitor was substantially improved compared to mice receiving DMSO treated CAR-T cells (FIG. 12B).

Figure 13A:
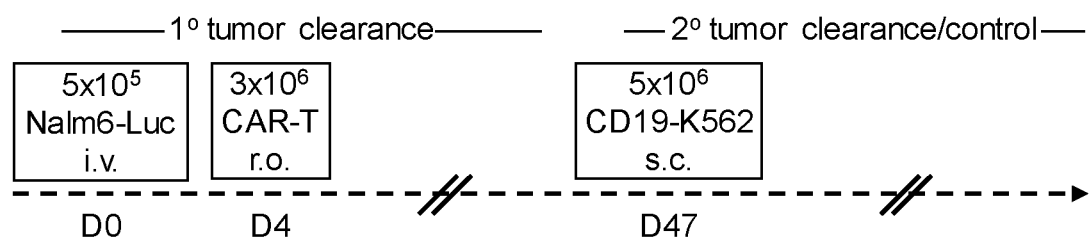

To further assess tumor clearance and control by CAR-T cells modulated with a selected compound, a two-stage tumor clearance model was established. As illustrated in FIG. 13A, NSG mice were injected with $5 \times 10^5$ luciferase expressing Nalm6 tumor cells intravenously; four days later the tumor bearing mice were injected with a total of $3 \times 10^6$ CD19 CAR-T (1:1 ratio of CD4:CD8) produced in the presence of DMSO, PI3Ki (for example, PI-103), and PDK1 inhibitor, respectively; 47 days after primary tumor injection, all mice that had durably cleared tumor, as measured by IVIS imaging, were re-challenged subcutaneously with $5 \times 10^6$ K562 tumor cells that had been engineered to express both CD19 and luciferase. Secondary tumor burden was measured via bi-weekly caliper measurements and IVIS imaging. IVIS control mice received neither tumor nor CAR-T cells and served as the background luminescence for the IVIS imager.

As shown in FIGS. 13B and 13C, the CAR-T cells generally led to rapid and durable tumor control. Six of eight mice receiving DMSO-, seven of eight mice receiving PI103-, and all seven mice receiving PDK1-inhibitor-treated CAR-T cells contained and eliminated primary Nalm6 tumor within 1-3 weeks. Tumor bearing mice that received an injection without CAR-T cells demonstrated rapid tumor growth. (FIG. 13B). PDK1-inhibitor treated CAR-T cells displayed significantly (*$p<0.05$, $p<0.01$, *$p<0.001$, $p<0.0001$, Kruskal-Wallis 1-way ANOVA) greater in vivo efficacy at day 11 post primary tumor injection, compared to both DMSO and PDK1 inhibitor treated CAR-T (FIG. 13C). At later time points there was no significant differences amongst CAR-T treated groups as all groups contained and cleared Nalm6 tumor.

Figures 13D, 13E:
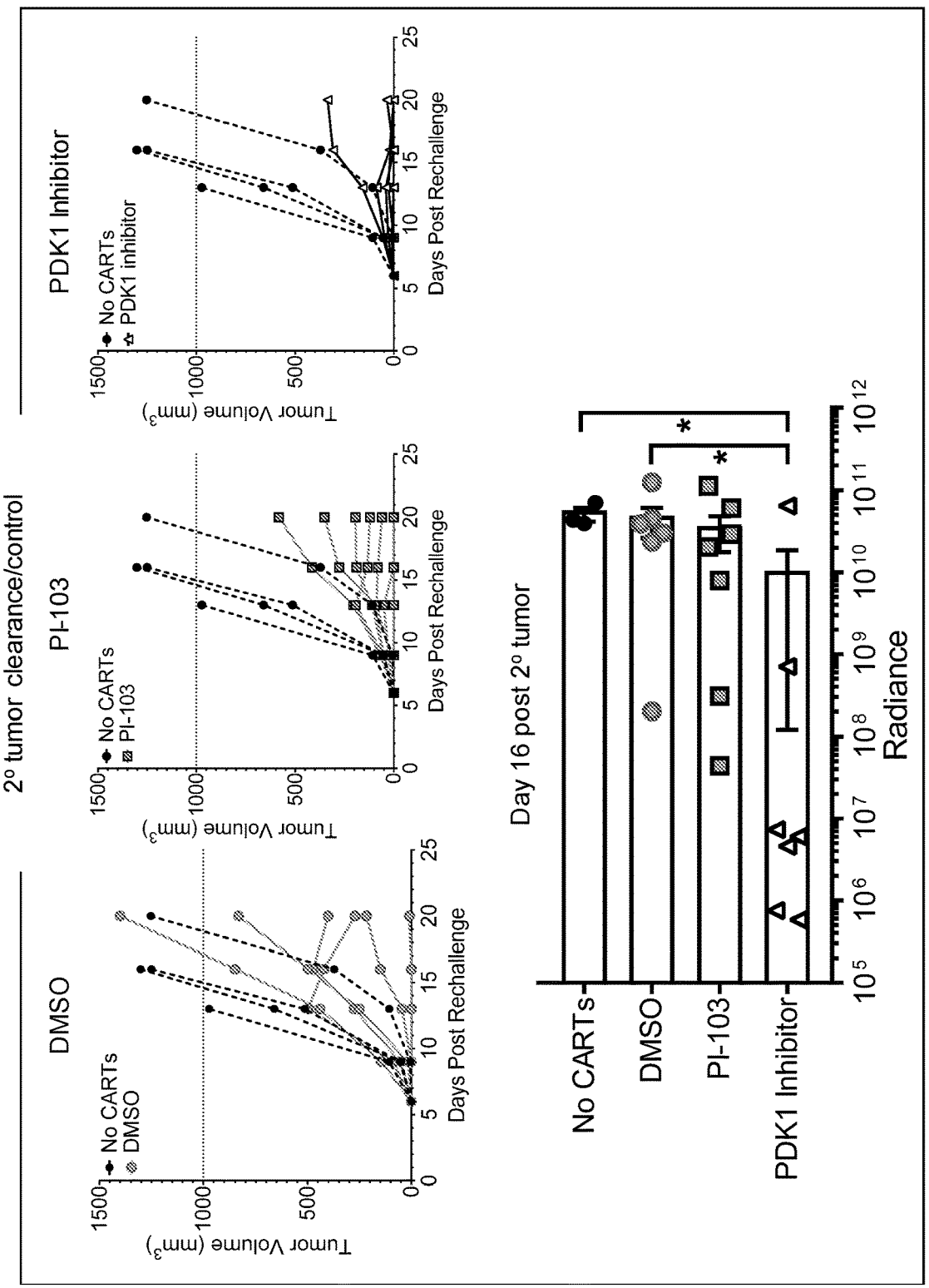

47 days post primary tumor injection, all mice that had durably cleared primary tumor were re-challenged subcutaneously with $5 \times 10^6$ K562 tumor cells that had been engineered to express both CD19 and luciferase. As shown in FIG. 13D, 5 of the 6 mice containing DMSO-treated CAR-T failed to control secondary tumor and demonstrated rapid tumor growth (FIG. 13D, left panel). Moreover, although PI-103 treated CAR-T cells (FIG. 13D, middle panel) perform better when compared to DMSO treated CAR-T cells, PDK1-treated CAR-T (FIG. 13D, right panel) demonstrated superior and rapid control of secondary tumor. Since tumors within 4 of 7 PDK1 CAR-T mice were below the level of detection via caliper measurement, focal IVIS imaging was performed on the tumor site on day 16 post K562 rechallenge to better quantify tumor burden (note IVIS imaging of solid tumors saturates at radiances $>10^{10}$). As shown in FIG. 13E, the secondary tumor burden was significantly (*$p<0.05$, Kuskal Wallis 1 way ANOVA) less within mice receiving PDK1-treated CAR-T cells, compared to tumor control mice and mice receiving DMSO-treated CAR-T cells. These results indicate that CAR-T cells produced in the presence of PDK1 inhibitor show greater efficacy after secondary tumor re-challenge, possibly due to improved in vivo (i) persistence, (ii) effector function, and/or (iii) tumor infiltration.

Figure 14A:
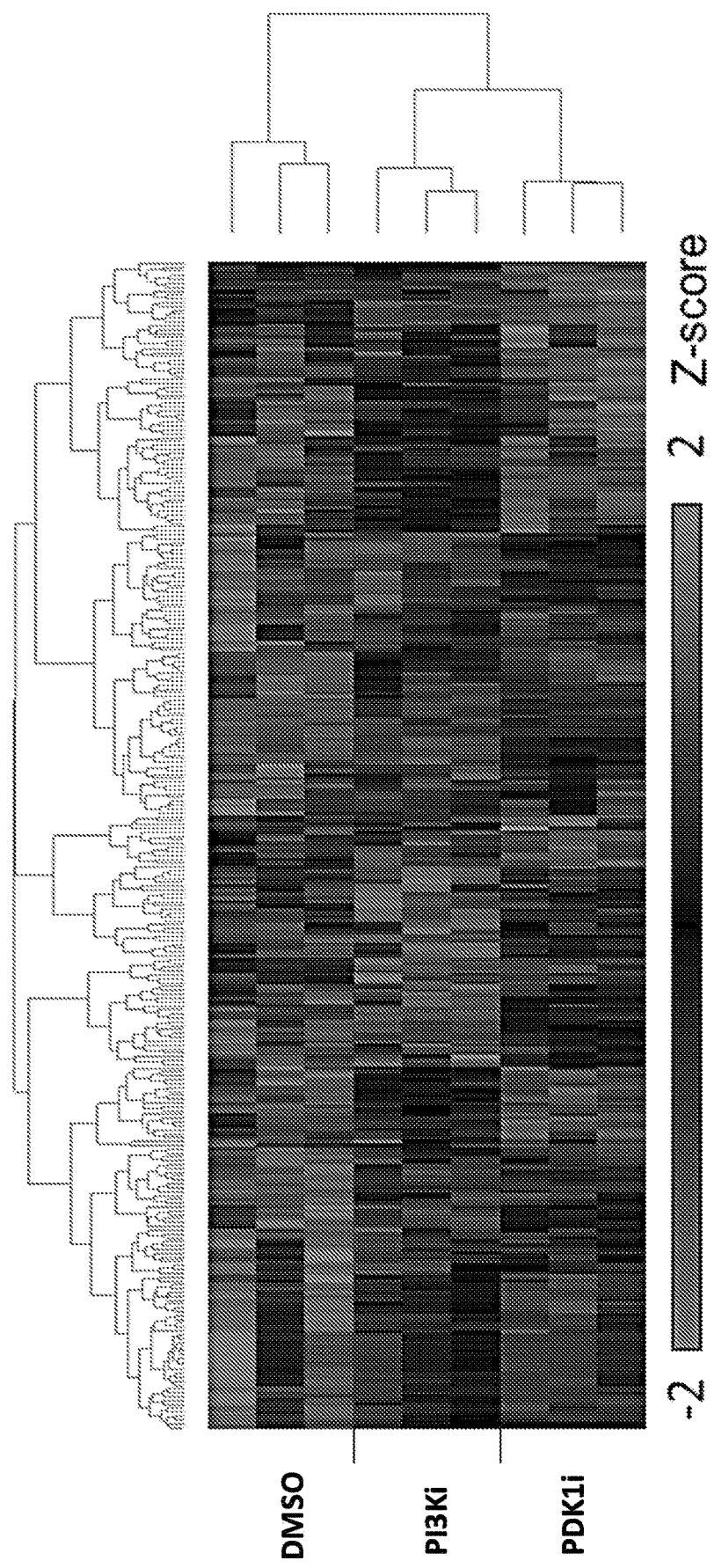
FIGS. 14A-B: (A) shows the color-coded gene expression heat map (blue=downregulated and red=upregulated) with Z-score normalized expression levels of differentially expressed genes in vehicle, PI3K inhibitor and PDK1 inhibitor treated CAR-T cells; and (B) differential gene expression in CD4 and CD8 T cells generated in the presence of vehicle (DMSO), PI3Ki or PDK1i where overlapping (blue or green symbols) or unique (purple: PDK1i treated, red: PI3Ki treated) differential gene expression that were significant by adjusted p-value for either cohort (n=3) is shown.
Figure 14B:
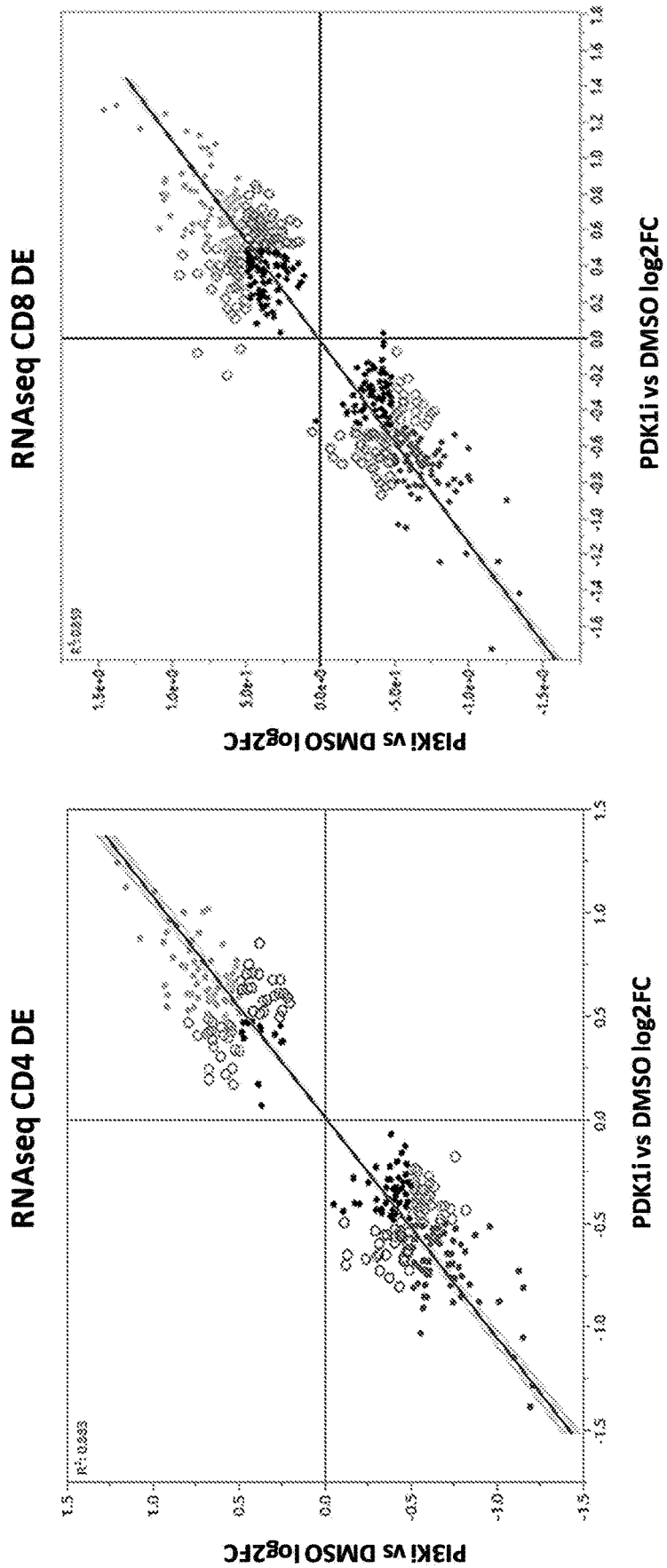

CD4+ and CD8+ CAR-T cells from healthy donors (n=3) were generated by lentiviral transduction and expanded in vitro for 8 days in the presence of vehicle control (DMSO), PI3K inhibitor, or PDK1 inhibitor. The cells were then frozen, and later thawed, rested and then analyzed for transcriptional profile. Total RNA from the CD8+ cells was analyzed with Affymetrix Human Transcriptome Array GeneChips (HTA-2.0; ThermoFisher, Waltham, Mass.). Complete linkage hierarchical clustering of all samples was performed on more than 300 significantly differentially expressed genes (>2-fold differential expression & f-test <0.05) using a Euclidean similarity measurement. The color-coded gene expression heat map in FIG. 14A (blue=downregulated and red=upregulated) visualizes Z-score normalized expression levels of these genes. The heat map shows that compound-treated CAR-T cells have an altered transcriptional profile compared to DMSO-treated CAR-T cells. Furthermore, there are sets of genes that are also differentially expressed between PI3Ki- and PDKli-treated CD8 T cells. As a parallel approach for transcriptional analysis using the same cell preparations from FIG. 14A, the differential gene expression in the PI3Ki- or PDKli-treated cohorts using RNAseq analysis is shown in FIG. 14B for CD4 and CD8 cells, demonstrating differential gene expression of treated (PDKli or PI3Ki) versus vehicle (DMSO) CAR-T cells averaged over three donors. FIG. 14B shows overlapping genes that are differentially expressed with treatment of either PDKli or PI3Ki (blue or green colored symbols), or the unique genes that are differentially expressed in PI3Ki-treated cells (red symbols) or PDKli-treated cells (purple symbols), for genes that were significant by adjusted p-value for either cohort. As seen, the transcriptional profiles are significantly different between CAR-T cells cultured in the presence of either compound relative to vehicle. Moreover, CAR-T cells produced in the presence of a PI3K inhibitor exhibit an expression pattern quite different from the pattern shown by CAR-T cells produced in the presence of a PDK1 inhibitor, suggesting potentially different signaling pathways (for example, AKT independent PDK1 pathway versus AKT dependent PI3K pathway) and mechanisms of action mediated by these inhibitors.

As shown by all analyses presented herein, PDK1 inhibitor guided CAR-T cells has demonstrated improved expansion over multiple rounds of in vitro serial restimulation; improved tumoricidal efficiency despite prior multiple rounds of in vitro exposure to antigen-bearing target cells; greater resistance to exhaustion; increased engraftment and homing to secondary lymphoid organs during and after tumor clearance in vivo; and prolonged survival following tumor-clearance. PDK1 inhibitor-guided CAR-T expansion results in CAR-T cells that are more polyfunctional and have a distinct gene expression signature. The results indicate that a CAR-T cell composition produced in the presence of a PDK1 inhibitor can alter T cell biology in ways that confer significant functional advantages in vivo.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure without departing from the scope and spirit of the invention.

All patents and publications mentioned in the specification are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A composition comprising a population of lymphocytes and a Phosphoinositide-dependent kinase-1 (PDK1) inhibitor, wherein the PDK1 inhibitor inhibits AKT independent signaling in a subpopulation of lymphocytes relative to inhibiting AKT dependent signaling and improves therapeutic potential of the subpopulation of lymphocytes upon or following contact with the PDK1 inhibitor in comparison to another subpopulation of lymphocytes without contacting with the PDK1 inhibitor.

2. The composition of claim 1, wherein the PDK1 inhibitor
   (a) improves cell expansion, maintenance, differentiation, dedifferentiation, and/or survival rate;
   (b) improves cell proliferation, cytotoxicity, persistence, cytokine response and secretion, and/or cell recall; and/or
   (c) increases a number or relative ratio of one or more desired subpopulations of lymphocytes in the population of lymphocytes.

3. The composition of claim 2, wherein the one or more desired subpopulations of lymphocytes having an increased number or relative ratio comprise:
   (a) naïve T cells, stem cell memory T cells, and/or central memory T cells;
   (b) type I NKT cells; or
   (c) adaptive NK cells.

4. The composition of claim 1, wherein the lymphocytes comprise T cells, NKT cells, and/or NK cells.

5. The composition of claim 1, wherein the lymphocytes are isolated from or comprised in peripheral blood, bone marrow, lymph node tissue, cord blood, thymus tissue, tissue from a site of infection, ascites, pleural effusion, spleen tissue, or tumors; or
   wherein the lymphocytes are isolated from:
   (a) a healthy subject;
   (b) a subject having an autoimmune disease, a hematopoietic malignancy, a virus infection or a solid tumor;
   (c) a subject previously administered genetically modified lymphocytes; or
   (d) a subject that is CMV seropositive.

6. The composition of claim 5, wherein the isolated lymphocytes
   (a) are genomically engineered and comprise an insertion, a deletion, or a nucleic acid replacement; or
   (b) comprise at least one genetically modified modality.

7. The composition of claim 6, wherein the genetically modified modality comprises at least one of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the lymphocytes.

8. The composition of claim 7, wherein the genetically modified modality comprises one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; and (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

9. The composition of claim 6, wherein the isolated lymphocytes comprise an exogenous nucleic acid encoding a T Cell Receptor (TCR) and/or a Chimeric Antigen Receptor (CAR).

10. The composition of claim 1, wherein the lymphocytes
    (a) are differentiated in vitro from stem cells, hematopoietic stem or progenitor cells, or progenitor cells; or
    (b) are trans-differentiated in vitro from non-pluripotent cells of hematopoietic or non-hematopoietic lineage.

11. The composition of claim 10,
    wherein the stem cells comprise induced pluripotent stem cells (iPSCs) or embryonic stem cells (ESCs);
    wherein the progenitor cell is a CD34+hemogenic endothelium cell, a multipotent progenitor cell, a T cell progenitor cell, an NK progenitor cell, or an NKT progenitor cell;
    wherein the stem cell, hematopoietic stem or progenitor cell, or progenitor cell
    (a) is genomically engineered and comprises an insertion, a deletion, or a nucleic acid replacement, or
    (b) comprises at least one genetically modified modality.

12. The composition of claim 11, wherein the stem cell, hematopoietic stem or progenitor cell, or progenitor cell comprises an exogenous nucleic acid encoding protein comprising a T Cell Receptor (TCR) and/or a Chimeric Antigen Receptor (CAR).

13. The composition of claim 1, wherein the PDK1 inhibitor comprises GSK2334470.

14. The composition of claim 1, further comprising one or more additives selected from the group consisting of peptides, antibodies, antibody fragments, cytokines, mitogens, growth factors, small RNAs, dsRNA, mononuclear blood cells, feeder cells, feeder cell components or replacement factors, vectors comprising one or more polynucleic acids of interest, chemotherapeutic agents or radioactive moieties, and immunomodulatory drugs (IMiDs).

15. The composition of claim 1, wherein the composition further comprises at least one organic solvent selected from the group consisting of dimethyl sulfoxide (DMSO), N,N-dimethylformamide (DMF), dimethoxyethane (DME), dimethylacetamide, ethanol and combinations thereof.

16. The composition of claim 1, wherein the composition comprises T cells.

17. The composition of claim 16, wherein the T cells comprise CAR-T cells.

18. A method of modulating lymphocytes, comprising:
    contacting a subpopulation of lymphocytes with a PDK1 inhibitor of claim 1 for a time sufficient to obtain modulated the subpopulation of lymphocytes having improved therapeutic potential and/or having an increase in one or more properties indicative of therapeutic potential, for adoptive cell therapy, compared to another subpopulation of lymphocytes without contacting with the PDK1 inhibitor, wherein the PDK1 inhibitor inhibits AKT independent signaling relative to inhibiting AKT dependent signaling.

19. The method of claim 18, wherein the modulated lymphocytes comprise:
    (a) improved proliferation, cytotoxicity, cytokine response, cytokine release, cell recall, and/or persistence;
    (b) improved cell expansion, maintenance, differentiation, de-differentiation, and/or survival rate; or (c) an increased number or relative ratio of one or more desired subpopulations of immune cells, in comparison to immune cells not contacted with the PDK1 inhibitor.

20. The method of claim 18, wherein the PDK1 inhibitor comprises: GSK2334470.

21. A method of making a therapeutic composition comprising modulated immune cells comprising T, NK or NKT cells for cell therapies according to claim 18.

* * * * *